(12) United States Patent
Kourtis et al.

(10) Patent No.: US 9,114,024 B2
(45) Date of Patent: Aug. 25, 2015

(54) SYSTEMS, DEVICES, AND METHODS FOR ANCHORING ORTHOPAEDIC IMPLANTS TO BONE

(71) Applicant: Biomimedica, Inc., Ripon, CA (US)

(72) Inventors: Lampros Kourtis, San Francisco, CA (US); Michael J. Jaasma, San Francisco, CA (US); David Myung, Santa Clara, CA (US); Michael C. Hollis, Collierville, TN (US); Vernon Hartdegen, Collierville, TN (US)

(73) Assignee: Biomimedica, Inc., Ripon, CA (US)

( * ) Notice: Subject to any disclaimer, the term of this patent is extended or adjusted under 35 U.S.C. 154(b) by 80 days.

(21) Appl. No.: 13/683,731

(22) Filed: Nov. 21, 2012

(65) Prior Publication Data
US 2013/0131741 A1 May 23, 2013

Related U.S. Application Data

(60) Provisional application No. 61/562,187, filed on Nov. 21, 2011, provisional application No. 61/566,558, filed on Dec. 2, 2011, provisional application No. 61/566,567, filed on Dec. 2, 2011.

(51) Int. Cl.
*A61F 2/46* (2006.01)
*A61F 2/00* (2006.01)
(Continued)

(52) U.S. Cl.
CPC ............ *A61F 2/4603* (2013.01); *A61F 2/0095* (2013.01); *A61F 2/30756* (2013.01);
(Continued)

(58) Field of Classification Search
CPC ... A61F 2/46; A61B 17/1664; A61B 17/1666

USPC ........................................................ 606/99
See application file for complete search history.

(56) References Cited

U.S. PATENT DOCUMENTS 3,053,251 A   9/1962   Black et al.
3,702,611 A   11/1972  Fishbein
(Continued)

FOREIGN PATENT DOCUMENTS

EP   1779875 A1   5/2007
GB   2372707 A    9/2002
(Continued)

OTHER PUBLICATIONS

Myung et al.; U.S. Appl. No. 13/905,028 entitled "Polyurethane-grafted hydrogels," filed May 29, 2013.
(Continued)

*Primary Examiner* — Andrew Yang
(74) *Attorney, Agent, or Firm* — Shay Glenn LLP

(57) ABSTRACT

Methods, devices, and systems for delivering and attaching flexible implants to a bone or joint surface. An implant container includes a first component for surrounding and enclosing an implant and a second component adapted for maintaining, supporting, and conforming the shape of the implant. The implant container designed to have at least one component attachable to the implant and to a delivery instrument or tool. The implant container component having a material allowing transmission of light through a thickness of the container and a thickness of an attached implant to cure an adhesive placed between the implant and a bone surface. Additionally, embodiments described provide delivery instruments and tools for attaching implants and implants within containers to a joint or bone surface.

42 Claims, 63 Drawing Sheets

(51) Int. Cl.
*A61F 2/30* (2006.01)
*A61B 17/17* (2006.01)
*A61B 17/16* (2006.01)
*A61F 2/34* (2006.01)
*A61F 2/36* (2006.01)
*A61F 2/38* (2006.01)
*A61F 2/40* (2006.01)

(52) U.S. Cl.
CPC ............ *A61F2/4618* (2013.01); *A61F 2/4657* (2013.01); *A61F 2/4675* (2013.01); *A61B 17/1664* (2013.01); *A61B 17/1666* (2013.01); *A61B 17/1764* (2013.01); *A61F 2/34* (2013.01); *A61F 2/36* (2013.01); *A61F 2/38* (2013.01); *A61F 2/40* (2013.01); *A61F 2002/3009* (2013.01); *A61F 2002/30014* (2013.01); *A61F 2002/30069* (2013.01); *A61F 2002/30594* (2013.01); *A61F 2002/30757* (2013.01); *A61F 2002/30878* (2013.01); *A61F 2002/30971* (2013.01); *A61F 2002/3412* (2013.01); *A61F 2002/465* (2013.01); *A61F 2002/4627* (2013.01); *A61F 2002/4628* (2013.01); *A61F 2002/4629* (2013.01); *A61F 2002/4631* (2013.01); *A61F 2002/4685* (2013.01); *A61F 2002/4696* (2013.01)

(56) References Cited

U.S. PATENT DOCUMENTS

| | | |
|---|---|---|
| 3,826,678 A | 7/1974 | Hoffman et al. |
| 3,833,404 A | 9/1974 | Sperling et al. |
| 3,939,049 A | 2/1976 | Ratner et al. |
| 4,035,848 A | 7/1977 | Wagner |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,439,583 A | 3/1984 | Gould et al. |
| 4,452,925 A | 6/1984 | Kuzma et al. |
| 4,468,499 A | 8/1984 | Siegfried et al. |
| 4,477,604 A | 10/1984 | Oechsle, III |
| 4,487,865 A | 12/1984 | Balazs et al. |
| 4,500,676 A | 2/1985 | Balazs et al. |
| 4,502,161 A | 3/1985 | Wall |
| 4,536,554 A | 8/1985 | Lim et al. |
| 4,575,539 A | 3/1986 | DeCrosta et al. |
| 4,621,637 A | 11/1986 | Fishbein |
| 4,678,468 A | 7/1987 | Hiroyoshi |
| 4,680,336 A | 7/1987 | Larsen et al. |
| 4,693,715 A | 9/1987 | Abel, Jr. |
| 4,836,884 A | 6/1989 | McAuslan |
| 4,846,841 A | 7/1989 | Oh |
| 4,865,601 A | 9/1989 | Caldwell et al. |
| 4,913,144 A | 4/1990 | Del Medico |
| 4,931,287 A | 6/1990 | Bae et al. |
| 4,966,934 A | 10/1990 | Huang et al. |
| 4,973,493 A | 11/1990 | Guire |
| 4,978,352 A | 12/1990 | Fedorov et al. |
| 5,030,230 A | 7/1991 | White |
| 5,061,270 A * | 10/1991 | Aboczky .................... 606/91 |
| 5,067,961 A | 11/1991 | Kelman et al. |
| 5,087,392 A | 2/1992 | Burke et al. |
| 5,094,876 A | 3/1992 | Goldberg et al. |
| 5,100,689 A | 3/1992 | Goldberg et al. |
| 5,112,350 A | 5/1992 | Civerchia et al. |
| 5,115,056 A | 5/1992 | Mueller et al. |
| 5,122,133 A | 6/1992 | Evans |
| 5,133,769 A | 7/1992 | Wagner et al. |
| 5,171,318 A | 12/1992 | Gibson et al. |
| 5,258,024 A | 11/1993 | Chavel et al. |
| 5,264,495 A | 11/1993 | Irie et al. |
| 5,276,070 A | 1/1994 | Arroyo |
| 5,282,851 A | 2/1994 | Jacob-LaBarre |
| 5,290,548 A | 3/1994 | Goldberg |
| 5,300,116 A | 4/1994 | Chirila et al. |
| 5,314,478 A | 5/1994 | Oka et al. |
| 5,374,515 A | 12/1994 | Parenteau et al. |
| 5,403,893 A | 4/1995 | Tanaka et al. |
| 5,476,515 A | 12/1995 | Kelman |
| 5,556,429 A | 9/1996 | Felt |
| 5,562,738 A | 10/1996 | Boyd et al. |
| 5,589,563 A | 12/1996 | Ward |
| 5,591,170 A | 1/1997 | Spievack et al. |
| 5,643,390 A | 7/1997 | Don et al. |
| 5,644,049 A | 7/1997 | Giusti et al. |
| 5,645,592 A | 7/1997 | Nicolais et al. |
| 5,656,210 A | 8/1997 | Hill et al. |
| 5,660,692 A | 8/1997 | Nesburn et al. |
| 5,674,942 A | 10/1997 | Hill et al. |
| 5,693,034 A | 12/1997 | Buscemi et al. |
| 5,716,633 A | 2/1998 | Civerchia |
| 5,763,529 A | 6/1998 | Lucas |
| 5,770,669 A | 6/1998 | Robertson et al. |
| 5,800,412 A | 9/1998 | Zhang et al. |
| 5,824,079 A | 10/1998 | Siegler et al. |
| 5,836,313 A | 11/1998 | Perez et al. |
| 5,856,366 A | 1/1999 | Shiveley et al. |
| 5,904,927 A | 5/1999 | Amiji |
| 5,913,858 A | 6/1999 | Calandruccio et al. |
| 5,962,005 A | 10/1999 | Saga et al. |
| 5,976,648 A | 11/1999 | Li et al. |
| 6,001,894 A | 12/1999 | Ottersbach et al. |
| 6,005,160 A | 12/1999 | Hsiue et al. |
| 6,027,742 A | 2/2000 | Lee et al. |
| 6,031,017 A | 2/2000 | Waki et al. |
| 6,057,406 A | 5/2000 | Pojman et al. |
| 6,120,904 A | 9/2000 | Hostettler et al. |
| 6,160,084 A | 12/2000 | Langer et al. |
| 6,171,300 B1 | 1/2001 | Adams |
| 6,210,438 B1 | 4/2001 | Sheets, Jr. et al. |
| 6,214,044 B1 | 4/2001 | Silverstrini |
| 6,221,467 B1 | 4/2001 | Nazarova et al. |
| 6,224,893 B1 | 5/2001 | Langer et al. |
| 6,231,605 B1 | 5/2001 | Ku |
| 6,231,611 B1 | 5/2001 | Mosseri |
| 6,239,209 B1 | 5/2001 | Yang et al. |
| 6,251,965 B1 | 6/2001 | Wang et al. |
| 6,254,637 B1 | 7/2001 | Lee et al. |
| 6,264,695 B1 | 7/2001 | Stoy |
| 6,265,016 B1 | 7/2001 | Hostettler et al. |
| 6,281,271 B1 | 8/2001 | Rumphorst et al. |
| 6,306,177 B1 | 10/2001 | Felt et al. |
| 6,331,578 B1 | 12/2001 | Turner et al. |
| 6,372,815 B1 | 4/2002 | Sulc et al. |
| 6,376,742 B1 | 4/2002 | Zdrahala et al. |
| 6,388,043 B1 | 5/2002 | Langer et al. |
| 6,391,055 B1 | 5/2002 | Ikada et al. |
| 6,428,576 B1 | 8/2002 | Haldimann |
| 6,437,018 B1 | 8/2002 | Gertzman et al. |
| 6,440,444 B2 | 8/2002 | Boyce et al. |
| 6,479,565 B1 | 11/2002 | Stanley |
| 6,482,209 B1 | 11/2002 | Engh et al. |
| 6,494,917 B1 | 12/2002 | McKellop et al. |
| 6,509,098 B1 | 1/2003 | Merrill et al. |
| 6,585,771 B1 * | 7/2003 | Buttermilch et al. ...... 623/22.12 |
| 6,610,067 B2 | 8/2003 | Tallarida et al. |
| 6,629,997 B2 | 10/2003 | Mansmann |
| 6,632,235 B2 | 10/2003 | Weikel et al. |
| 6,632,246 B1 | 10/2003 | Simon et al. |
| 6,645,715 B1 | 11/2003 | Griffith et al. |
| 6,652,587 B2 | 11/2003 | Felt et al. |
| 6,673,079 B1 | 1/2004 | Kane |
| 6,673,112 B2 | 1/2004 | Nigam |
| 6,679,917 B2 | 1/2004 | Ek |
| 6,689,165 B2 | 2/2004 | Jacob et al. |
| 6,726,322 B2 | 4/2004 | Andino et al. |
| 6,733,533 B1 | 5/2004 | Lozier |

(56) References Cited

U.S. PATENT DOCUMENTS

| | | |
|---|---|---|
| 6,740,087 B2 | 5/2004 | Knox |
| 6,755,865 B2 | 6/2004 | Tarabishy |
| 6,846,875 B2 | 1/2005 | Pennings et al. |
| 6,852,125 B2 | 2/2005 | Simon et al. |
| 6,866,936 B2 | 3/2005 | Opolski |
| 6,911,212 B2 | 6/2005 | Gertzman et al. |
| 6,918,914 B2 | 7/2005 | Bauer |
| 6,921,264 B2 | 7/2005 | Mayer et al. |
| 6,949,251 B2 | 9/2005 | Dalal et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,235,592 B2 | 6/2007 | Muratoglu et al. |
| 7,279,174 B2 | 10/2007 | Pacetti et al. |
| 7,279,507 B2 | 10/2007 | Hu et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,678,151 B2 | 3/2010 | Ek |
| 7,713,305 B2 | 5/2010 | Ek |
| 7,824,666 B2 | 11/2010 | Wolff et al. |
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0022216 A1 | 1/2003 | Mao et al. |
| 2003/0083389 A1 | 5/2003 | Kao et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0187146 A1 | 8/2005 | Helmus et al. |
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde, Jr. |
| 2005/0267584 A1 | 12/2005 | Burdulis, Jr. et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | De Sousa et al. |
| 2006/0052878 A1 | 3/2006 | Schmieding |
| 2006/0083773 A1 | 4/2006 | Myung et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0188487 A1 | 8/2006 | Thomas et al. |
| 2006/0188940 A1 | 8/2006 | Cima et al. |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235542 A1 | 10/2006 | Hodorek et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde, Jr. et al. |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |

(56) References Cited

U.S. PATENT DOCUMENTS

| | | | |
|---|---|---|---|
| 2007/0270783 A1 | 11/2007 | Zumsteg et al. | |
| 2007/0276394 A1 | 11/2007 | Johnson et al. | |
| 2008/0058954 A1 | 3/2008 | Trieu | |
| 2008/0070086 A1 | 3/2008 | Fukuchi et al. | |
| 2008/0077249 A1 | 3/2008 | Gradel | |
| 2008/0124376 A1 | 5/2008 | Pruitt et al. | |
| 2008/0241214 A1 | 10/2008 | Myung et al. | |
| 2008/0269370 A1 | 10/2008 | Myung et al. | |
| 2008/0317818 A1 | 12/2008 | Griffith et al. | |
| 2009/0035344 A1 | 2/2009 | Thomas et al. | |
| 2009/0062408 A1 | 3/2009 | Liu et al. | |
| 2009/0062423 A1 | 3/2009 | Betz et al. | |
| 2009/0088846 A1 | 4/2009 | Myung et al. | |
| 2009/0142508 A1 | 6/2009 | Lai | |
| 2009/0163860 A1 | 6/2009 | Patrick et al. | |
| 2009/0176891 A1 | 7/2009 | Chogle et al. | |
| 2009/0209966 A1 | 8/2009 | Chandler | |
| 2009/0221730 A1 | 9/2009 | Kowalski et al. | |
| 2009/0233887 A1 | 9/2009 | Shalaby et al. | |
| 2009/0240337 A1 | 9/2009 | Myung et al. | |
| 2010/0010114 A1* | 1/2010 | Myung et al. | 523/114 |
| 2010/0032090 A1 | 2/2010 | Myung et al. | |
| 2010/0056646 A1 | 3/2010 | Shalaby et al. | |
| 2010/0125341 A1 | 5/2010 | Frauens | |
| 2011/0152868 A1 | 6/2011 | Kourtis et al. | |
| 2012/0045651 A1 | 2/2012 | Myung et al. | |
| 2012/0209396 A1 | 8/2012 | Myung et al. | |
| 2012/0232657 A1 | 9/2012 | Myung et al. | |
| 2012/0277807 A1 | 11/2012 | Myung et al. | |
| 2013/0096691 A1 | 4/2013 | Myung et al. | |

FOREIGN PATENT DOCUMENTS

| | | |
|---|---|---|
| JP | 06-287443 A | 10/1994 |
| JP | 09-077809 A | 3/1997 |
| JP | 10-500038 | 1/1998 |
| JP | 2002-514233 A | 5/2002 |
| JP | 2002-518564 A | 6/2002 |
| JP | 2002-518565 A | 6/2002 |
| JP | 2003-171475 A | 6/2003 |
| WO | WO 94/01468 A1 | 1/1994 |
| WO | WO 00/02937 A1 | 1/2000 |
| WO | WO 00/43050 A1 | 7/2000 |
| WO | WO02/26848 A2 | 4/2002 |
| WO | WO 2004/055057 A1 | 7/2004 |
| WO | WO 2004/091685 A2 | 10/2004 |
| WO | WO 2007/067697 A2 | 6/2007 |
| WO | WO 2007/112305 A2 | 10/2007 |
| WO | WO 2009/071937 A1 | 6/2009 |
| WO | WO2010/037685 | 4/2010 |
| WO | WO 2010/059495 A2 | 5/2010 |

OTHER PUBLICATIONS

Causton et al.; Dental materials: 1981 literature review Part 1; Journal of Dentistry; vol. 12; Issue 1; pp. 1R28; Mar. 1984.

Charnley, J.; Anchorage of the femoral head prosthesis to the shaft of the femur; J Bone Joint Surg Br.; 42-B:28-30; Feb. 1960.

Kanie et al.; Flexural properties of ethyl or methyl methacrylate-UDMA blend polymers; Dent Mater J; 29(5); pp. 575-581; Oct. 2010.

Morgan et al.; Dependence of yield strain of human trabecular bone on anatomic site; J Biomech.; 34(5):569-77; May 2001.

Myung et al.; U.S. Appl. No. 13/748,573 entitled "Hydrophilic Interpenetrating Polymer Networks Derived From Hydrophobic Polymers," filed Jan. 23, 2013.

Myung et al.; U.S. Appl. No. 13/748,576 entitled "Hydrophilic Interpenetrating Polymer Networks Derived From Hydrophobic Polymers," filed Jan. 23, 2013.

Myung et al.; U.S. Appl. No. 13/816,537 entitled "Hydrophobic and Hydrophilic Interpenetrating Polymer Networks Derived From Hydrophobic Polymers and Methods of Preparing the Same," filed Apr. 24, 2013.

Bobyn et al., The optimum pore size for the fixation of porous-surfaced metal implants by the ingrowth of bone. Clin Orthop Relat Res, Jul./Aug. 1980(150): p. 263-270.

Borden et al.; The sintered microsphere matrix for bone tissue engineering: In vitroosteoconductivity studies; J. Biomed. Mat. Res.; 61(3); pp. 421-429; Sep. 2002.

Brodbeck et al., Biomaterial adherent macrophage apoptosis is increased by hydrophilic and anionic substrates in vivo. Proc Natl Acad Sci U S A, Aug. 6, 2002. 99(16): p. 10287-10292.

Brown et al.; Solvent/Non-solvent sintering: A novel route to create porous microsphere scaffolds for tissue regeneration; J. Biomed. Mat. Res. (Part B: Applied Biomaterials); 86B(2); pp. 396-406; Aug. 2008.

Covert et al.; Friction characteristics of a potential articular cartilage biomaterial. Wear, Aug. 2003. 255: p. 1064-1068.

Depuy Orthopaedics; Bone Cement Time Setting Chart; product file; date of publication unknown; available to applicants at least as of Jul. 2012.

Dror et al.; Gradient interpenetrating polymer networks. I. Poly(ether urethane) and polyacrylamide IPN; J of Applied Polymer Science; 26; pp. 1741-1757; Jun. 1981.

Elmer's Products Inc.; Material Safety Data Sheet; "Elmer's Nano Glue"; Jun. 13, 2007.

Elsabee et al.; Gradient interpenetrating polymer networks. II. Polyacrylamide gradients in poly(ether urethane); J of Applied Polymer Science; 28(7); pp. 2151-2166; Jun. 1983.

Evans et al.; The use of corneal organ culture in biocompatibility studies; Biomaterials; vol. 23; pp. 1359-1367; Mar. 2002.

Frank, Curt; Structure-property relationships for hydrogels with applications to biomedical devices; Presentation at American Chemical Society Mtg; San Francisco, CA; Sep. 11, 2006.

Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.

Gong et al.; Double-network hydrogels with extremely high mechanical strength; Adv. Mater.; vol. 15; No. 14; pp. 1155-1158; Jul. 17, 2003.

Gorna et al.; Preparation, degradation, and clarification of biodegradable polyurethane foams for bone graft substitutes; J. Biomed Mater Res A; 67(3); pp. 813-827; Dec. 1, 2003.

Guelcher et al.; Synthesis and in vitro biocompatibility of injectable polyurethane foam scaffolds; Tissue Engineering; 12(5); pp. 1247-1259; May 2006.

Guelcher et al.; Synthesis of biocompatible segmented polyurethanes from aliphatic diisocyanates and diurea diol chain extenders; Acta biomaterialia; 1(4); pp. 471-484; Jul. 2005.

Gunatillake et al.; Designing biostable polyurethane elastomers for biomedical implants; Aust. J. Chem.; vol. 56; pp. 545-557; Jun. 2003.

Hern et al.; Incorporation of adhesion peptides into nonadhesive hydrogels useful for tissue resurfacing; J. Biomed. Materials Research; vol. 39; No. 1; pp. 266-276; Feb. 1998.

Iwasaki et al., Hydrogel like elastic membrane consisting of semi-interpenetrating polymer networks based on a phosphorylcholine polymer and a segmented polyurethane; J. Polym. Sci Part A: Polym Chem; 41; pp. 68-75; Jan. 2003.

Khan et al.; Analysis and evaluation of a biomedical polycarbonate urethane tested in an in vitro study and an ovine arthroplasty model. Part I: materials selection and evaluation. Biomaterials, Feb. 2005. 26(6): p. 621-631.

Kim et al.; Water sorption of ploy(propylene glycol)/poly(acrylic acid) interpenetrating polymer network hydrogels; Reactive & Functional Polymers; vol. 55; pp. 69-73; Feb. 2003.

Kim et al.; Electrochemical behavior of an interpenetrating polymer network hydrogel composed of poly(propylene glycol) and poly(acrylic acid); Journal of Applied Polymer Science; vol. 89; pp. 2301-2305; Aug. 2003.

Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.

(56) References Cited

OTHER PUBLICATIONS

Kwong et al.; A comparison of the shrinkage of commercial bone cements when mixed under vacuum; J Bone Joint Surg Br.; 88(1):120-2; Jan. 2006.
Lamba et al.; Polyurethanes in Biomedical Application; CRC Press; pp. 11, 14, 16, 18-20, 57-59, 73, 79 & 104; Nov. 1997.
Lee et al.; Interpenetrating polymer network hydrogels based on poly (ethylene glycol) macromer and chitosan; Carbohydrate Polymer; vol. 41; No. 2; pp. 197-205; Feb. 2000.
Lipatov et al.; Gradient interpenetrating polymer networks; Journal of Materials Science; 30(4); pp. 1095-1104; Feb. 1995.
Lu et al.; Release behavior of high molecular weight solutes from poly(ethylene glycol)-based degradable networks; Macromolecules; vol. 33(7); pp. 2509-2515; Mar. 2000.
Maroudas et al.; Permeability of articular cartilage; Nature; vol. 219(5160); pp. 1260-1261; Sep. 21, 1968.
Mow et al., Basic Orthopaedic Biomechanics and Mechano-Biology, Lippincot Williams and Wilkins, 3rd Edition, Apr. 2005, pp. 459-461.
Myung, David; Structure, properties, and medical device applications of mechanically enhanced, biometric hydrogel alloys; Doctoral Thesis; Stanford University; Dec. 2007.
Myung et al.; Biomimetic strain hardening in interpenetrating polymer network hydrogels; Polymer, ; vol. 48; No. 18; pp. 5376-5387; Jun. 2007.
Orr et al.; Shrinkage stresses in bone cement; Biomaterials; 24 (17):2933-40; Aug. 2003.
Park et al.; Synthesis of PVA/PVP hydrogels having two-layer by radiation and their physical properties; Radiation Physics and Chemistry; 67(3-4); pp. 361-365; Jun. 2003.
Puska et al.; Exothermal Characteristics and Release of Residual Monomers from Fiber-reinforced Oligomer-modified Acrylic Bone Cement; J Biomat App; 20:51-64; Jul. 2005.
Saito et al.; Preparation and properties of transparent cellulose hydrogels; J. Applied Polymer Science; 90(11); pp. 3020-3025; Dec. 2003.
Scholes et al.; Compliant layer acetabular cups: friction tsting of a range of materials and designs for a new generation of prosthesis that mimics the natural joint; Proc. IMechE; vol. 220(5); Part H; J. Engineering in Medicine; pp. 583-596, Jul. 2006.
Shalaby; U.S. Appl No. 61/069,046 entitled "Hydroswellable, segmented, aliphatic polyurethanes and polyurethane ureas," filed Mar. 12, 2008.
Spector et al.; Porous polymers for biological fixation. Clin Orthop Relat Res, Oct. 1988 (235): p. 207-219.
Stammen et al., Mechanical properties of a novel PVA hydrogel in shear and unconfined compression. Biomaterials, Apr. 2001. 22(8): p. 799-806.
Stryker Orthopaedics; SimplexTM P Bone Cement; Product Literature LSB Rev. 3, Mar. 2006.
Tariq et al.; (Abstract) Sodium benzoate attenuates iminodipropionitrile-induced behavioral syndrome in rats. Behav pharmacol; Dec. 2004.
Tawfik, Dan; Amidation of carboxyl groups; The Protein Protocols Handbook, 2nd Ed.; Humana Press; pp. 477-478; Feb. 2002.
The Engineering Toolbox; Polyurethane insulation: {http://www.engineeringtoolbox.com/polyurethane-insulation-k-values-d_1174.html} pp. 1-3; printed Oct. 21, 2011.
The Engineering Toolbox;Thermal conductivity of some common materials and gases: {http://www.engineeringtoolbox.com/thrmal-conductivity-d_429.html} pp. 1-2; printed Oct. 21, 2011.
The Gorilla Glue Company; Material Safety Data Sheet; "New Fast Cure-Dries White Gorilla Glue®"; Jan. 30, 2007.
The Gorilla Glue Company; Material Safety Data Sheet; "New Stronger-Faster Gorilla Glue®"; Jan. 26, 2007.
Wittemann et al.; Adsorption of proteins on spherical polyelectrolyte brushes in aqueous solution; Phys. Chem. Chem. Phys., Mar. 2003, vol. 5(8), pp. 1671-1677.
Wright et al., Wear studies on prosthetic materials using the pin-on-disc machine. Biomaterials, vol. 3, Issue 1, Jan. 1982, pp. 41R48.
Yang et al.; Preparation of poly(acrylic acid) modified polyurethane membrane for biomaterial by UV radiation without degassing; J. Biomed. Mater. Res.; vol. 45(2); pp. 133-139; May 1999.
Yim et al., Biocompatibility of poly(ethylene glycol)/poly(acrylic acid)interpenetrating polymer network hydrogel particles inRAW 264.7 macrophage and MG-63 osteoblast cell lines. Journal of Biomedical Materials Research, 91A(3); pp. 894-902; Dec. 1, 2009.
Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.
Kourtis et al.: U.S. Appl. No. 13/573,788 entitled "Polymeric adhesive for anchoring compliant materials to another surface," filed Oct. 3, 2012.
Barszczewska-Rybarek, Izabela M.; Quantitative determination of degree of conversion in photocured poly(urethane-dimethacrylate)s by Fourier transform infrared spectroscopy; Journal of Applied Polymer Science; vol. 123; issue 3; pp. 1604-1611; Feb. 5, 2012.
Lewis G.; Properties of acrylic bone cement: state of the art review; J Biomed Mater Res.; 38(2):155-82; Summer(Jun.-Aug.) 1997.
Ohman et al.; Mechanical testing of cancellous bone from the femoral head: experimental errors due to off-axis measurements; J Biomech.; 40(11):2426-33; (year of publication is sufficiently earlier than the effective U.S. filing date and any foreign priority date) 2007.

* cited by examiner

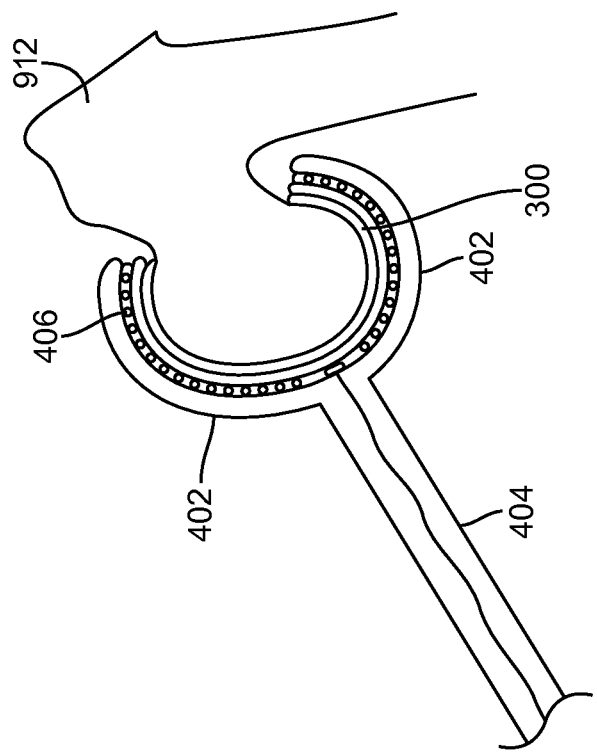
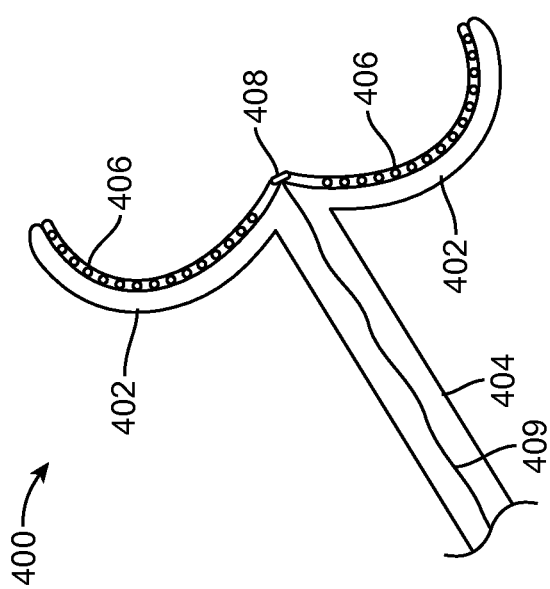

| Company Name | Product Name | Application | Active Ingredient (pre cured) |
|---|---|---|---|
| Heraeus Dental | iBond Total Etch | Dental Adhesive Cement | UDMA |
| Dentsply International | SmartCem2 | Dental Adhesive Cement | UDMA, Acrylated Esters of Phosphoric Acid |
| Ivoclar vivadent | Tetric EvoFlow | Dental Adhesive Cement | UDMA, Bis-GMA |
| PulpDent | Lime-Lite | Dental cavity liner | UDMA, Hydroxyapatite |
| Stryker | Simplex P | Orthopedic Bone Cement | MMA, MMA-Styrene Copolymer |
| Zimmer | Palacos | Orthopedic Bone Cement | MMA-Methyl Acrylate Copolymer |
| DePuy | CMW | Orthopedic Bone Cement | PMMA |

FIG. 62A

| Components | (w/w) | Commercial product that contains constituent |
|---|---|---|
| Urethane Dimethacrylate (UDMA) | 60%-80% | iBond, SmartCem2, Tetric EvoFlow, Lime-Lite |
| Methyl Methacrylate (MMA) | 20%-40% | Simplex P, Palacos R, CMW |
| Camphorquinone (initiator) | <1% | iBond, SmartCem2, Tetric EvoFlow, Lime-Lite |
| Benzoyl Peroxide (initiator) | <1% | Simplex P, Palacos R, CMW |
| N,N-dimethyl-p-toluidine (accelerator) | <1% | Simplex P, Palacos R, CMW |
| Hydroquinone (inhibitor) | 0.1% | Simplex P, Palacos R, CMW |

FIG. 62B

SYSTEMS, DEVICES, AND METHODS FOR ANCHORING ORTHOPAEDIC IMPLANTS TO BONE

CROSS REFERENCE TO RELATED APPLICATIONS

This application claims the benefit of U.S. Provisional Patent Application No. 61/562,187 filed Nov. 21, 2011, U.S. Provisional Patent Application No. 61/566,558 filed Dec. 2, 2011, and Provisional Patent Application No. 61/566,567 filed Dec. 2, 2011; all of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention includes devices, systems, and methods for delivering an implant and attaching it to a joint. The system may include a container for a flexible implant and/or a separate shaper with an attachment portion connectable to a delivery tool for attaching the implant to a bone surface and dictating its final shape after attachment is complete. The system may also include a light delivery instrument for curing an adhesive on a surface of the implant to anchor the implant to a bone surface.

BACKGROUND

A large number of patients undergo joint replacement surgery each year. An estimated 540,000 patients in the U.S. undergo knee arthroplasty annually. Currently, implants made from metal, ceramic and/or ultra-high molecular weight polyethylene (UHMWPE) have been used in orthopedic joint arthroplasty or joint replacement. However, the use of such materials often necessitates high degree of bone and soft tissue sacrifice. For example, for hip replacement the femoral head is often entirely removed and replaced with a metal ball and stem implant. This results in the introduction of greater amounts of implant material into the patient's body which can corrode or may release ions or debris, such as metal ions or wear particles. The ions or particles may remain in the joint area or may travel through the blood to other parts of the body. The implant or the debris or ions it releases may cause bone resorption (osteolysis), inflammation, metal toxicity, pseudo-tumors, pain, and other problems.

As such, flexible polymer implants have been designed as medical implants for adhesion to bone and bone-like structures or surfaces. Some such implants have been designed to replace the current materials for joint replacement. For example, a compliant polymer material can be used as cartilage replacement, which provides a bone sparing alternative to implants made from traditional materials, e.g. ceramic, metal, polyethylene. Artificial cartilage implants can be formed with a lubricious bearing (articulating) surface for replacing cartilage and an attachment surface for fixation of the implant to bone for any joint in the body. In some cases, a hydrated polymer (e.g. hydrogel) material is used for forming the compliant polymer implant. Additionally, these flexible polymeric implants may contain a homopolymer, copolymer, or a fully interpenetrating polymer network (IPN's) and/or semi-interpenetrating polymer network ("semi-IPN's"). Polymer implants may also include accessible chemical functional groups such as amine, hydroxyl, carboxyl, or urethane groups, or combinations of functional groups that can be used to modify the characteristics of the implants. Examples of polymeric materials and implants containing these materials are more fully described in: U.S. application Ser. No. 12/499,041 filed Jul. 7, 2009; U.S. application Ser. No. 13/219,348 filed Aug. 26, 2011; U.S. application Ser. No. 13/347,647 filed Jan. 10, 2012; U.S. application Ser. No. 12/536,233 filed Aug. 5, 2009; Ser. No. 12/148,534 filed Apr. 17, 2008; U.S. application Ser. No. 13/418,294 filed Mar. 12, 2012; International Application No. PCT/US11/4936 filed Mar. 23, 2009; and International Application No. PCT/US12/20828 filed Jan. 10, 2012, which are all incorporated by reference in their entirety.

Another advantage of using polymeric material is the ability to create desirable mechanical properties in an implant. Implants can be created with high mechanical strength and wear-resistance while at the same time providing lubricity. This is particularly advantageous for joint implants where a polymer implant can be implanted on one side of a joint forming a polymer-on-cartilage articulation in the joint. The bone-facing side of the polymer implant can be designed to include a polymeric material providing strength and wear-resistance while the articulation side of the same implant has a hydrated polymer that provides lubricity. Additionally, a joint may include multiple implanted polymer devices where one device mates with another in articulation. Each polymer implant is affixed to respective bone surfaces in the joint and mate in a polymer-on-polymer articulation. The structure and polymeric composition of the implants ensure strength at the bone-facing sides and low friction at the articulation sides.

Although the versatility of polymeric materials has several advantages, one challenge is the difficulty in maintaining the shape and form of a compliant, flexible implant. Unlike metal counterparts, the shape of flexible polymeric materials can bend, distort, or change more easily due to the implant's environment. This is problematic where an unused implant changes shape during storage and is no longer viable for implantation when needed. Furthermore, shape changes during the implantation procedure are potentially dangerous where the form of the implant alters during or after the anchoring process. As such, there is a need for maintaining the desired shape or form of the implant prior to, during, and after delivery and implantation into a patient's body.

In addition to the above, another challenge with a flexible implant is the ability to properly position and affix the implant to a target location. Implants are commonly anchored to a bone or joint space by way of a curable adhesive or cement. Conventional adhesives or cements contain polymethylmethacrylate and involve the curing of the compound into a grout-like material where the adhesive interdigitates with features on the implant (such as grooves) to secure the implant to a surface. Other mechanisms of affixation also include chemical and/or physical adhesion, e.g., covalent bonds formed between reactive functional groups found on the device material or bone and the chemical groups in the adhesive polymer and/or a variety of non-covalent interactions such as absorption (e.g., chemisorption, physisorption), hydrophobic interaction, crystallite formation, hydrogen bonds, pi-bond stacking, van der Waals interactions and physical entanglements between the device and the cured adhesive copolymer (e.g., at the molecular level), mechanical interlocking. Physical adhesion may be the result of in-filling or interdigitating of a bump(s), a depression(s), a groove(s), a pore(s), a rough area(s), a space(s) and/or other surface features. Examples of adhesive compounds that can be used to anchor a flexible polymer implant include those described in: U.S. application Ser. No. 12/409,359 filed Mar. 23, 2009; U.S. application Ser. No. 13/542,464 filed Jul. 5, 2012; and U.S. application Ser. No. 13/573,788 filed Oct. 3, 2012, which are all incorporated by reference in their entirety.

Generally, such adhesive compounds are applied to a surface of the implant in an uncured form. Then when thermal, chemical, or light-curing is applied to the implant surface, the implant is affixed to the joint surface. A problem that arises with polymer implants is the need to adjust the position or shape of the implant during the curing process.

To address these challenges, embodiments described herein provide methods, devices, and systems that facilitate the delivery and attachment of a flexible implant to a bone or bone-like surface. Embodiments described allow an implant to be easily, quickly, and strongly attached to a bone surface with a desired implant shape. Some embodiments may deliver any implant to a bone joint surface, but may be especially useful for delivering and attaching a flexible polymer implant to a bone joint surface. In some examples, the devices and methods may allow an implant to conform to a shape, including an irregular shape, of a bone surface, thereby providing a better fit between the implant and the bone surface.

Embodiments described also provide for methods and devices that can be used to control the curing rate of the adhesive compound to allow repositioning or reshaping of the implant. For example, a user (e.g. physician) may be able to control the start of the attachment procedure such as curing (e.g. curing may be started only after the implant is properly placed in a joint) by using a delivery device with a curing rate feature. Once curing of an adhesive to hold an implant in place is started, then the process may proceed very quickly, reducing the possibility that an implant might move out of position before curing and implant attachment is completed. Moreover, embodiments described provide methods and devices that maintain or mold the shape of the implant during curing to ensure proper fixation. For example, shaping devices are provided to maintain, support, or conform the shape of the implant during adhesion to a joint surface.

Additionally, although embodiments may provide for flexible or compliant implants, the devices, methods, and systems described herein can also be used with an implant having a relatively stiff or rigid structure.

SUMMARY OF THE DISCLOSURE

In one aspect, embodiments described relate to an orthopedic implant delivery system including a container having a first component adapted to surround and contain an implant when mated to a second component, the second component adapted to hold the orthopedic implant; and a delivery instrument configured for inserting an orthopedic implant into a joint of a patient, the delivery instrument including a connector for releasably attaching to the second component of the container and a gripping member sized and configured to allow manipulation of the delivery instrument and attached implant to the joint.

In any of the preceding embodiments, the delivery instrument may be a light delivery instrument having a light source and a light applicator adapted to transmit light from the light source to an orthopedic implant held by the second component of the container attached to the connector.

In any of the preceding embodiments, the light applicator can be further adapted to transmit light to the implant through the second component of the container attached to the connector. In any of the preceding embodiments, the light source can be configured to emit light suitable for curing a light-curable compound. In any of the preceding embodiments, the gripping member can be a handle positioned along a lateral axis of the light delivery instrument.

In any of the preceding embodiments, the light delivery instrument includes a lightguide cable connecting the light applicator to the light source. In any of the preceding embodiments, the light delivery instrument can include a self-contained power source. In any of the preceding embodiments, the light source can include at least one LED or LED array. In any of the preceding embodiments, the second component further includes a light diffuser.

In any of the preceding embodiments, the first and second components are configured to mate through a threaded interface. In any of the preceding embodiments, the first and second components are configured to mate through a vacuum suction interface.

In any of the preceding embodiments, the second component of the container includes a lid. In any of the preceding embodiments, the second component of the container includes a lid and an implant shaper.

In any of the preceding embodiments, the implant shaper can be adapted to hold an implant while maintaining the implant's shape. In any of the preceding embodiments, the implant shaper can be adapted protect an implant surface.

In any of the preceding embodiments, the second component of the container includes a convex spherical surface, the convex spherical surface adapted to engage a concave inner surface of an implant to hold the implant. In any of the preceding embodiments, the second component of the container has a cross-sectional diameter between about 38 mm to about 60 mm. In any of the preceding embodiments, the cross-sectional diameter may be between about 30 mm and about 60 mm.

In any of the preceding embodiments, the first and second components include indentations along a perimeter of an outer surface.

In any of the preceding embodiments, the container can be transparent. In any of the preceding embodiments, the second component can be sufficiently transparent to allow transmission of light through a thickness of an orthopedic implant held by the first component.

In any of the preceding embodiments, the second component permits transmission of light through a thickness of the second component to an orthopedic implant held by the second component.

In any of the preceding embodiments, the second component includes an opening adapted to engage the light applicator of the light delivery instrument.

In any of the preceding embodiments, the system further includes a light-curable compound applied to a surface of an implant held by the second component of the container.

In any of the preceding embodiments, the system includes an orthopedic implant inside the implant container. In any of the preceding embodiments, the implant container can be adapted to enclose an acetabulum implant. In any of the preceding embodiments, the implant container can be adapted to enclose a femoral implant.

In another aspect, embodiments described provide an orthopedic implant delivery system having a container having a first component adapted to contain an orthopedic implant, a second component adapted to mate with the first component to surround and contain the implant, and a third component adapted to hold and maintain a shape of the implant while the implant is contained; a delivery instrument configured for inserting an orthopedic implant into a joint of a patient, the delivery instrument including a gripping member sized and configured to allow manipulation of the delivery instrument.

In any of the preceding embodiments, the delivery instrument is a light delivery instrument having a light source and a light applicator adapted to transmit light from the light source to an orthopedic implant held by the third component of the container.

In any of the preceding embodiments, the third component is adapted to mate with the first and second components to surround and contain the implant. In any of the preceding embodiments, the third component includes a concave inner surface that can be adapted to contact an outer convex surface of an implant held by the third component. In any of the preceding embodiments, the third component is sufficiently transparent to allow transmission of light through a thickness of an orthopedic implant held by the third component. In any of the preceding embodiments, the third component includes a generally spherical shell having a radially expandable diameter. In any of the preceding embodiments, the third component includes resilient expandable members.

In any of the preceding embodiments, the system including a light-curable adhesive on a surface of an implant held in the third component of the container.

In any of the preceding embodiments, the third component of the container can be removable from the container when holding an implant.

In any of the preceding embodiments, the system including a form mold adapted to surround a portion of the third component of the container, wherein the form mold maintains the shape of the third component and the implant when the third component is separated from the container.

In any of the preceding embodiments, the system includes a joint space sizer adapted to be inserted into the joint.

In any of the preceding embodiments, the system includes a curable compound spreading device.

In any of the preceding embodiments, the implant container can be adapted to enclose a portion of the femoral head.

In any of the preceding embodiments, the light applicator includes two opposing arms, the opposing arms configured to rotate about a pivot point positioned on a longitudinal axis of the device. In any of the preceding embodiments, the light applicator includes a plurality of light emitting elements along a surface of each opposing arm. In any of the preceding embodiments, the opposing arms have an open configuration and a closed configuration. In any of the preceding embodiments, the opposing arms in the closed configuration form a substantially circular arc having an angle larger than about 180 degrees. In any of the preceding embodiments, the substantially circular arc has an angle between about 180 degrees and 270 degrees.

In any of the preceding embodiments, the light emitting end of the light applicator has a shape selected from the group consisting of a convex shape, a concave shape, a flat shape, and a wedge shape. In any of the preceding embodiments, the light emitting end has a plurality of light emitting elements.

In any of the preceding embodiments, the light applicator has a cross-sectional diameter between about 30 mm to about 60 mm.

In another aspect, some embodiments provide for an implant container having a first component adapted to receive an implant; a second component comprising a first surface configured to engage and hold the implant, wherein the first component attaches to the second component to enclose the implant; and a second surface on the container configured to attach a delivery tool, wherein the delivery tool assists attachment of the implant to a joint.

In any of the preceding embodiments, the delivery tool is a light delivery instrument. In any of the preceding embodiments, the second surface transmits light from the light delivery instrument through a thickness of the container to a surface of the implant.

In any of the preceding embodiments, the delivery tool is an adhesive spreading device.

In any of the preceding embodiments, the second component includes a spherical protrusion adapted to engage a concave surface of the implant, the spherical protrusion configured to hold the implant onto the second component while maintaining the shape of the implant when held. In any of the preceding embodiments, the second component is configured for insertion into a concave opening of the implant.

In any of the preceding embodiments, at least one portion of the second component allows transmission of light through a thickness of the second component. In any of the preceding embodiments, the second component includes a removable lid.

In any of the preceding embodiments, the second component includes a removable shaping member that maintains the shape of the implant held by the second component. In any of the preceding embodiments, the second surface is on the shaping member.

In any of the preceding embodiments, the shaping member has a north pole and an opening about the north pole.

In any of the preceding embodiments, the shaping member is radially expandable. In any of the preceding embodiments, the shaping member has an expandable opening. In any of the preceding embodiments, the shaping member includes perforations adapted to allow radial expansion of the shaping member. In any of the preceding embodiments, the shaping member includes resilient members. In any of the preceding embodiments, the shaping member has a plurality of longitudinal slots. In any of the preceding embodiments, the shaping member includes expandable segments resiliently biased toward the center of the shaping member.

In any of the preceding embodiments, the shaping member including a north pole along a longitudinal axis of the shaping member and at least one of the plurality of longitudinal slot is positioned distal of the north pole. In any of the preceding embodiments, an end of at least one of the plurality of longitudinal slots is located on a perimeter at an opening of the shaping member. In any of the preceding embodiments, the plurality of longitudinal slots has a uniform length. In any of the preceding embodiments, the plurality of longitudinal slots have at least two different lengths.

In any of the preceding embodiments, the shaping member including a concave cap with an inner surface adapted to engage an outer surface of the implant. In any of the preceding embodiments, the second component including a convex protrusion adapted to engage a concave surface of an implant, the second component configured to maintain a shape of the implant while engaged.

In another aspect, some embodiments provide for a method for curing a flexible implant in a joint space including placing a flexible implant into a joint space; maintaining a shape of the flexible implant in the joint space by attaching the flexible implant to a shaper; applying a curable compound to a surface of the implant or the joint; and adhering the implant to a surface of the joint space by polymerizing the compound.

In any of the preceding embodiments, the method for curing a flexible implant includes curing the compound to the surface of the implant by a combination of light and thermal curing.

In any of the preceding embodiments, the method for curing a flexible implant includes applying light through a thickness of the implant to initiate polymerization of the compound on the surface of the implant and into the joint space.

In any of the preceding embodiments, the method for curing a flexible implant includes providing an implant in a container including the shaper, wherein the shaper has a delivery attachment portion; coupling a delivery device to the delivery attachment portion; and delivering the implant to the surface of the joint space by manipulating the delivery device In any of the preceding embodiments, the method for curing a flexible implant includes adhering the implant to the surface of the joint space by applying light through a thickness of the container; and removing the container.

In any of the preceding embodiments, the method for curing a flexible implant includes partially curing the compound on the surface of the implant while the implant is placed against the surface in the joint space; adjusting a position of the implant while the compound is partially cured; and completing the curing of the compound after the adjustment.

In any of the preceding embodiments, the method for curing a flexible implant includes substantially maintaining the form and shape of the implant during polymerization of the compound.

In any of the preceding embodiments, the method for curing a flexible implant includes providing an implant placed in a shape sleeve; and inserting a portion of bone into a concave end of the implant while the implant is inside the shape sleeve.

In any of the preceding embodiments, the method for curing a flexible implant includes resiliently expanding the shaper during bone insertion into the implant. In any of the preceding embodiments, the method for curing a flexible implant including placing the implant over a femoral head; and radially expanding a plurality of resilient members on the shaper during placement over the femoral head.

In any of the preceding embodiments, the method for curing a flexible implant includes applying light to polymerize the compound. In any of the preceding embodiments, light is applied through a thickness of the implant discontinuously. In any of the preceding embodiments, the method for curing a flexible implant includes suspending the application of light for a period of time after partially polymerizing the compound. In any of the preceding embodiments, the method for curing a flexible implant includes controlling a rate of the polymerization by discontinuously applying the light. In any of the preceding embodiments, the method for curing a flexible implant includes varying an intensity of the light. In any of the preceding embodiments, the method for curing a flexible implant includes controlling the polymerization of the compound by varying an intensity of the light. In any of the preceding embodiments, the method for curing a flexible implant includes monitoring a temperature of the joint space during polymerization and adjusting an intensity of the light to maintain the temperature below a physiological limit. In any of the preceding embodiments, the light comprises UV light, blue light, or visible light. In any of the preceding embodiments, the light has an intensity sufficient to penetrate through a thickness of the implant.

In any of the preceding embodiments, the method for curing a flexible implant includes applying a light to form covalent bonding between the implant and the compound. In any of the preceding embodiments, the method for curing a flexible implant includes applying a light to form non-covalent bonding between the implant and the compound. In any of the preceding embodiments, the method for curing a flexible implant includes curing the compound partially onto a surface of the implant prior to placing the implant into the joint space.

In any of the preceding embodiments, the method for curing a flexible implant includes applying light through the thickness of the implant to initiate partial polymerization of the compound prior to placing the implant into the joint space. In any of the preceding embodiments, the method for curing a flexible implant includes conforming the implant to the joint space prior to polymerizing the compound. In any of the preceding embodiments, the method for curing a flexible implant includes softening the implant by dissolving, diffusing, and/or penetrating the compound into a portion of the implant.

In any of the preceding embodiments, the compound is applied to the surface of the implant prior to placing the implant into the joint space. In any of the preceding embodiments, the joint space is the acetabulum. In any of the preceding embodiments, the joint space is a portion of the femoral head. In any of the preceding embodiments, the implant is an orthopedic polymer implant comprising polyurethane. In any of the preceding embodiments, the surface of the implant comprises polyurethane.

In any of the preceding embodiments, the curable compound contains polymethylmethacrylate.

In another embodiments, some embodiments provide for a method of replacing cartilage on a joint surface with steps of shaping a surface of a joint space; providing an implant in a shape holder, wherein a surface of the implant contains an adhesive curable compound; placing the implant in the shape holder into the joint space; polymerizing the adhesive curable compound; adhering the implant to the joint surface; and removing the shape holder.

In any of the preceding embodiments, the joint surface is an acetabular surface.

In any of the preceding embodiments, the implant is placed over the shape holder and an outer surface of the implant contains the adhesive curable compound.

In any of the preceding embodiments, the method of replacing cartilage on a joint surface includes applying force to a north pole of the shape holder to substantially distribute the adhesive compound over the implant surface in contact with the joint surface.

In any of the preceding embodiments, the method of replacing cartilage on a joint surface includes applying a compressive force across an outer surface of the shape holder to substantially distribute the adhesive compound on the implant surface in contact with the joint surface.

In any of the preceding embodiments, the method of replacing cartilage on a joint surface includes confirming the sizing of the joint space after shaping the joint space.

In any of the preceding embodiments, the method of replacing cartilage on a joint surface includes negatively pressurizing the joint space to remove tissue.

In any of the preceding embodiments, the method of replacing cartilage on a joint surface includes applying the adhesive curable compound to the joint surface under positive pressure.

In another aspect, embodiments described provide for an joint space sizer having a gripping member; a elongate member; and a convex end configured for insertion into a joint space, wherein the convex end has a spherical shape with a diameter between about 38 mm and 60 mm, the convex end adapted to provide measurements on the depth and size of the joint space. In any of the preceding embodiments, the joint space sizer may be adapted to measure the orientation of the joint space. In any of the preceding embodiments, the convex end of the joint space sizer may have a diameter between about 30 mm and 60 mm.

In another aspect, some embodiments provide for an adhesive spreader including a tubular handle connected to a plunger element, the plunger element configured to move along a length of the tubular handle, wherein the plunger element comprises a diameter between about 38 mm and 60 mm and is adapted to apply an inwardly radial force when covering a spherical object. In any of the preceding embodiments, the plunger element may have a diameter between about 30 mm and 60 mm.

In another aspect, embodiments provide for an adhesive spreader having an elongate support member attached to at least one roller, wherein the roller is adapted to roll across a surface to spread a compound across the surface, the roller attached to the elongate support member by a pin. In any of the preceding embodiments, the roller can be adapted to roll across a non-flat surface.

In another aspect, some embodiments provide for a method of spreading a curable adhesive for implant attachment with the steps of applying a first force against a first implant surface about a north pole of an implant in contact with an curable compound, wherein the force is distally directed relative to the north pole; applying a second force to a second implant surface by moving a spreading device in contact with the implant from a position proximal to the north pole to a position distal of the north pole; and spreading the curable compound across a portion of the implant's surface in contact with a joint surface. Additionally, the position distal of the north pole is on an equator of the implant or on a perimeter of a distal opening of the implant.

In any of the preceding embodiments, the step of applying a second force step is repeated to spread the curable compound across substantially a majority of the implant's surface in contact with the joint space.

In any of the preceding embodiments, the method of spreading a curable adhesive for implant attachment may include a spreading device that applies force to the implant through a shaping element attached to the implant.

In another aspect, embodiments provide for a form mold with a cylindrical body having an outer surface, wherein the body is adapted to mate with an implant shaping member surround a flexible implant; and a flanged rim positioned about a circumference of the outer surface.

In a further aspect, embodiments provide for a method for curing a flexible coating in a joint space with the steps of placing a curable compound into a joint space and onto a joint surface; shaping the curable compound on the joint surface; adhering the curable compound to the joint space by polymerizing the curable compound on the joint surface; and forming a flexible joint coating on the joint surface.

In an additional aspect, embodiments provide for an orthopedic implant delivery system having a shaping element adapted to hold the orthopedic implant and support an implant shape; and a delivery instrument configured for inserting an orthopedic implant into a joint of a patient, the delivery instrument including a connector for releasably attaching to the shaping element and a gripping member sized and configured to allow manipulation of the delivery instrument and attached implant to the joint.

In another aspect, embodiments provide for a method for curing a flexible implant in a joint space with the steps of placing a flexible implant into a joint space; maintaining a shape of the flexible implant in the joint space by attaching the flexible implant to a shaper; applying a curable compound to a surface of the implant; and adhering the implant to a surface of the joint space by polymerizing the compound.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 51A-B show a device for providing light to a femoral joint region.

FIGS. 62A-B show exemplary dental adhesive cements, dental cavity liner, and orthopedic bone cements.

DETAILED DESCRIPTION

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as defined by the appended claims.

Various aspects of the inventions are directed to systems, devices, and methods for delivering and implanting an orthopedic implant. The device may be configured for use in any joint in the body, including but not limited to shoulder joint, a finger joint, a hand joint, an ankle joint, a foot joint, a toe joint, a knee compartment joint, a patellofemoral joint, a total knee joint, a knee meniscus, a hip joint, a femoral side of a hip joint, an acetabular side of a hip joint, a shoulder or hip labrum, an elbow, an intervertebral facet, or a vertebral joint.

Figure 1:
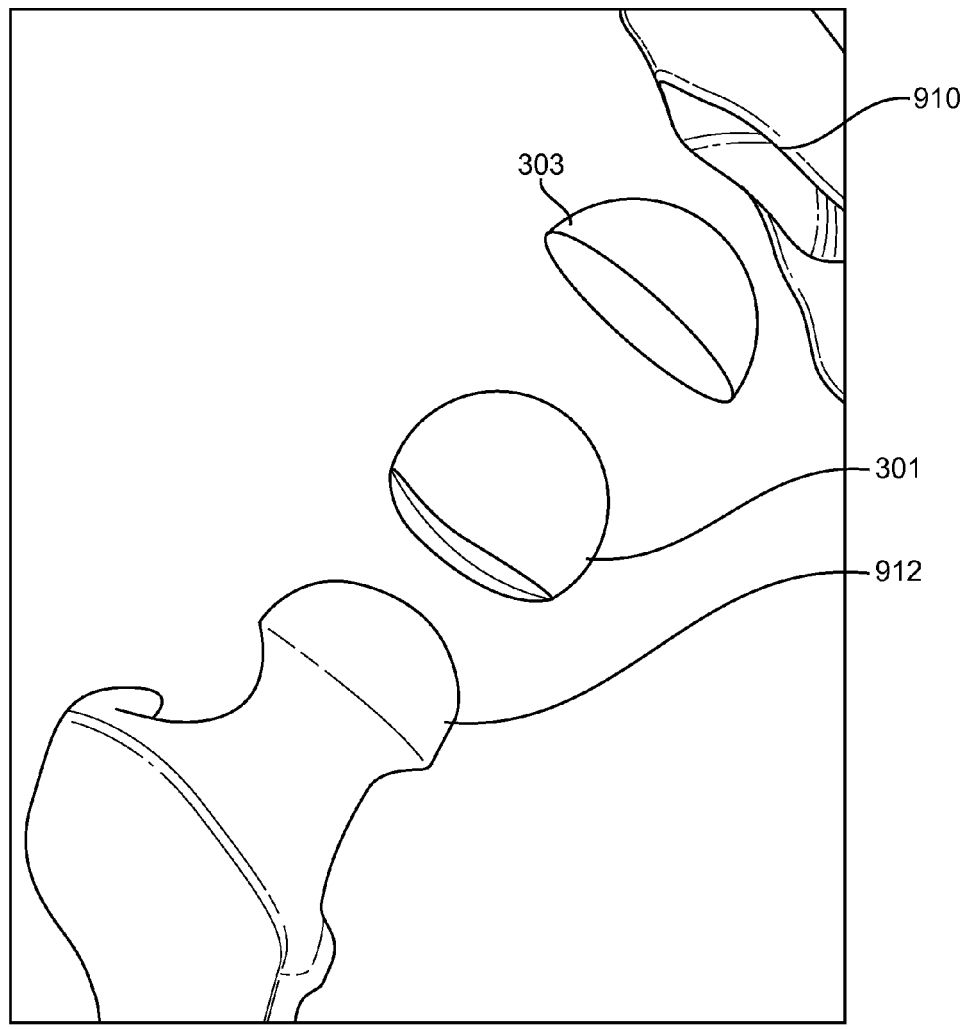
FIG. 1 shows flexible implants corresponding to the acetabulum and femoral head.
Figure 2:
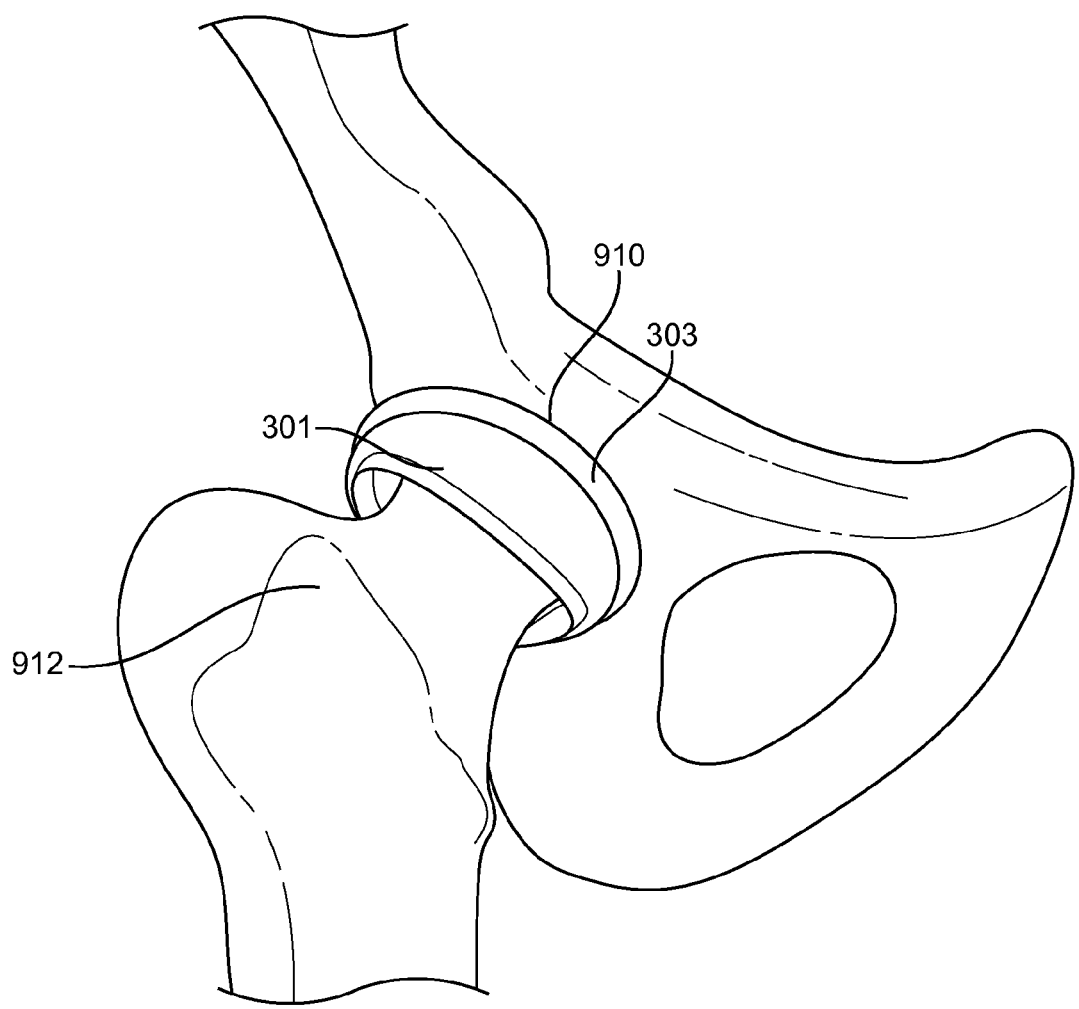
FIG. 2 shows the flexible implants of FIG. 1 attached to articulating surfaces of the acetabulum and femoral head.

FIG. 1 shows two exemplary flexible joint implants 301, 303 for the hip joint. A first cap shaped implant 301 is designed to fit over the femoral head 912. A second implant 303 is designed to fit into the acetabulum 910. FIG. 2 shows the flexible implants 301, 303 attached to respective bone surfaces. As shown, the flexible implants 301, 303 have mating articulating surfaces. In some embodiments, the flexible joint implants 301, 303 comprise a biocompatible polyurethane IPN or semi-IPN. The IPN or semi-IPN may include a hydrophilic, polymer on an articulation side of the implant. The IPN or semi-IPN may include a hydrophilic, net negatively charged polymer on an articulation side of the implant. The IPN or semi-IPN may include a hydrophilic, net negatively charged polymer such as sodium polyacrylate or polyacrylic acid on an articulation side of the implant. The concentration of hydrophilic polymer, net negatively charged polymer, or sodium polyacrylate or polyacrylic acid may change through a thickness of the implant where the highest concentration is at an articulation surface, decreasing with distance from the articulation surface. Additionally, the concentration of the polyurethane may also change across a thickness of the implant where the highest concentration is a bone-facing side. The bone-interfacing side may be substantially stiff compared to the rest of the material. Alternatively, the flexible implant may be comprised of a more flexible layer attached to a stiff backing. Additional details regarding the composition of flexible joint implants are described in: U.S. application Ser. No. 12/499,041 filed Jul. 7, 2009; U.S. application Ser. No. 13/219,348 filed Aug. 26, 2011; U.S. application Ser. No. 13/347,647 filed Jan. 10, 2012; U.S. application Ser. No. 12/536,233 filed Aug. 5, 2009; Ser. No. 12/148,534 filed Apr. 17, 2008; U.S. application Ser. No. 13/418,294 filed Mar. 12, 2012; International Application No. PCT/US11/4936 filed Mar. 23, 2009; and International Application No. PCT/US12/20828 filed Jan. 10, 2012, which are all incorporated by reference in their entirety.

Figure 3:
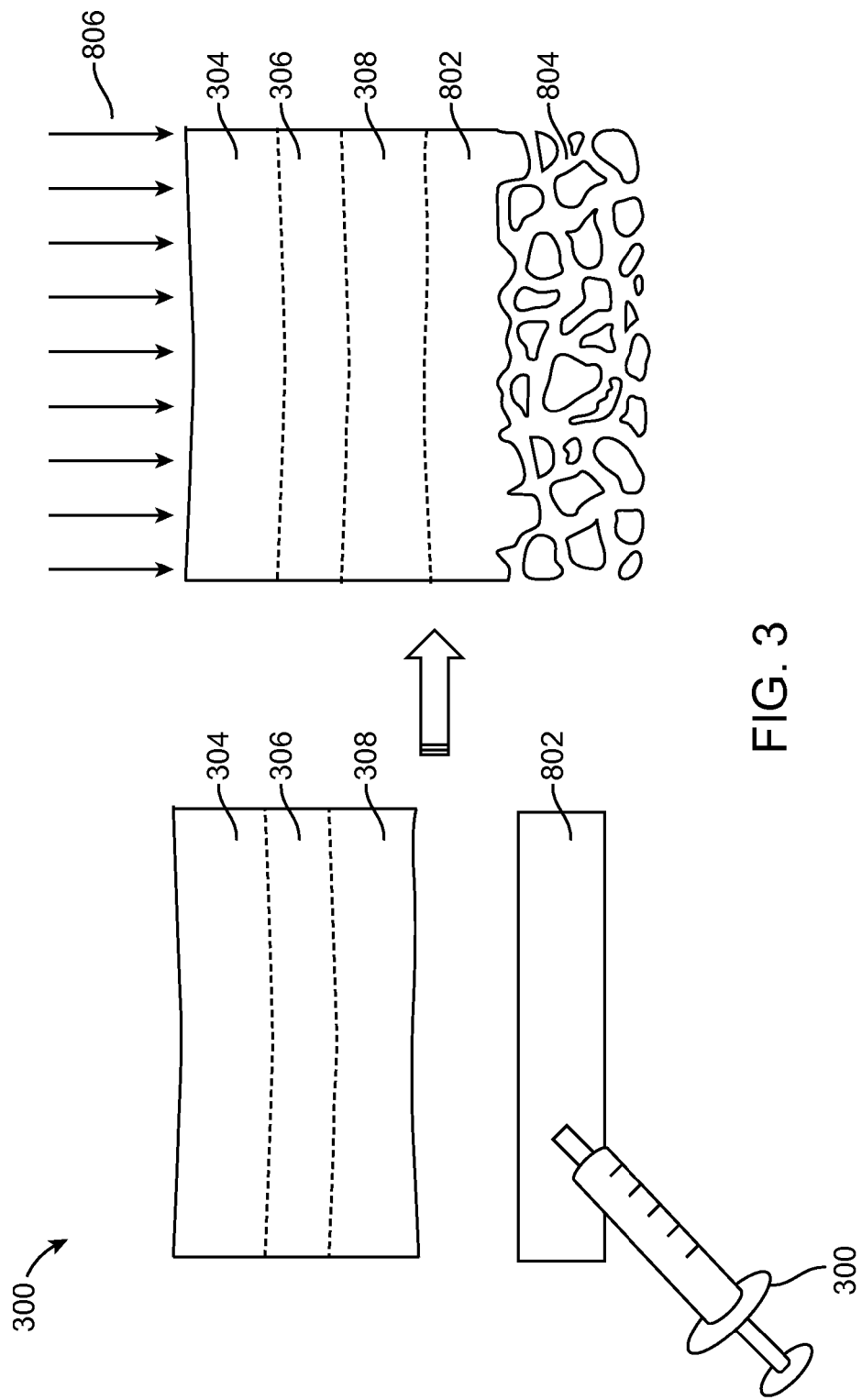
FIG. 3 illustrates application of adhesive to an implant surface.

The flexible implant can be anchored to the joint using an adhesive or curable compound such as bone cement. FIG. 3 shows a cross-section according to some embodiments of the implant where a curable adhesive 802 is applied to a surface of the implant 300. The adhesive may be applied by any method including by way of syringe 310. The composition of the implant 300 may be uniform throughout or contain a higher concentration of some materials on one end compared to another end. For example, implant 300 contains a bone-like stiffer anchoring surface at 308 and a cartilage-like hydrated lubricious bearing surface at 304. In some embodiments, a gradient and/or a transition zone 306 may exist between the lubricious bearing surface 304 and the stiff anchoring end 308. Once the adhesive 802 is applied to the anchoring surface 308, the implant with adhesive can be brought into contact with a joint or bone surface 804. Alternatively, in some embodiments, the adhesive can also be applied directly to the joint or bone surface instead or in addition to the implant surface. Light may be applied 806 to cure the adhesive thereby attaching the implant to the joint surface. In some embodiments, the implant material permits the sufficient passage of light through a thickness of the implant such that the adhesive is light-cured. In other embodiments, the adhesive may be thermally or chemically cured. Additionally, the curing may take place through a combination of thermal, chemical, or light-curing. Examples of curable compounds that can be used to anchor a flexible polymer implant include those described in: U.S. application Ser. No. 12/409,359 filed Mar. 23, 2009; U.S. application Ser. No. 13/542,464 filed Jul. 5, 2012; and U.S. application Ser. No. 13/573,788 filed Oct. 3, 2012, which are incorporated by reference in their entirety.

The phrases bone cement, curable compound, adhesive, curable adhesive, etc. are not limiting to any particular substances or compounds. Rather, these phrases and terms are broadly meant to refer to any compound that can be used to adhere, anchor, attach, affix, couple, or connect an implant to an implantation site. Such compounds may contain adhesive components. Additionally, some compounds, but not all, may be curable and/or polymerizable. In some cases, the attachment compound is an "ionic" type cements like zinc carboxylate. Additionally, dental cements, adhesives or compounds such as those listed in FIGS. 62A and 62B can be used with embodiments described herein. Examples of curable and non-curable compounds that can be used to anchor a flexible polymer implant include those described in: U.S. application Ser. No. 12/409,359 filed Mar. 23, 2009; U.S. application Ser. No. 13/542,464 filed Jul. 5, 2012; and U.S. application Ser. No. 13/573,788 filed Oct. 3, 2012, which are incorporated by reference in their entirety.

Some embodiments provide an implant container for holding the implant prior to use. An implant container according to the disclosure may support, enclose, grip, or hold an implant and prepare the implant for implantation in a joint. An implant container may maintain an implant in an expanded form, a contracted form, folded form, or in between. The container may support one or, more commonly, both sides of the implant. The container may have two (or more) sections; at least two of the sections may be configured for engaging opposite sides of an implant.

Figure 4:
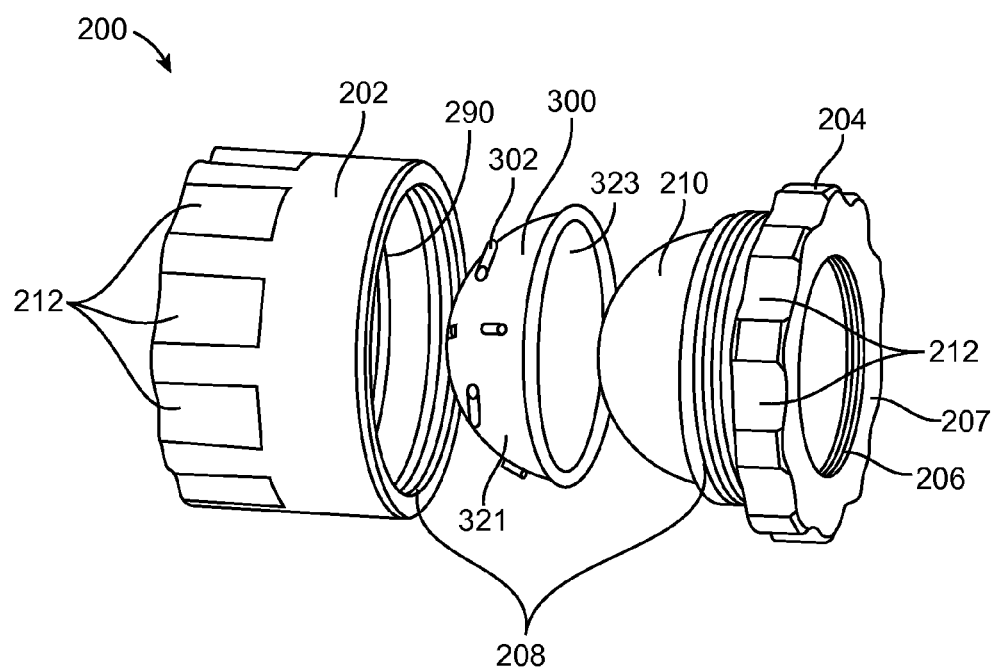
FIG. 4 illustrates components of an implant container.

FIG. 4 illustrates one embodiment of an implant container. As shown, the implant container 200 comprises a first component 202 adapted to receive and hold an implant 300. In FIG. 4, the first component 202 is a female member having a portion 290 designed to receive and surround part of the implant 300. The first component 202 can include sufficient volume to accommodate the placement of the implant 300 partially or completely into the first component 202. FIG. 4 shows the implant 300 as having a convex outer surface 321 that is generally spherical. The first component 202 may include an inner volume shaped to accommodate or mate with the outer surface 321 of the implant 300.

The container 200 also includes a second component 204 adapted to engage and hold the implant 300. The second component 204 may be a male member or lid designed to mate with the female member or first component 202 to enclose the implant 300. As shown in FIG. 4, the second component 204 includes a surface 210 that is configured to engage and hold the implant 300. The implant 300 may be held by the second component 204 by having the surface 210 engage an inner surface 323 of the implant 300. Where the implant 300 has a concave inner surface 323, the surface 210 of second component 204 may be spherical and convex to create a mating fit with the implant surface 323. To adequately hold the implant 300 onto the second component 204, a vacuum may be created in the contact space between implant surface 323 and surface 210 to secure the implant 300 to the surface 210 of the container 200.

Additionally, the second component 204 may include a shaping member or component that helps maintain the shape of an engaged implant. For example, as shown in FIG. 4, the spherical surface 210 is a generally convex protrusion that is sized and shaped to engage an inner surface 323 of the implant 300. The convex protrusion 210 when inserted into the implant 323 supports and maintains the hemispherical implant shape. Supporting and/or maintaining the implant shape may include contracting, deforming, expanding, reshaping, spreading out, or unfolding the implant.

In some embodiments, the shaping member or component may be a device distinct from the container that can be used with or without the container. The shaping member may support and/or maintain the implant shape as described above as a separate device.

Additionally, the second component 204 or shaping element protects a surface of the implant 300. As shown in FIG. 4, the inner surface 323 of the implant 300 engages and contacts an outer surface 210 of the second component 204. While engaged, the surface 210 covers and protects the inner surface 323 of the implant 300 from damage, especially during delivery and attachment.

FIG. 4 also illustrates another surface 207 of the container 200 adapted to engage a delivery tool. The surface 207 includes a delivery tool attachment element 206. In some embodiments, the delivery tool attachment element 206 is part of the first or second component 202, 204. The attachment element 206 is adapted to couple, attach, or engage a delivery tool such as a light delivery instrument. The attachment element 206 allows the implant to be delivered to an implantation location while still coupled to part of the container 200. For example, FIG. 4 shows second component 204 with an attachment element 206. FIGS. 7-12 show placement of the implant 300 on the second component 204 into the joint space. Delivery tool 102 is shown in FIGS. 8 and 10 as engaging the attachment element 206. The delivery tool 102 couples to the attachment element 206 and the second component 204 while the implant 300 is held onto a surface 210 of the second component 204. The delivery tool 102 may attach to the attachment element 206 in any suitable manner including mating threads.

In further embodiments, the first component 202 and the second component 204 attach to each other to enclose the implant 300. Sections of a container 200 may be held together by any means or mechanical mechanism, including but not limited to an adhesive, a lock-and-key, a clip, a clamp, a magnetic closure, screw threads, and a tape. The attachment may be accomplished by mating threads 208 on opposing sides of the components 202, 204. Alternatively, the two components 202, 204 may be coupled through an interference or friction fit. Additionally, the container 200 may include one or more indentations 212 to facilitate the movement of the first and second components 202, 204 relative to each other. The indentations may be placed along a perimeter of an outer surface of the components.

Figure 5:
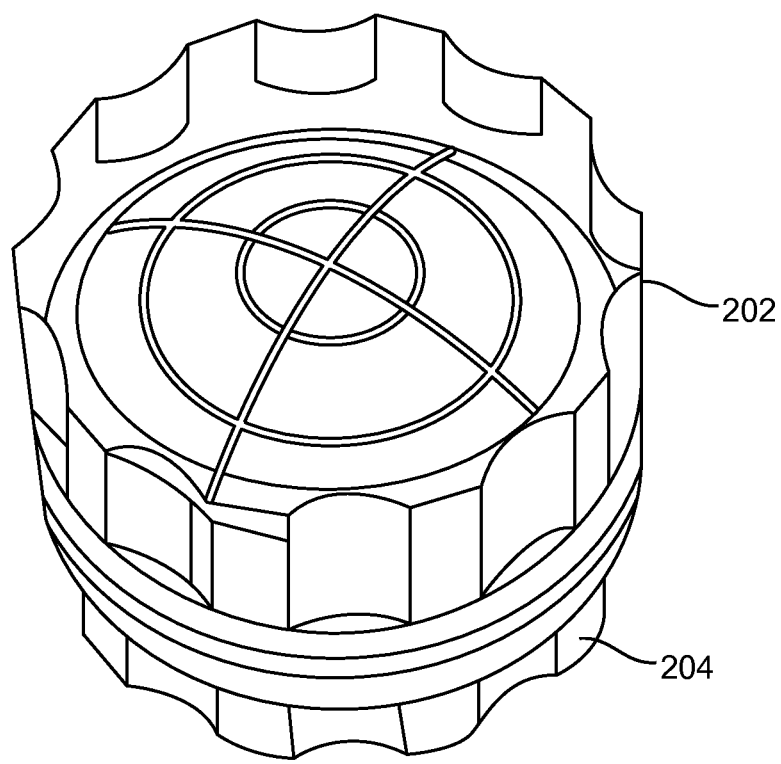
FIG. 5 illustrates a semi-transparent implant container.
Figure 6:
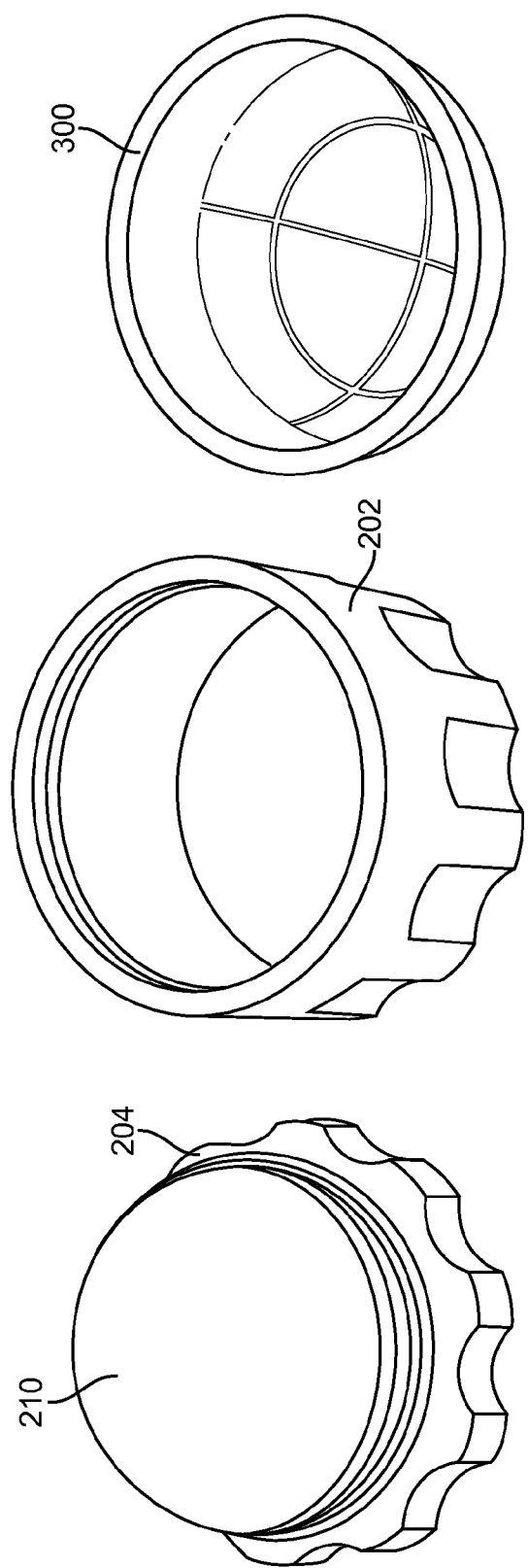
FIG. 6 illustrates components of a semi-transparent implant container.

Referring to FIGS. 5 and 6, some embodiments provide that some or all portions of the container 200 permit the transmission of light. FIGS. 5 and 6 show a semi-transparent container 200 where the first component 202 and second component 204 both allow transmission of light through a thickness. In other embodiments, only a portion of the container, such as a portion of the second component 204, allows transmission of light. Such portions may be transparent, semi-transparent, or translucent depending on the materials employed. Where a portion of (but not necessarily all) of the container transmits light, one container section may be configured to deliver any form of energy when connected to an energy (e.g. a light) source. For example, if an adhesive is light-curable, then a portion of the container may be at least semi-transparent to allow passage of light from a light delivery instrument (light source), through the thickness of the implant, and onto a light-curable adhesive pre-polymer to initiate curing. The device enclosure may comprise any transparent, semi-transparent (translucent) material, including, but not limited to glass, polycarbonate, polymethyl methacrylate (PMMA), polymethylpentene (PMP), polystyrene, polysulfone, polypropylene, polyethylene terephthalate (PET), quartz, silicone, or combinations thereof.

Figure 7:
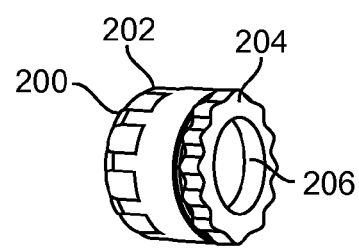
FIG. 7 illustrates a closed implant container.
Figure 8:
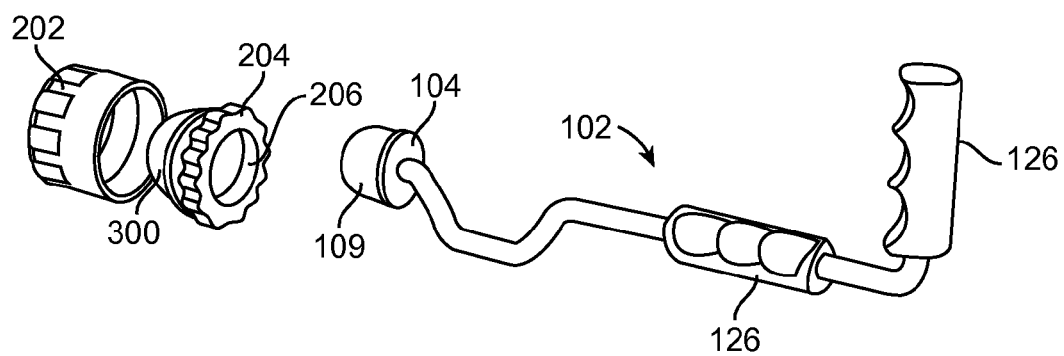
FIG. 8 illustrates an implant container with an attachment portion and a delivery tool.

As mentioned, FIGS. 7 through 14C illustrates examples of delivering and attaching an implant 300 using the container 200 and delivery tools. FIGS. 7 and 8 show the container 200 comprising a male side 204 with a hemispherical convex protrusion and a female side 202 with a hemispherical concave depression. Implant 300 is an acetabular implant positioned between the convex and concave aspects of two sections of the container 200. In some embodiments, the three items may be designed and manufactured to precisely fit together and may be packaged and sterilized together.

As shown in FIG. 8, the container 200 may have other functions in addition to housing an implant, including connecting with a delivery instrument 102. The female side or first component 202 of the container may be designed to be easily removed in order to expose the acetabular implant 300 in a preferred or precise position for implantation within an acetabular cavity. In other words, the first component 202 may be removed without disturbing the position of the implant 300, which remains physically held by the second component 204.

Figure 9:
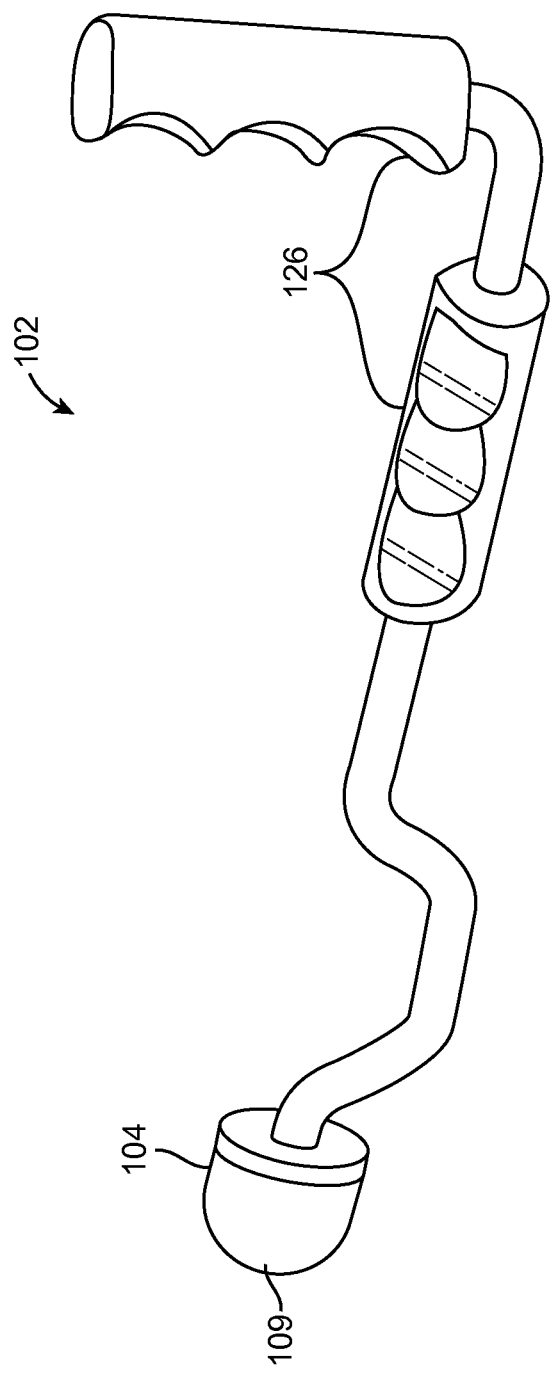
FIG. 9 illustrates the delivery tool of FIG. 8.
Figure 10:
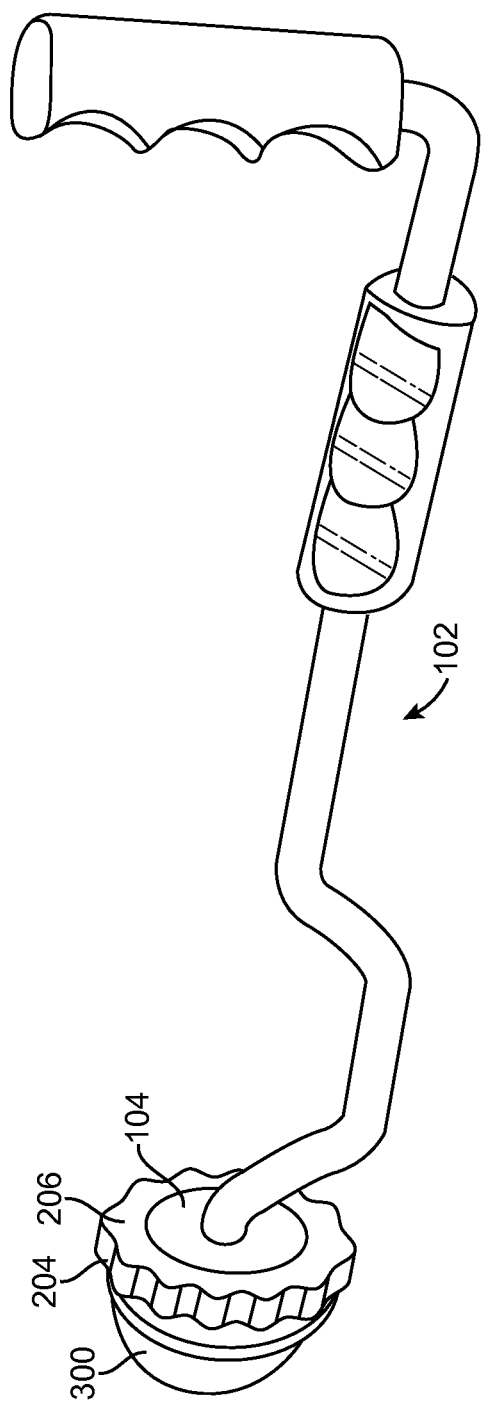
FIG. 10 illustrates the delivery tool of FIG. 8 connected to a container component.

As shown in FIG. 9, the delivery instrument 102 may be any delivery assistance tool such as a device with an elongated arm to facilitate maneuvering the implant 300 into the acetabular joint space. The delivery tool 102 may include gripping members or handles 126 to allow manipulation of the tool and the implant to the joint. Additionally, the delivery tool may include an arm with twists, bends, or curves to accommodate the positioning and attaching of the implant in the patient's body. The handle 126 may include portions that are perpendicular to other portions. Additionally the handle 126 may include a U-shaped curve near a distal end of the device 102. The delivery instrument 102 may also include a connector 104 to connect and attach the delivery instrument to the attachment member 206 of the container 200.

In other embodiments, the delivery tool 102 is a light delivery instrument configured to provide sufficient light to cure an adhesive on the implant surface. The light delivery instrument may take any shape and be of any material that facilitates placing an implant into a joint. A light delivery tool may be substantially linear, curved, serpentine, or spiral. As shown in FIG. 8, the delivery tool 102 can be a light delivery instrument with a light applicator 109.

Referring again to FIG. 8, the first component 202 can be removed from the second component 204 of container 200. The second component 204 includes an attached acetabular implant 300 on a surface of the second component 204. In some embodiments, the second component 204 has a surface engaging the implant 300 such that the shape of the implant 300 is substantially maintained or formed while the implant 300 is held on the second component 204. Supporting, conforming, and/or maintaining the implant shape may include contracting, deforming, expanding, reshaping, spreading out, or unfolding the implant. The delivery instrument 102 has a connector 104 for attaching to the attachment element 206 of the second component 204. FIG. 10 shows the delivery instrument 102 attached to the second component 204.

Figure 11:
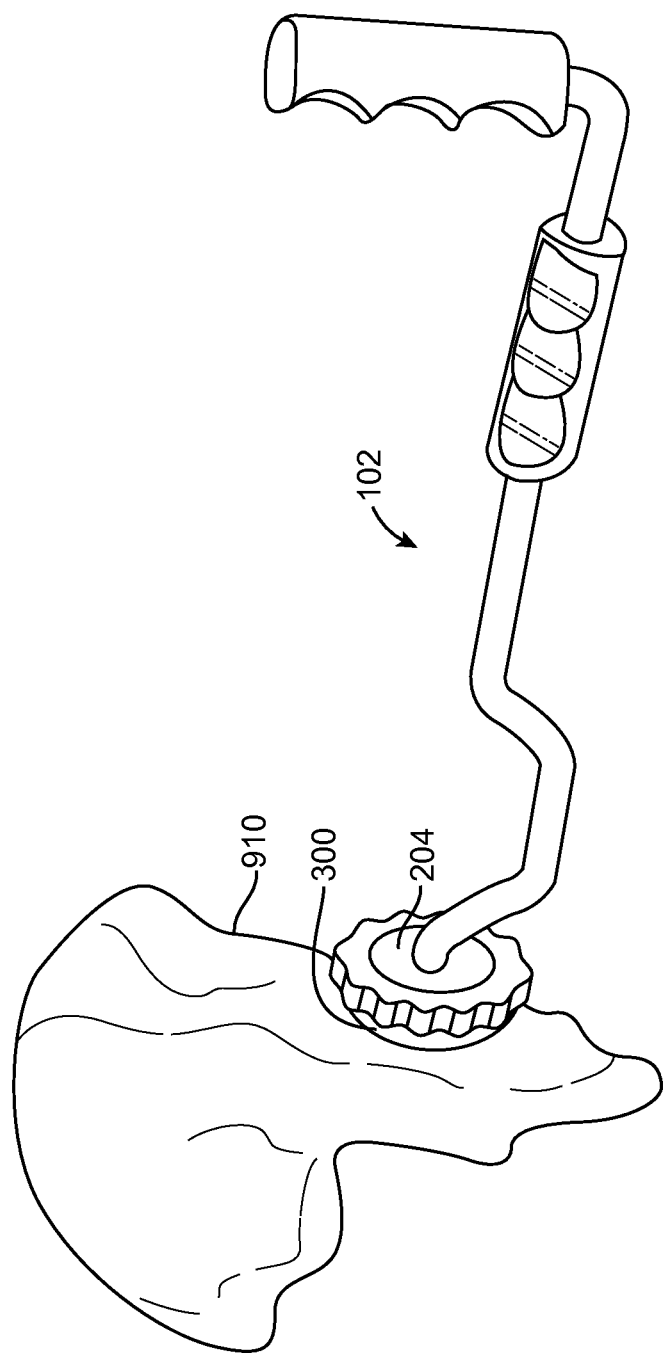
FIG. 11 illustrates the delivery tool and implant assembly of FIG. 10 delivering an implant to the acetabulum.
Figure 12:
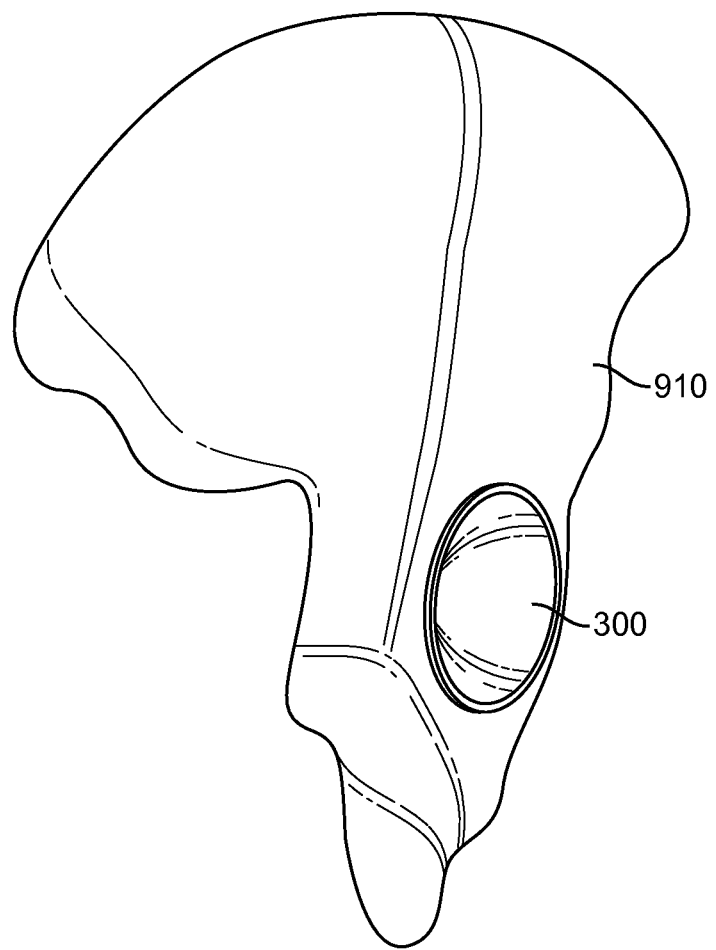
FIG. 12 illustrates the acetabulum with a flexible implant.
Figure 13:
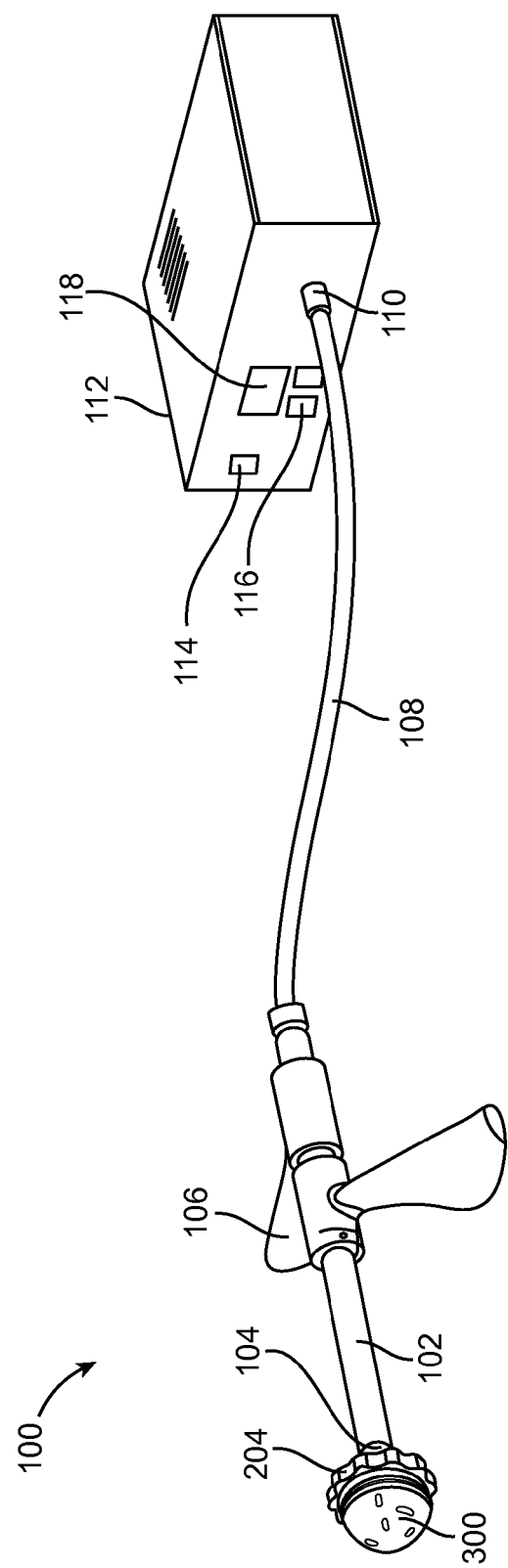
FIG. 13 shows a light delivery instrument and curing system.
Figure 14A:
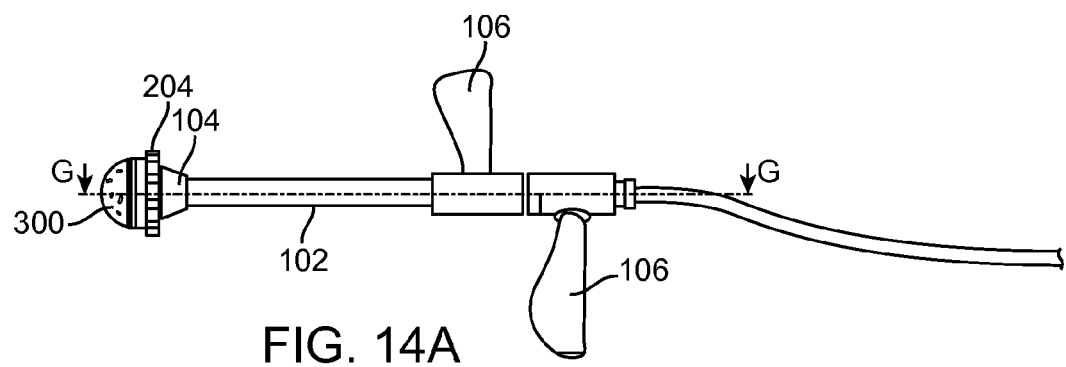
FIG. 14A-C shows components of the delivery and curing system in FIG. 13.
Figure 14B:
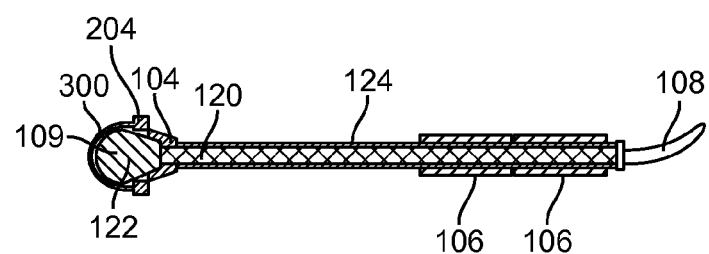
Figure 14C:
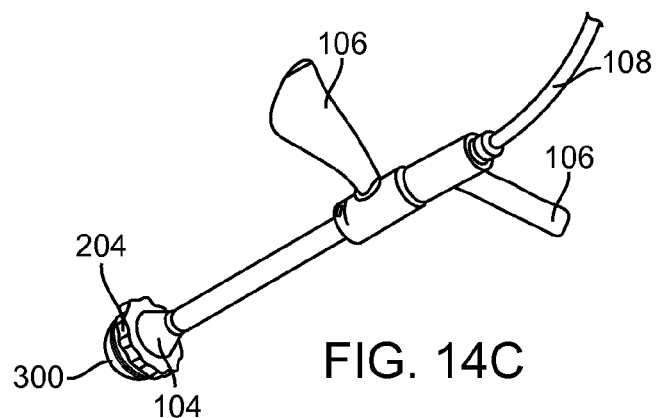

When uncovered by the removal of the first component 202, a curable adhesive may be applied to the implant surface. Once the curable adhesive is applied, a surgeon may take the entire assembly of implant 300, second component 204, and delivery instrument 102, and place or press it into an acetabular cavity 910 as shown in FIG. 11. An implant 300 connected with an assembly may be applied in one motion, without manually adjusting the position and alignment of the implant.

Once in place, the surgeon may hold the assembly in position until the adhesive compound has adequately cured to attach the implant to the joint surface. Thermal, chemical, or light-curing can be used. In the case of thermal curing, the surgeon holds the assembly in position during the curing process. In the case of light-curing, the surgeon may activate a light source (e.g. press a button on the light delivery instrument) to apply light through the distal end of the instrument, through the second component 202 and implant 300, and onto an adhesive sandwiched between the implant 300 and underlying bone to cure an adhesive and, in turn, anchor the implant 300 in place. The delivery instrument 102 may include a light applicator 109 that provides light for curing. The light applicator 109 may include at least one LED or an array of LEDs to provide light. As discussed, the container can comprise a material that allows for the transmission of light through a thickness of the container. Additionally, the implant 300 also may comprise a material that similarly allows transmission of light to a surface of the implant. The implant material may be semi-transparent, transparent, or translucent to allow penetration of the light to the implant surface to cure the adhesive. In some embodiments, the light delivery device delivers light sufficient to transmit through the second component 204 and the implant 300 even where a portion of the light may be absorbed in passage through the materials.

Once the implant 300 is attached to the acetabular cavity 910, the delivery instrument 102 and attached second component 204 of the container are removed. In some embodiments where the implant is attached to the second component 204 by vacuum suction, the vacuum may be released or broken to remove implant from the second component 204. For example, in some embodiments, if the vacuum is achieved by using a pump, the pump can be turned off to allow air to re-enter the interface between the second component 204 thereby releasing the suction hold. In other embodiments, if the vacuum is achieved by a syringe/plunger mechanism, the plunger can be repositioned to move air back into the interface thereby releasing the suction and allowing the implant to be removed from the second component and/or shaper 204.

In other embodiments, the second component 204 may not be part of a container. In such cases, the second component 204 is a stand-alone shaping element that maintains, supports, or conforms the shape of the implant when the implant is attached to the shaping element. The shaping element or shaper may be pre-attached or attachable to the implant to facilitate anchoring the implant to a target location.

FIGS. 13 and 14A-C illustrate a delivery and curing system 100 with an alternative delivery instrument that is also a light delivery instrument. The described light delivery instrument 102 includes a distal end with a connector 104 for connecting to an attachment element 206 of the second component 204 of the container 200. The energy (light) source 112 may deliver energy (e.g. light) to the second component 204 and implant 300 by any mechanism, especially by a mechanism that can be controlled by a user (physician). Any form of energy may be delivered, including but not limited to microwave, infrared, visible light and ultraviolet light. In a particular example, a blue light is delivered.

In some embodiments, the light delivery instrument 102 comprises a fiber optic cable 120 in a housing 124. The housing 124 may, for example, be a metal tubing that terminates on one end in a light diffuser unit 122, and on the other end in a lightguide cable 108 that leads to a power unit 112. The lightguide cable 108 may connect to the power source 112 through a cable socket 110. The light delivery instrument 102 may also include gripping members or handles 106 to help manipulate the instrument and any attached components to a joint space. The handles 106 may be placed along a lateral axis of the instrument 102. The power source may include a start/stop button 114, a timer adjustment button 116, and a countdown timer 118 (or any other suitable controls) to help control light transmission and curing rate.

In some embodiments, the second component 204 may further comprise a light diffuser 122 configured to engage with the light applicator 109 such that light projected from a light exit end of the light delivery instrument 102 into the second component 204 of the container 200 is diffused by the diffuser 122. Alternatively, the light diffuser 122 may be separate from the container 200, such as comprising part of the light applicator 109. Additionally, in any of the described embodiments, the light applicator can have a cross-sectional diameter between about 30 mm and 60 mm.

As shown in FIGS. 13 and 14A-C, light energy can be generated by a power unit 112 and travel through a fiber optic cable 108 to be scattered to transmit light through the second component 204, the surface of the second component 204, and the implant 300 so that some, most, or all areas of the adhesive adjacent the implant 300 are exposed to light. In one specific embodiment, light is scattered radially from a central point by a distal light diffuser unit 122 to deliver light evenly in a radial distribution through the second component 204, the implant 300, and onto the light-curable adhesive to thereby cure the adhesive and hold the implant 300 in place.

Figure 15:
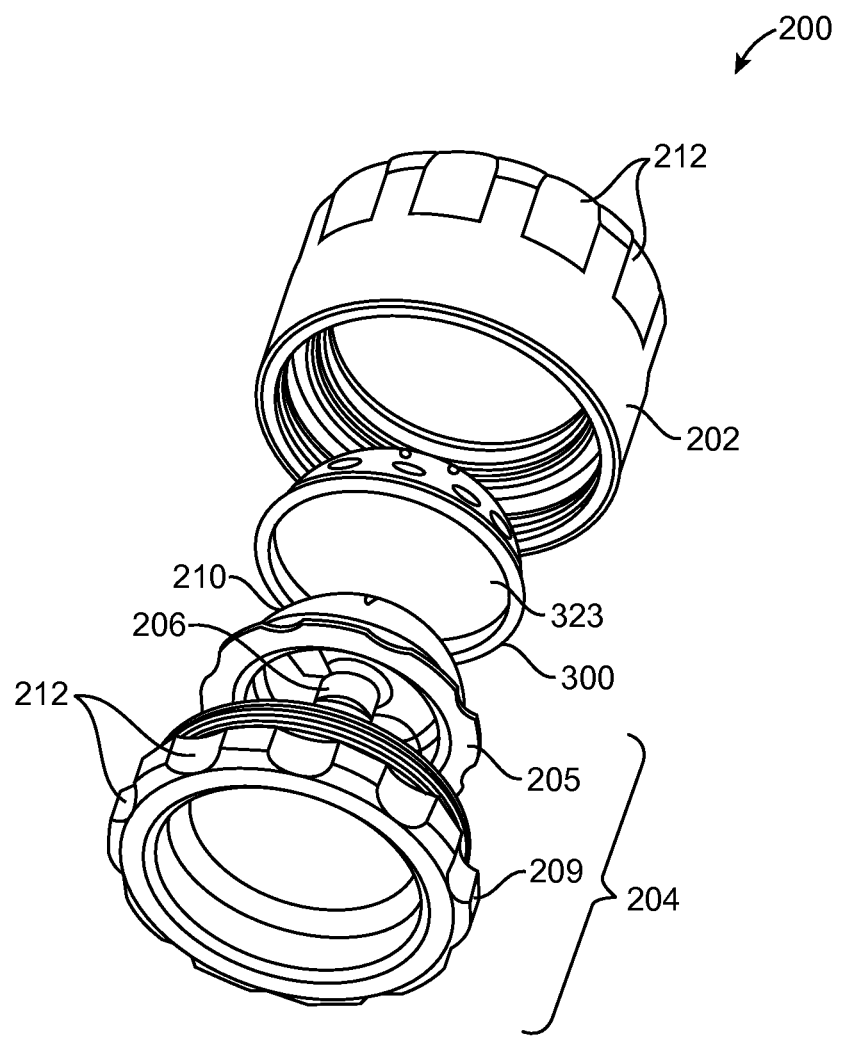
FIG. 15 illustrates an exploded view of an implant container.
Figure 16:
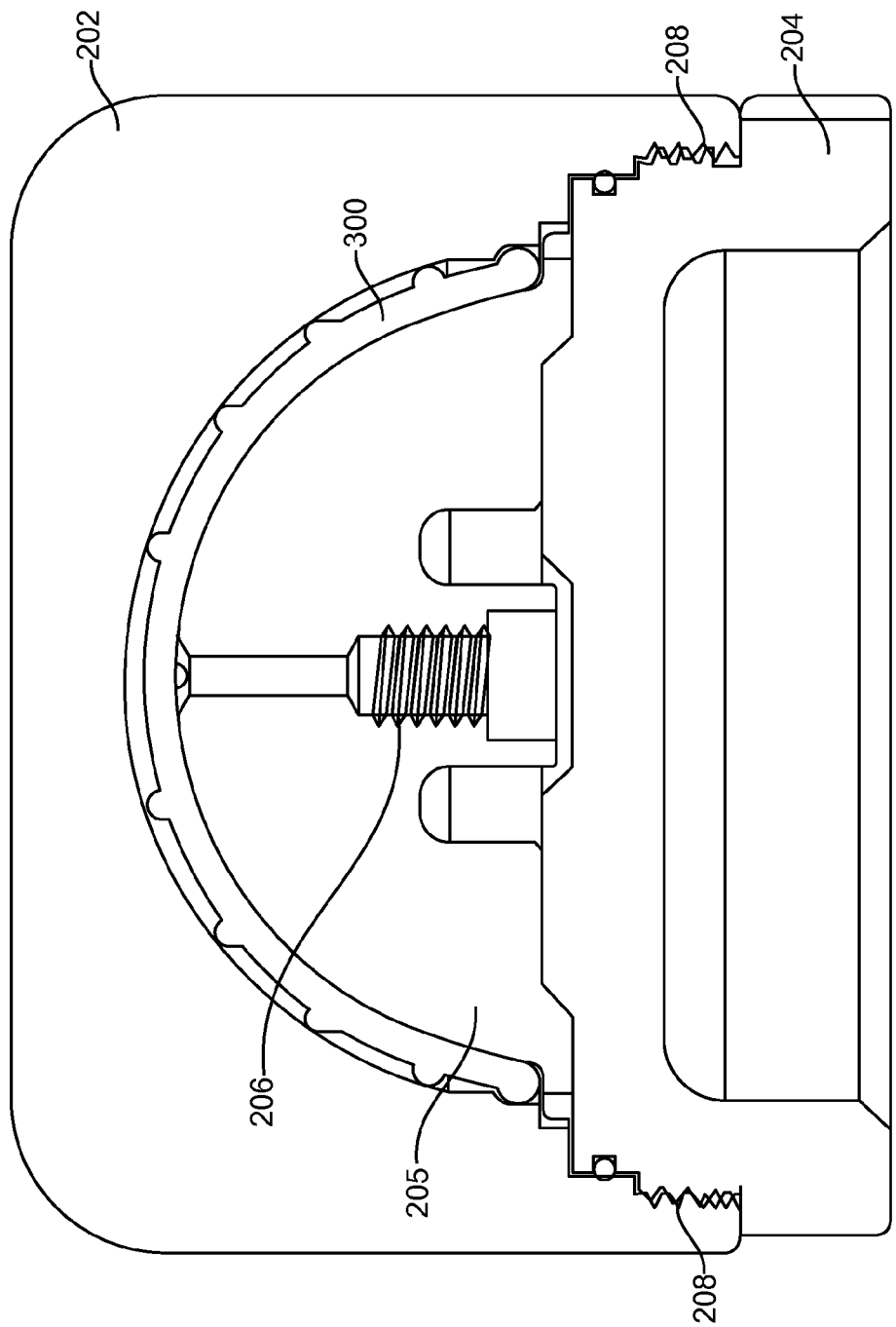
FIG. 16 is a cross-sectional view of the implant container in FIG. 15.
Figure 17:
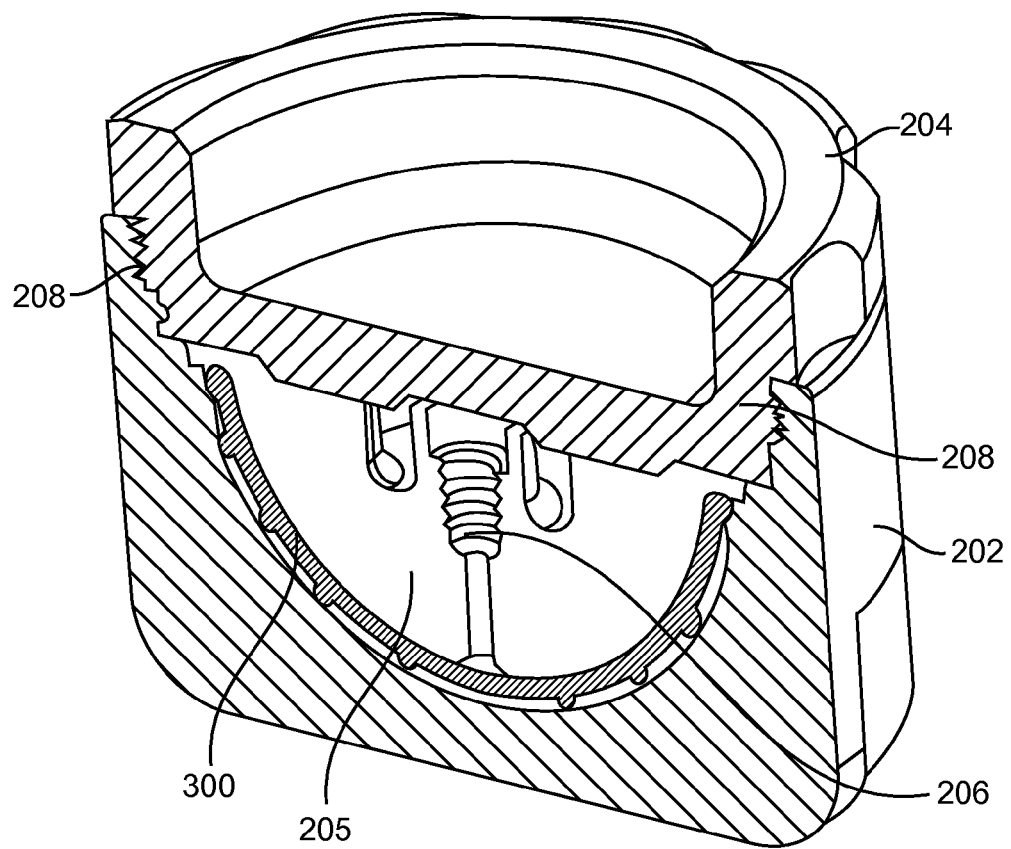
FIG. 17 is another cross-sectional view of the implant container in FIG. 15.

Referring to FIG. 15, an alternative implant container 200 is shown. The implant container 200 comprises a first component 202 adapted to receive and surround an implant 300 and a second component 204 configured to hold and maintain the shape of the implant 300. The second component 204 may further include two subcomponents 205, 209. For example, the second component 204 can include a lid 209 that mates with a shaper 205. FIGS. 16 and 17 provide cross-sectional views of the container shown in FIG. 15. As shown, the container 200 may hold the implant 300 by enclosing the implant 300 when the first component 202 and second component 204 are attached or coupled together. For example, FIGS. 15 through 17 show mating threads 208 for coupling the first and second components 202, 204 together.

The shaper 205 is adapted to hold and engage the implant. In some embodiments, the shaper has a convex spherical surface 210 to engage a concave surface 232 of the implant 300. Once engaged, the implant's shape is maintained by the shaper 205. To adequately hold the implant 300 onto the shaper 205, a vacuum may be created in the contact space between implant surface 323 and surface 210 to secure the implant 300 to the surface 210 of the container 200. In some embodiments, the diameter of a hemispherical shaper is between about 38 mm to 60 mm. In any of the embodiments, the diameter of the shaper may be between about 30 mm and 60 mm.

Figure 18:
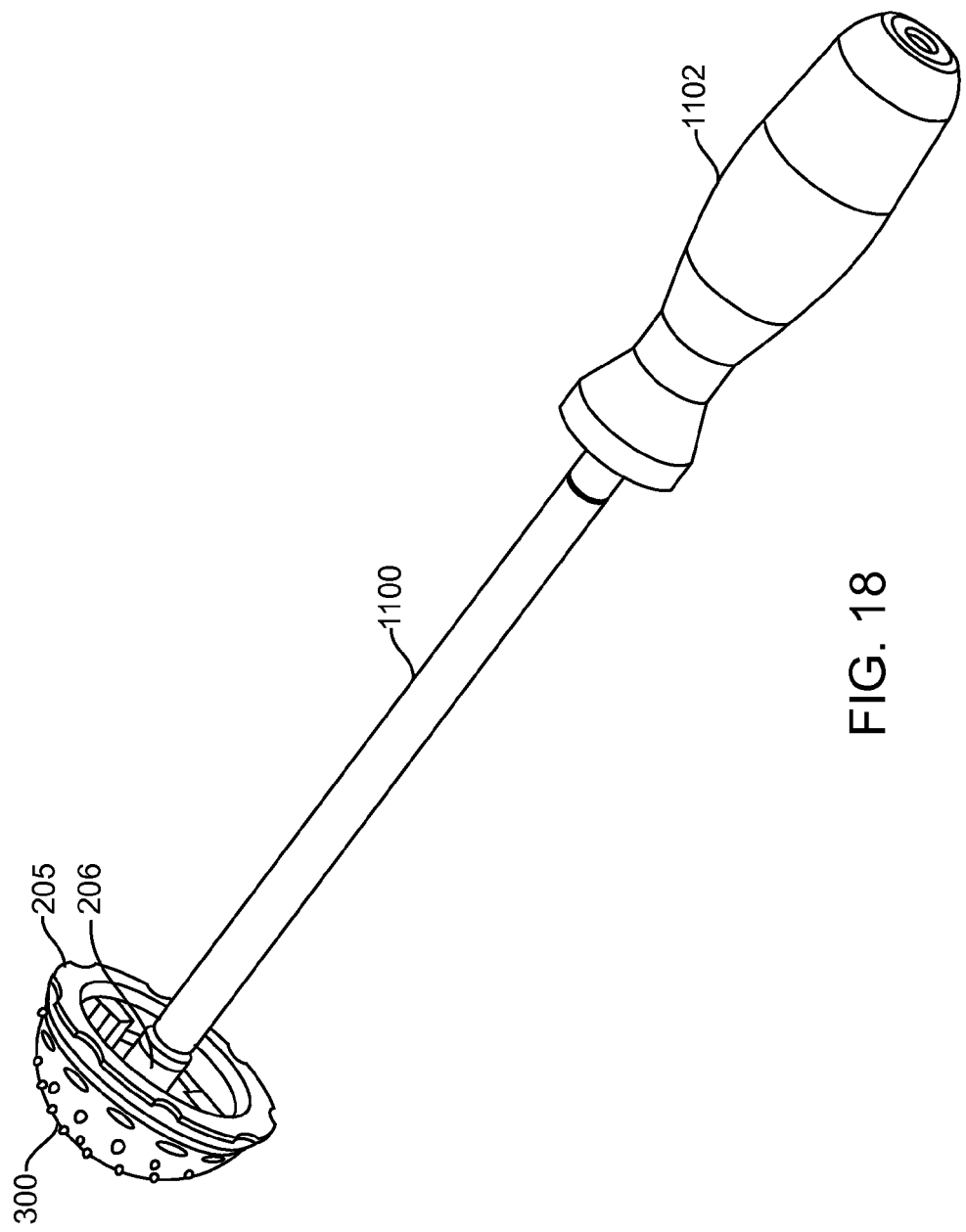
FIG. 18 is a side view of a shaper of the implant container in FIG. 15 attached to a delivery tool.
Figure 19:
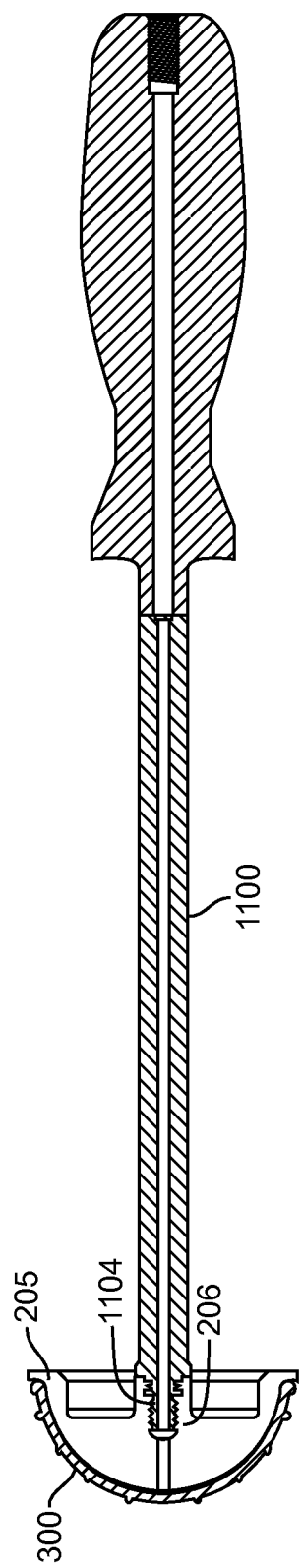
FIG. 19 is a cross-sectional view of the assembly in FIG. 18.

Additionally, the shaper 205 may be removable from the container 200 while the implant 300 is attached. The shaper 205 can include an attachment element 206 to allow attachment to a delivery tool. FIGS. 18 and 19 show the shaper 205 holding implant 300. The shaper 205 is attached to a delivery tool 1100 by screw threads between the attachment element 206 on the shaper 205 and a connector 1104 at an end of the delivery tool 1100. Although shown as screw threads, any suitable means for attachment can be used such as, but not limited, to an adhesive, a lock-and-key, a clip, a clamp, a magnetic closure, and tape.

In some embodiments, the shaping member or shaper 205 may be a separate device from the container that can be used with or without the container. The shaper 205 may support and/or maintain the implant shape as described above as a separate device. Additionally, the shaper 205 can include an attachment element 206 as described for attachment to a delivery tool. In use, the implant 300 may be packaged separately or together with the shaper 205. If separate, the implant 300 is attached to the surface of the shaper 205. A delivery tool 1100 can be connected to the shaper 205 by the attachment element 206. Once attached, the delivery tool 110 can be used to maneuver the implant 300 and shaper 205 to a target location. In such embodiments, the shaper 205 is not necessarily part of a container or a component of the container (although it can be). Moreover, the shaper 205 can be reusable.

The delivery tool 1100 may be a light delivery device or a non-light delivery assist device to help maneuver the shaper 205 and attached implant 300 to a joint. FIGS. 18 and 19 show a non-light delivery tool where the acetabular implant 300 can be positioned in an acetabular joint space for attachment. In some embodiments, a vacuum source can be contained in the handle 1102 of the delivery tool 1100.

Figure 20:
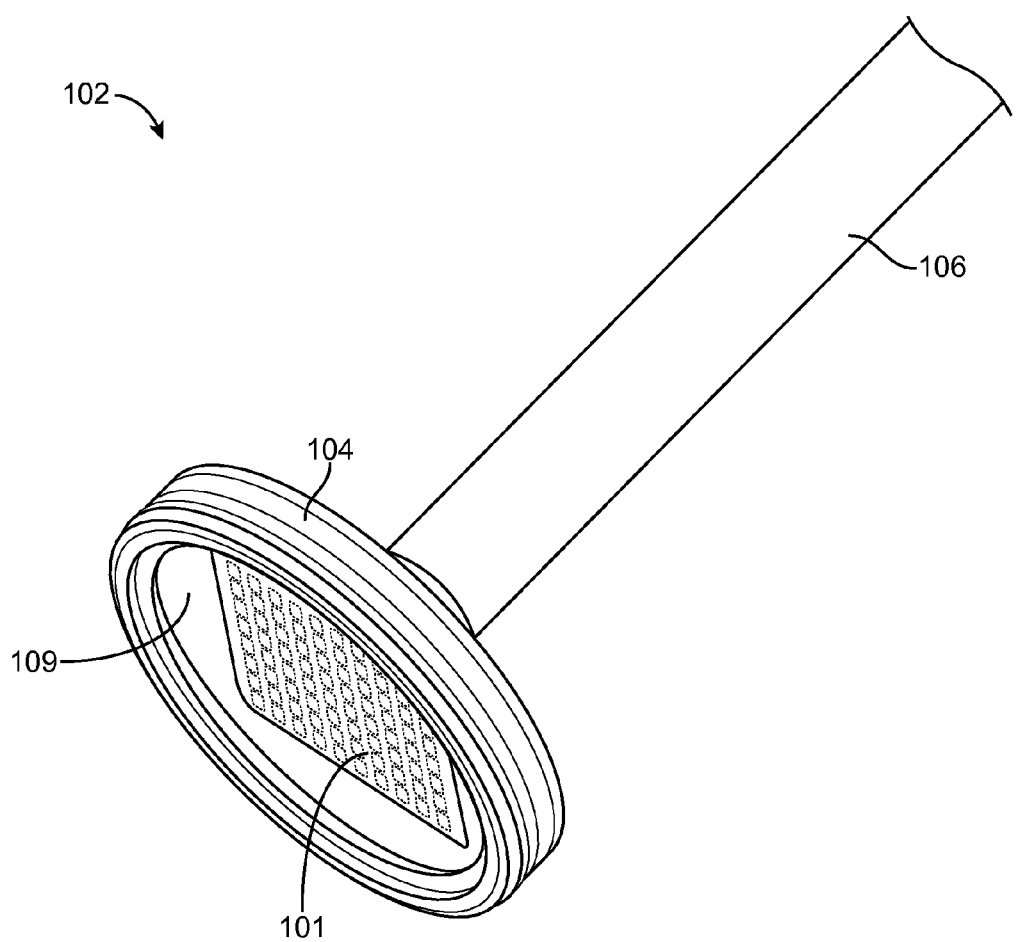
FIG. 20 illustrates the working end of a light delivery instrument.

FIG. 20 shows a light delivery device 102 for attachment to the shaper 205. The light delivery device 102 has a connector 104 at a light exit end (or working end) of the light delivery device 102. A light applicator 109 is also positioned at the light exit end to project light into a connected shaper 205. The light applicator 109 includes a LED array 101. In some embodiments, the light delivery device 102 may comprise mating threads on the light exit end to attach to a shaper 205. Any means for attachment may be used to connect the light delivery device 102 to the shaper 205, including an interference fit or any mechanical mechanism. In other embodiments, the shaper 205 is attached to the light delivery device 102 by means of vacuum suction of the shaper 205 against the delivery device 102.

Figure 21:
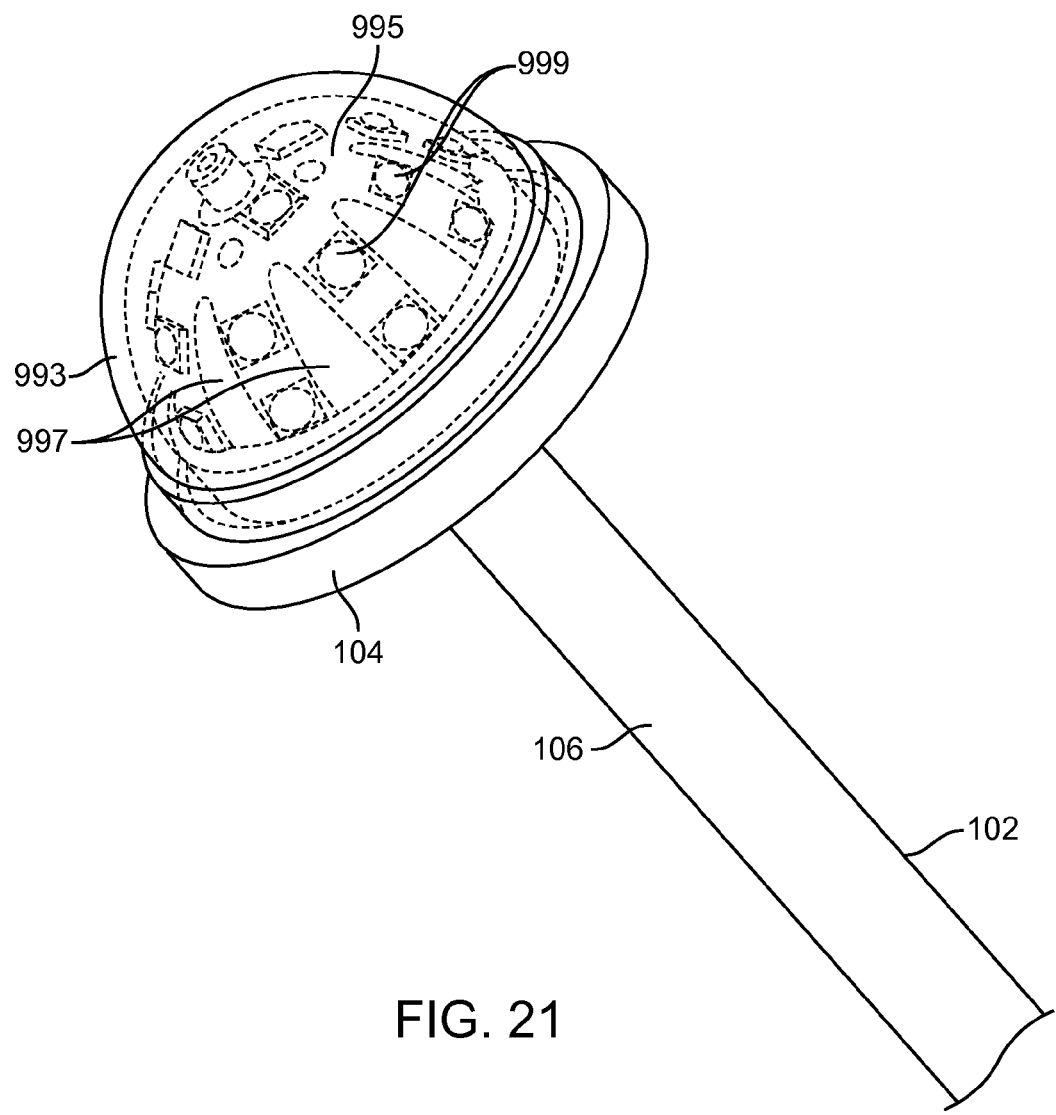
FIG. 21 illustrates the working end of a light delivery instrument.

Referring to FIG. 21, some embodiments provide for a light delivery instrument with hemispherical convex shape at the light exit or work end. The light exit end has a spherical cover 993 that is transparent, translucent, or semi-transparent to allow light transmission. An array 995 of LED/light emitting component(s) 999 are housed under the protective spherical covering 993. The LED(s)/light emitting components 999 may be set apart by spacers 997. In additional embodiments, the light delivery instrument 102 in FIG. 21 can be placed into a concave portion of an implant to attach the implant to a surface by light-curing a compound between the implant and the surface.

In some embodiments, the implant 300 may include surface features such as bump(s), depression(s), groove(s), pore(s), rough area(s), space(s) etc. that a facilitate attachment of the implant 300 to the target surface. In some embodiments, bumps are surface features that provide interdigitation anchors for the cement/adhesive. The surface features such as bumps may have a height between about 1 mm-2 mm. However, the surface features may be smaller or larger than 1 mm-2 mm. In some embodiments, the shape of the surface features can vary, from hemispherical to square, or cylindrical. Additionally, the surface features can be continuous circumferential grooves or protrusions of any cross section. In some embodiments, the implant (e.g. acetabular implant) has about 36 to about 48 surface features. In additional embodiments, the implants (e.g. femoral implants) have about 56 surface features.

Figure 22:
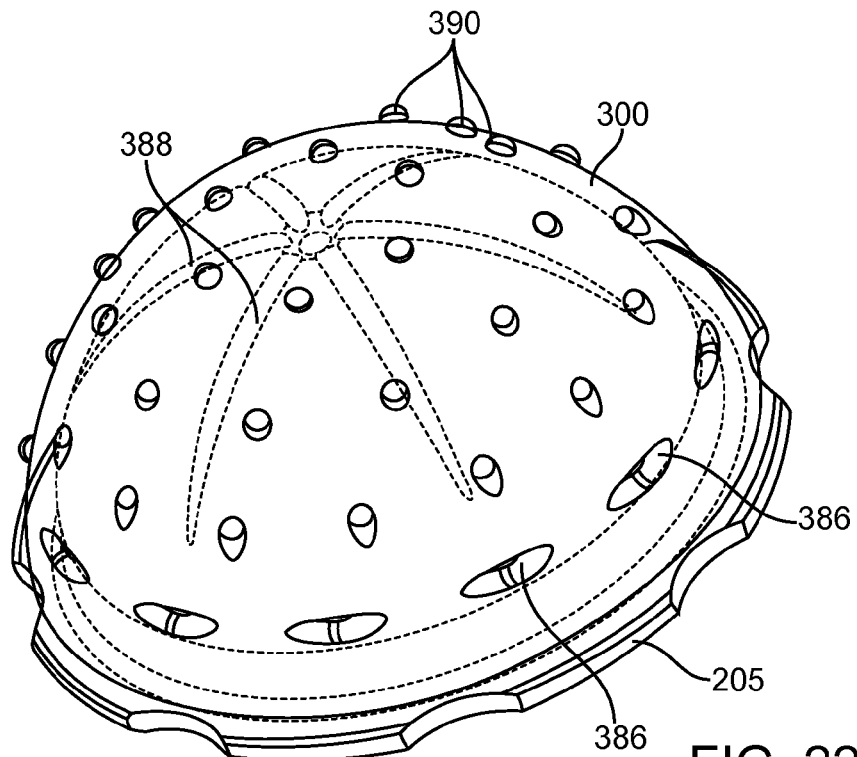
FIG. 22 illustrates an implant attached to a shaper.

As shown in FIG. 22, the surface of the implant 300 has grooves and/or bumps 390, 386. 1. The implant surface features may serve to maintain a desired spacing between the anchoring surface of the implant and the bone/attachment surface. For example, the surface features can create a space for adhesive/glue between the implant surface contacting a joint surface. Additionally, the surface features can provide a geometry for enhanced fixation. In some embodiments using bone cement, the surface features provide geometry for the cement to grout/interlock with. For an adhesive it provides additional surface area for chemical bonding. This results in additional resistance to movement or separation/pulling out of the implant after attachment.

Figure 23:
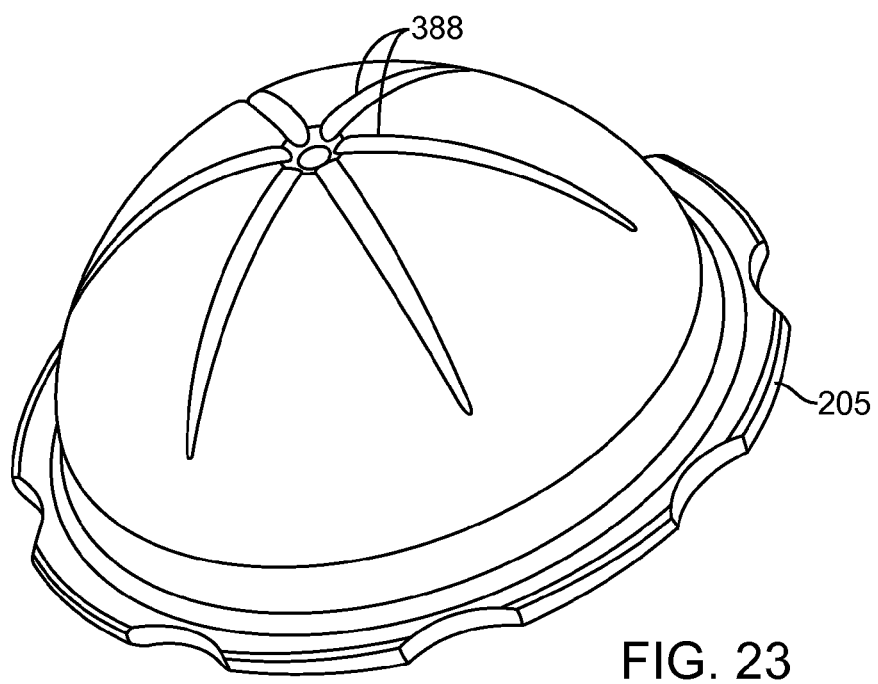
FIG. 23 illustrates a shaper with surface grooves.

Additionally, the shaper or container component 205 may also include surface features to facilitate holding the implant onto the shaper 205. For example, FIGS. 22 and 23 show grooves 388 on the convex surface of the shaper 205. In some embodiments, the grooves 388 provide channels to facilitate suction of the implant onto the shaper 205 during delivery and curing.

Although described above as a container or a separate shaper for an acetabular implant, it can be appreciated that the implant employed may have any variety of shapes depending on the target location and function of the implant. Likewise, the particular shape of the implant may dictate the shape and components of the container and/or shaper. For the hip joint, the acetabulum has a generally concave surface which generally requires that an artificial cartilage implant also mirror that concave form. To contain an acetabular implant and maintain the implant shape, the container/shaper, as described in embodiments above, would have components such as a shaping element to maintain the concave form of the implant before and/or during the implantation process. Additionally, in any of the described embodiments, the container/shaper and any of its components are reusable.

Figure 24:
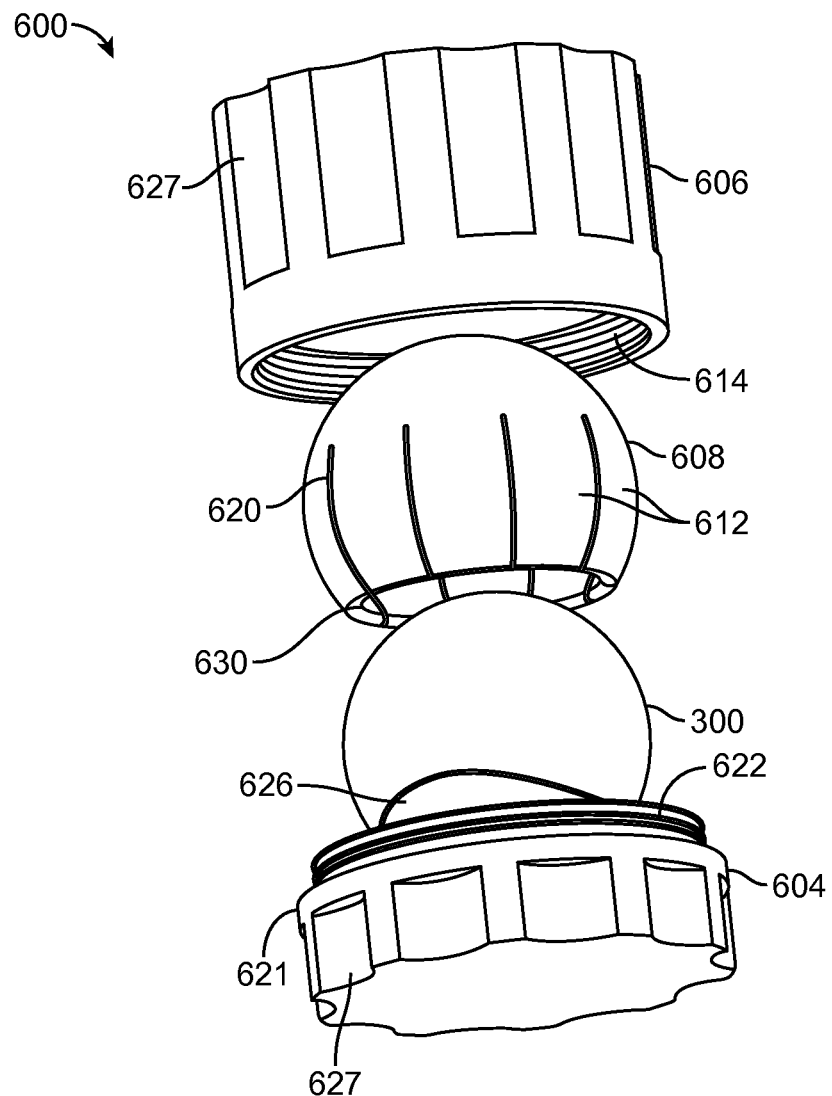
FIG. 24 is an exploded view of another embodiment of the implant container and components.
Figure 25:
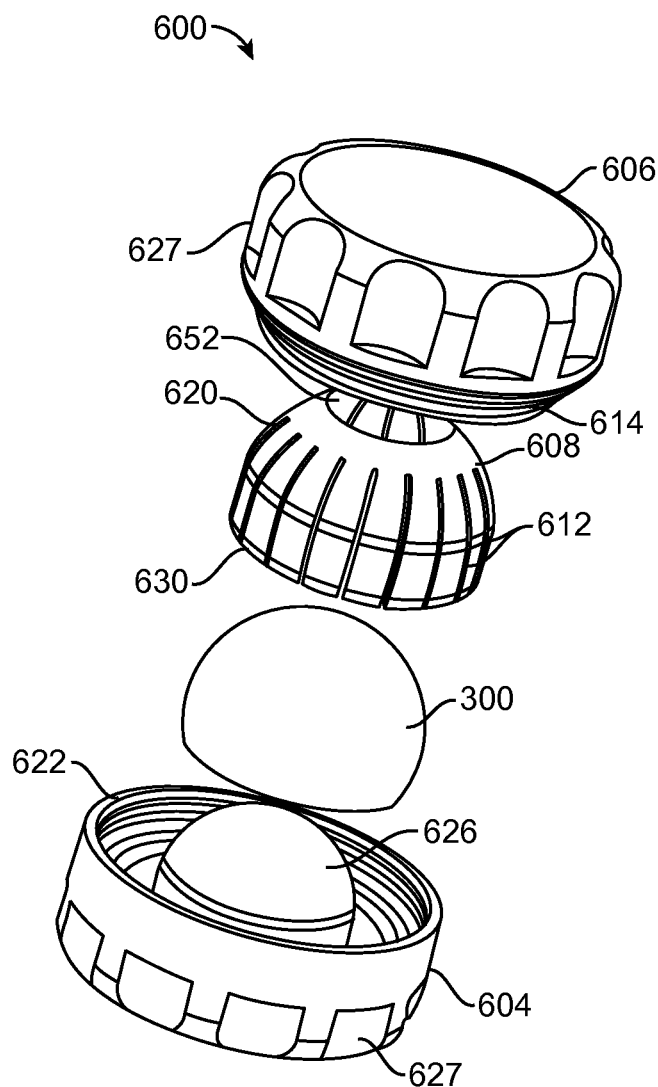
FIG. 25 is an exploded view of a further embodiment of the implant container and components.

As another example, FIGS. 24-25 illustrate a femoral head implant container 600 having a first component 606 adapted to surround and hold the femoral head implant 300 when the first component 606 is mated to a second component 604. The femoral head is spherical in shape and articulates with the acetabulum to form a "ball-in-socket" joint. Unlike the acetabulum, the femoral head has a convex surface area. The cartilage on the femoral head covers a surface area of greater than 180 degrees. Replacing the cartilage completely requires an implant that also covers this area essentially completely (e.g. covers a surface area greater than 180 degrees).

One way to cover the femoral head with an implant while preserving the spherical geometry of the underlying bone is to use an implant that can be pulled down over the maximum diameter of the femoral head. This would require an opening diameter on the implant that can "stretch" to a larger diameter transiently to allow it to clear the maximum diameter of the head. Flexible femoral cartilage replacement implants—in contrast to the rigid, inflexible metallic implants used in the industry today—have the ability to do just that. A femoral head may also be covered by easing, guiding, or wrapping an implant that has an opening or slit around the femoral head. Some embodiments provide for the opening diameter of the implant to be between about 30 mm to about 50 mm.

Referring to FIGS. 24-25, the femoral implant container enables the proper positioning, alignment, and anchoring of the implant over the femoral head. FIGS. 24-25 show a convex first component 606 or female side that surrounds and encloses the implant 300. A second component or male side 604 attaches to the first component 606 to enclose the implant 300 within the container. The second component 604 includes a convex surface 626 that can be inserted into a concave cavity of the femoral implant 300. While inserted into the implant 300, the second component 604 can assist in maintaining the desired form of the flexible implant 300. To do so, the convex surface 626 may share a shape or dimensions similar to a typical femoral head. Placing the implant 300 on the convex surface 626 can mold or conform the compliant implant material to a shape more like the destined target location. As shown in FIGS. 24-25, the convex surface 626 has a convex protrusion that has a diameter between about 30 mm to about 60 mm. The convex surface 626 is a partial sphere with a neck connecting the surface 626 to a flange or lip 621.

The first component 606 may comprise a concave outer enclosure that surrounds the implant 300 when the first component 606 is attached or coupled to the second component 604. Attachment may be facilitated by any suitable means including mating threads 622, 614 on respective components. Sections of a container may be held together by any means or mechanical mechanism, including but not limited to an adhesive, a lock-and-key, a clip, a clamp, a magnetic closure, screw threads, and a tape.

The container 600 may also include a third component 608 housed within the closed container. The third component 608 can be placed around the implant 300 such that an inner surface of the third component 608 contacts an outer surface of the implant 300. The third component 608 may partially or completely surround the outer surface of the implant 300.

In some embodiments, the third component 608 also may support, maintain, and/or conform the shape or form of the implant when attached to, surrounding, or engaged to the implant 300. In other embodiments, the third component 608 may be part of the first or second component.

As described, in some embodiments, the third component 608 may be a shaper that provides shaping support to an attached implant. Although described as a component of the container, the device 608 does not have be part of a container. In some embodiments, the device 608 can be a shaper that is not a component of any other article. Instead, the device 608 can be used as a shaper directly with the implant without the device 608 being part of an implant container. Additionally, the non-container shaping device 608 may have any or all of the features or characteristics described in the embodiments herein except that the device 608 is not part of a container.

Figure 26A:
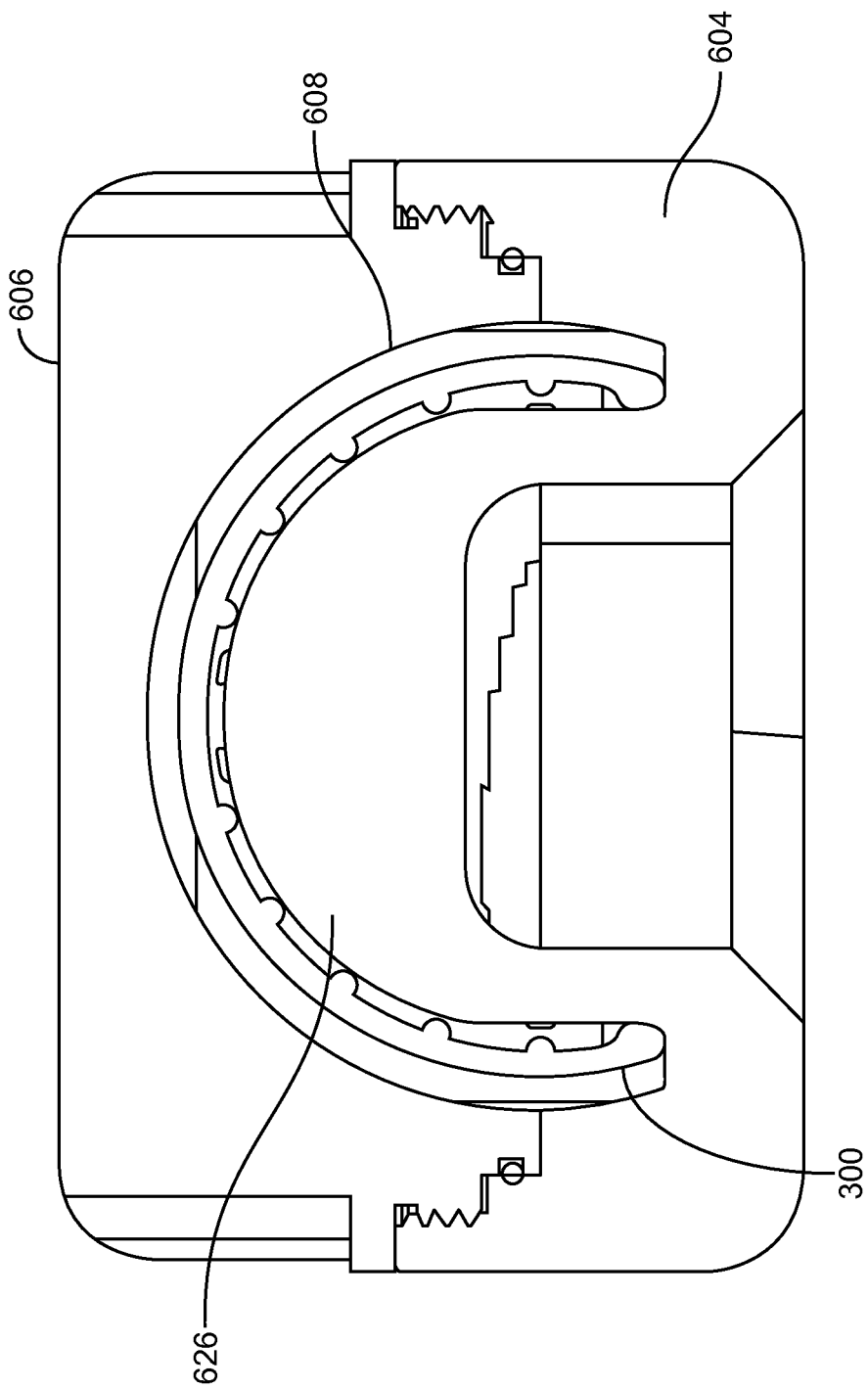
FIGS. 26A-B are cross-sectional views of the container in FIG. 25.
Figure 26B:
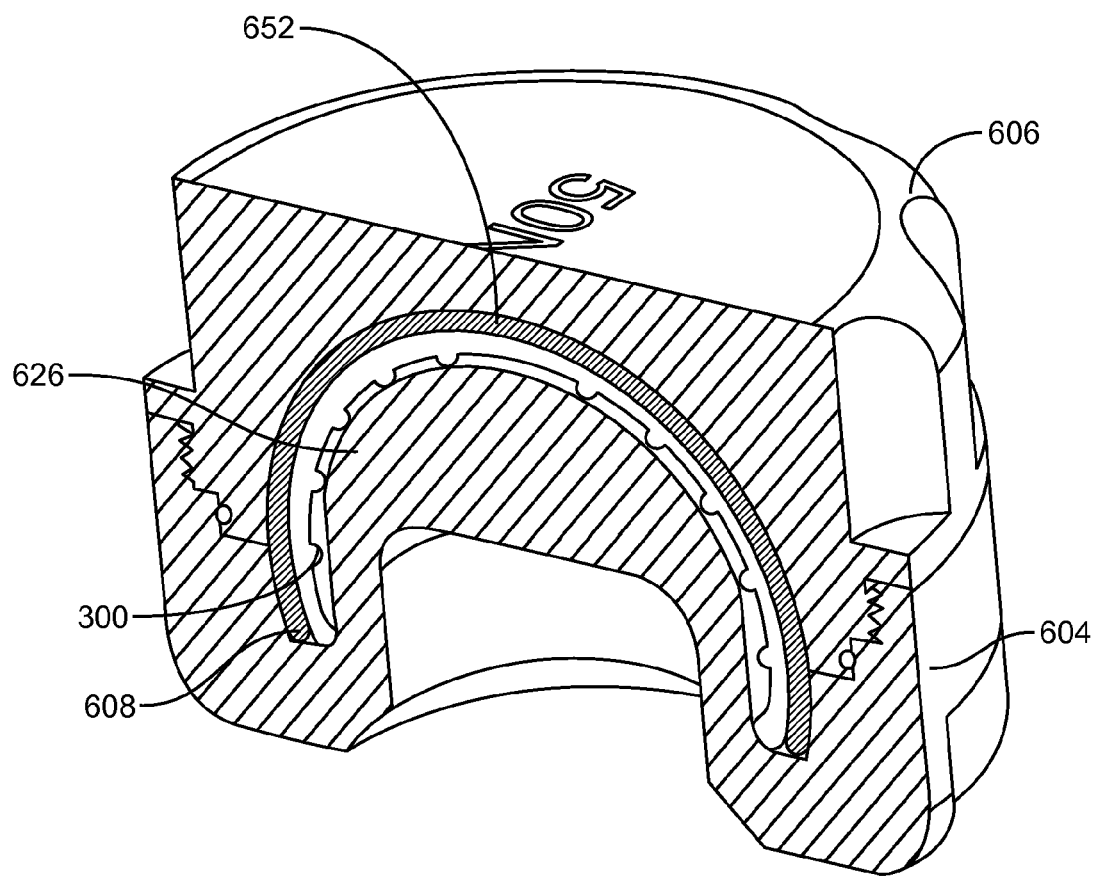

FIGS. 26A-B show cross-sectional views of the implant 300 enclosed within a container 600. As shown, the implant 300 is partially enclosed between a surface 626 of the second component 604 and a third component or shaper 608. In some embodiments, a section of the third component or shaper 608 may contain an opening or hole 652 allowing contact between the implant 300 and the first component 606. Alternatively, first component 606 may help to enclose the implant without directly contacting the implant 300. This may be the case even where the third component or shaper 608 has an opening. For example, the first component 606 may have an inner surface designed to receive the implant 300 without making direct contact by including space between the inner surface of the first component 606 and a surface of the implant 300.

FIGS. 26A-B also show a convex protruding surface 626 of the second component 604 inserted into a concave portion of the implant 300 where the convex protrusion 626 supports, maintains, or conforms the shape of the implant 300. Additionally, in some embodiments, the first component 606 has a concave inner surface for contact with the convex outer surface of an implant 300 or a third component 608.

Figure 27A:
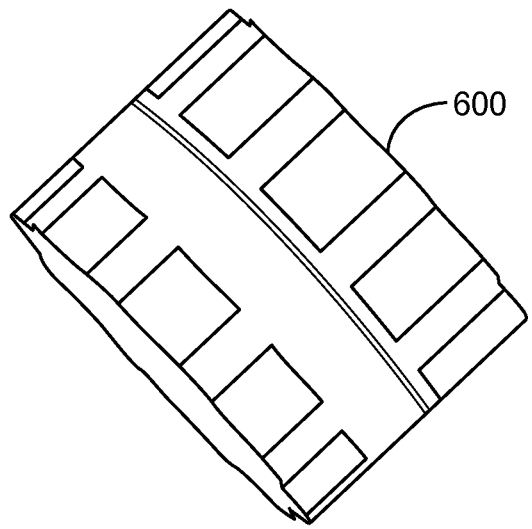
FIGS. 27A-B show an opened and closed implant container.
Figure 27B:
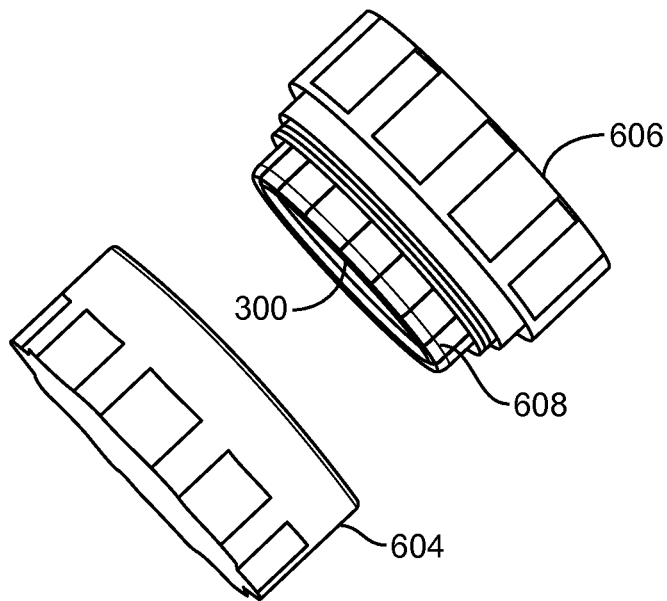

Referring to FIGS. 27A-B, during use, the second component 604 may be removed from the first component 606 and the third component/shaper 608. In other embodiments, the third component/shaper 608 is detachable from the second component 604 and/or first component 606. As shown, the third component/shaper 608 may be enclosed in the first component 606 when the container 600 is opened. In some cases, the third component/shaper 608 remains connected with an implant 300. In such cases, once the container is opened, the third component/shaper 608 may be removed from the first component 606.

Figure 28B:
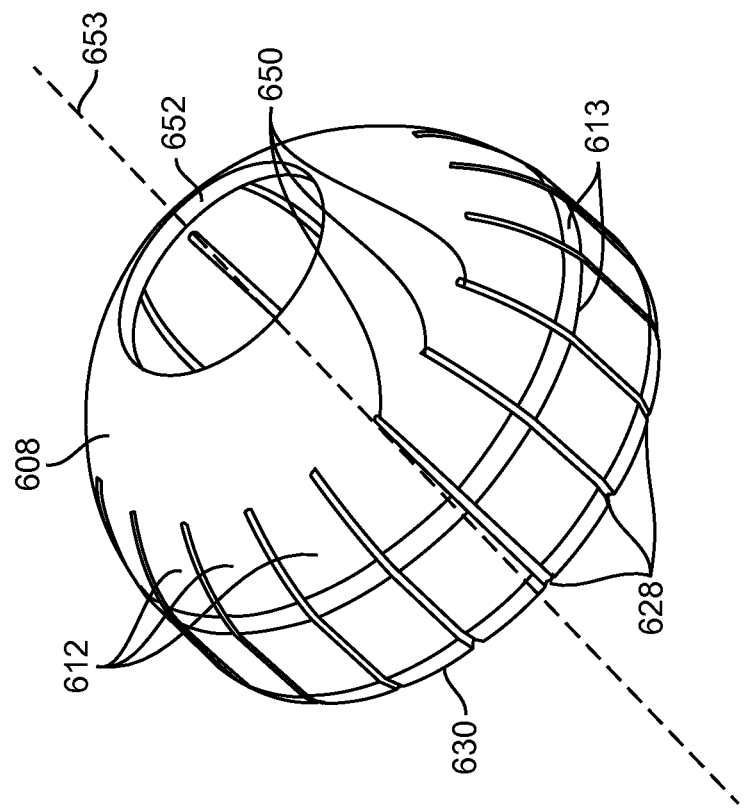
FIGS. 28A-B show a third component or shaper.
Figure 28A:
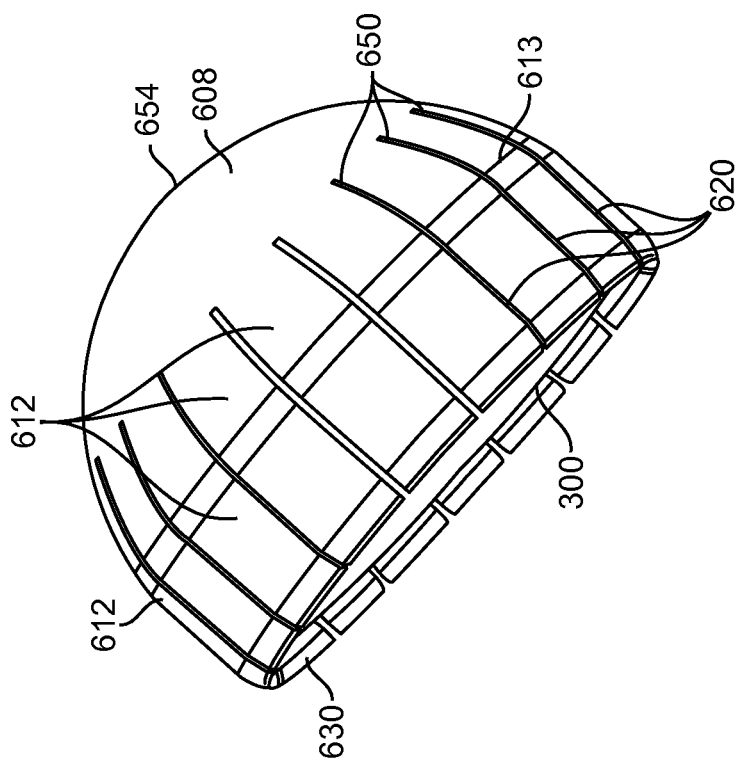

FIG. 28A shows the removed third component or shaper 608 connected to the implant 300. In some embodiments, the third component/shaper 608 may be split or scored. For example, FIGS. 28A-B show segmented members 612 placed around a circumference of the third component 608. Each of the segmented members 612 comprise a pair of longitudinal slots 620 with a first end 650 and a second end 628. The first end 650 is positioned along the longitudinal direction of the third component or shaper 608 and the second end positioned along a perimeter of the third component 608. In some embodiments, the third component or shaper 608 has a proximal opening 652 at a north pole 654 along a longitudinal axis 653 and a distal opening 630. A perimeter extends along the distal and proximal openings 630, 652. In some embodiments, the longitudinal slots 620 are positioned about 20 degrees apart from one another. In some embodiments, one or more slots may be at about 10, 20, 30 degrees apart. In other embodiments, the distance between the slots 620 is not uniform. In other cases, the length of the slots 620 may or may not be uniform relative to each other. In other embodiments, the first end 650 of each slot 612 may be proximally positioned from an opening 630 in the third component or shaper 608. In some cases, the first end 650 may be positioned distally from the north pole 654 or a perimeter around the proximal opening 652.

In further embodiments, the segmented members 612 allow an opening 630 of the third component or shaper 608 to open or expand radially. For example, the third component/shaper 608 may be split or segmented in the longitudinal direction anywhere from a few degrees from opening 630 to well beyond the equator, which allows for the third component to "open" transiently in the radial direction (like a claw or a petal on a flower). In further embodiments, the third component or shaper 608 includes resilient expandable members that allow the third component or shaper 608 to move from a first configuration to a radially expanded configuration. The resilient members may also allow the third component or shaper 608 to return to the first configuration after expansion. In some cases, the resilient members are biased toward the center of the third component or shaper 608. In further embodiments, the resilient members or expandable members allows an increase in the diameter of the third component or shaper 608 when radially expanded.

Figure 29B:
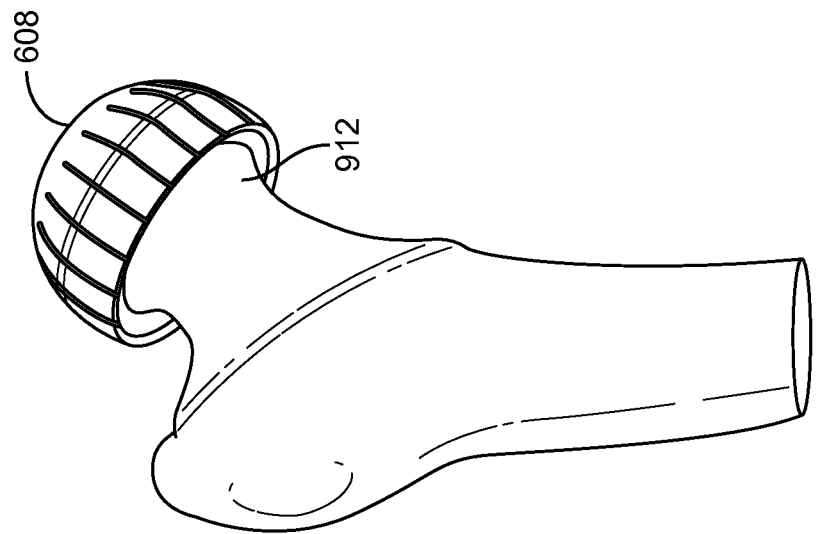
FIG. 29A-B show the assembly in FIG. 28A attached to a femoral head.
Figure 29A:
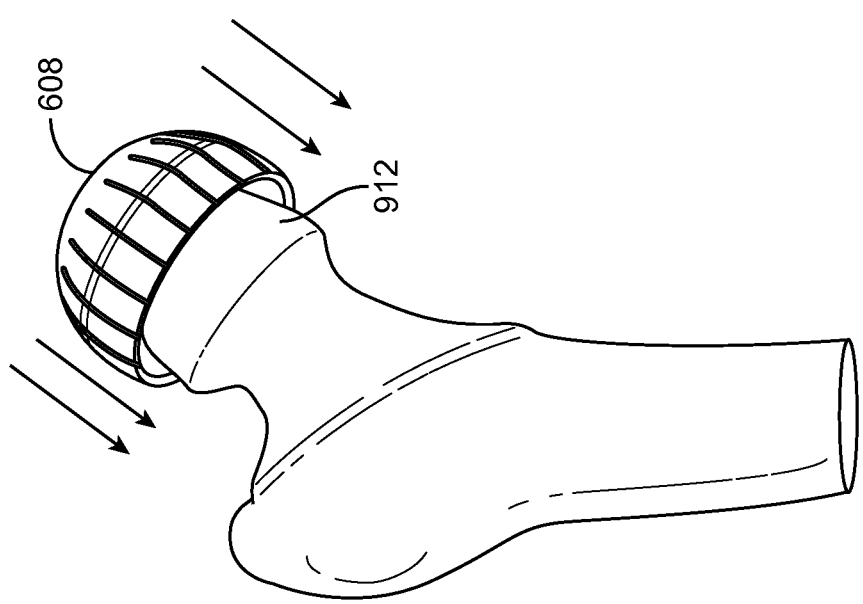

Additionally or alternatively, the third component or shaper 608 may include a plurality of slots, perforations, scores, seals, surface features, any other features or combinations thereof that allow the expanding, bending, or other size changes. In other embodiments, portions of the third component or shaper 608 may be hinged, connected, or attached at the north pole like a clam-shell, and may open as the implant 300 stretches out while being lowered over the femoral head and close afterwards to surround the implant and femoral head. The material of the third component or shaper 608 may be sufficiently flexible, resilient, or rigid to snap back into position after the transient deformation it undergoes. For example, FIGS. 29A-B show the third component or shaper 608 with attached implant 300 sliding over the femoral head 912.

In some embodiments, the shaper or third component 608 may comprise a spherical portion and a cylindrical portion. FIGS. 28A-B show an edge 613 between the spherical and cylindrical portions. In some embodiments, the edge 613 is positioned at the transition between the spherical and cylindrical sections.

As described, in some embodiments, the shaper 608 is a stand-alone device that is not a part of another device or a container. For example, the shaping device 608 shown in FIGS. 28A-B may be a part of a container as a component or may be a separate stand-alone device that is not part of a container. The shaper 608 may also be provided separate from or together with the implant. The implant may be provided in separate packaging and then attached to the shaper 608 for attachment to the target location. In other embodiments, the implant may be provided pre-attached to the shaper 608.

Figure 30:
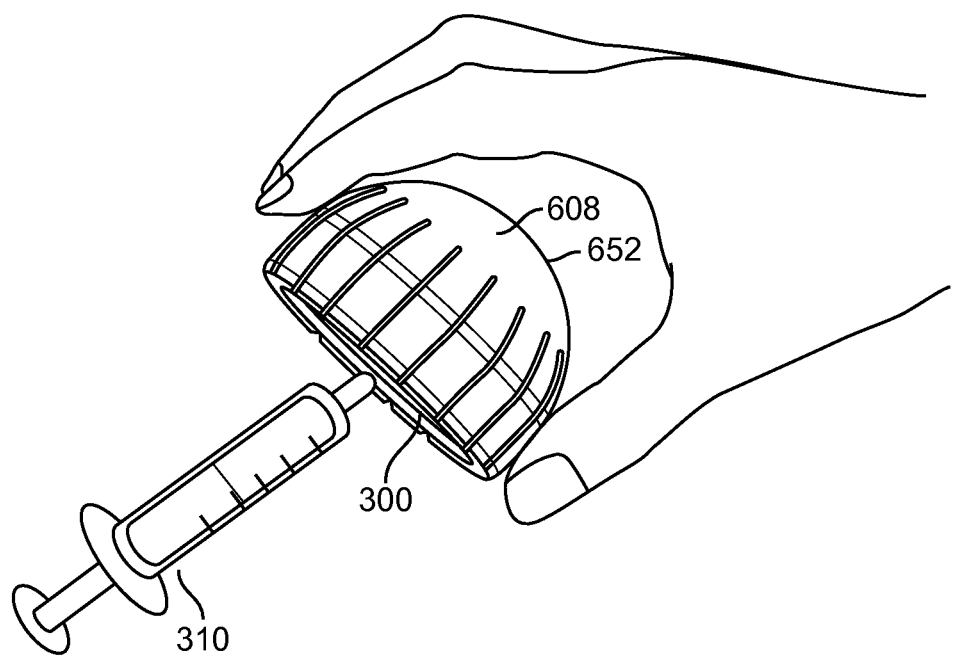
FIG. 30 illustrates adhesive application on an implant attached to a container component and/or shaper.

In use, the third component or shaper 608 with implant 300 is removed from the container 600. Alternatively, where a container is not used, the shaper 608 with implant 300 may be used alone. A curable adhesive or cement is applied to the surface of the implant that will contact a bone or joint surface (see FIG. 30). The affixing compound may also be applied to the surface of the bone directly instead of to the surface of the implant. Alternatively, the compound may be applied to both the implant and the bone surfaces.

Figure 31A:
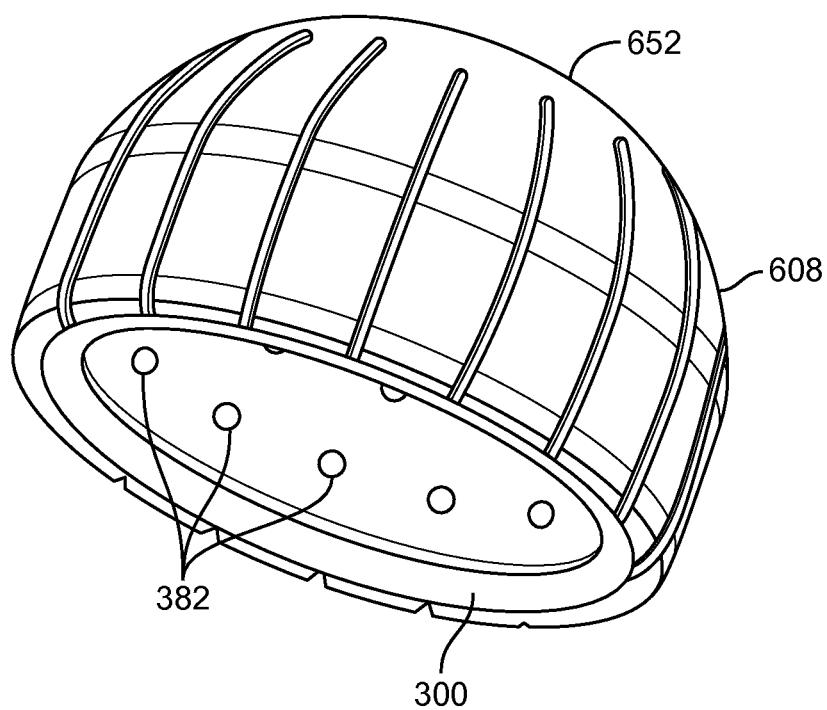
FIG. 31A shows the implant attached to a shaper and/or container component with proximal and distal openings.
Figure 31B:
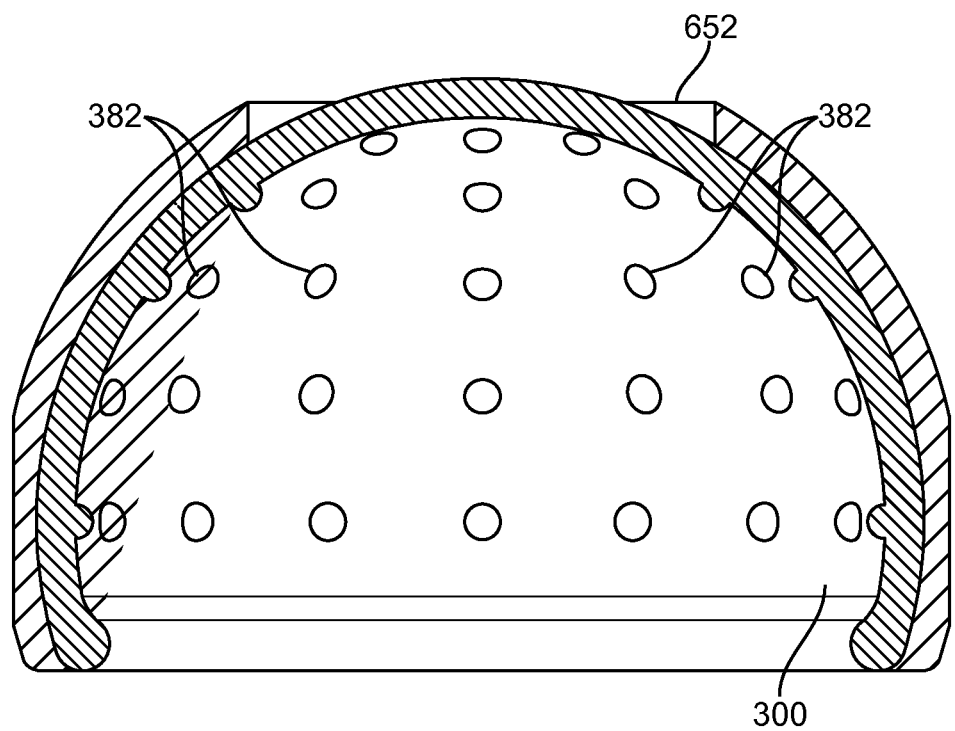
FIG. 31B is a cross-sectional view of the shaper and/or container component and implant in FIG. 31A.

FIGS. 31A-B show the third component or shaper 608 surrounding a femoral implant 300. In some embodiments, the femoral implant includes surface features such as bumps 382 to facilitate attachment to the target location. In further embodiments, the curable compound may be applied to the bone or joint surface directly. Additionally, the curable compound may be applied to both the target anatomical region as well as the implant.

In addition to maintain or supporting shape, the third component or shaping element 608 can protect a surface of the implant 300. For example, referring to FIGS. 28A-29B, the implant 300 has a convex outer surface that contacts an inner concave surface of the shaper/component 608. While covered by the shaper/component 608, the outer surface of the implant 300 is protected from damage.

As shown in FIG. 29A, the third component or shaper 608 with implant 300 may be placed directly onto the femoral head 912 once the curable adhesive or compound is applied to the implant surface. Oftentimes, there is a tendency for the anchoring compound to pool in a portion of the implant rather than evenly spreading across the implant surface. In such cases, an adhesive spreading device 1000 is a delivery instrument/tool that may be used to distribute the adhesive more evenly on the implant surface.

Figure 32:
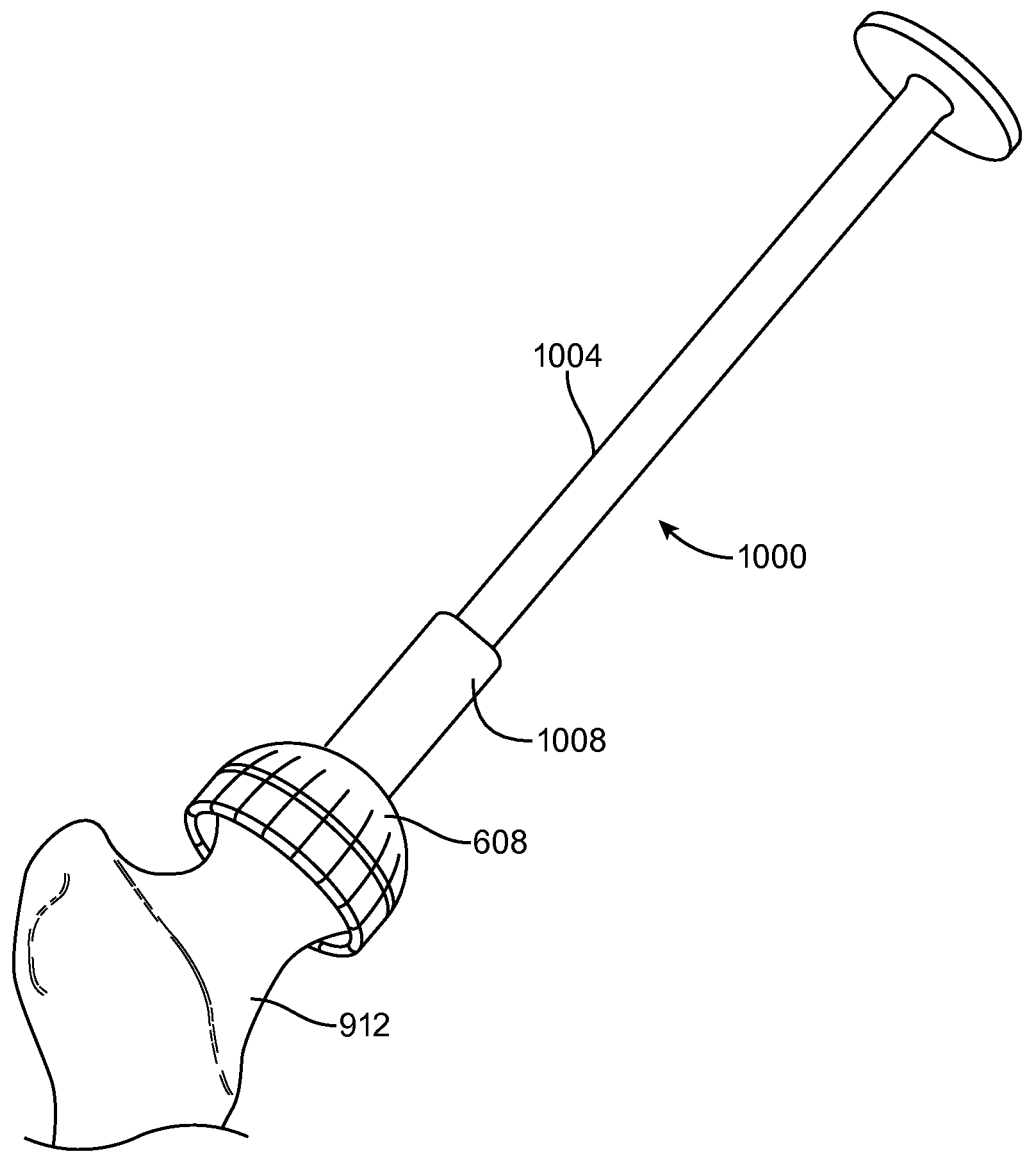
FIG. 32 shows an exemplary adhesive spreading device.
Figure 33:
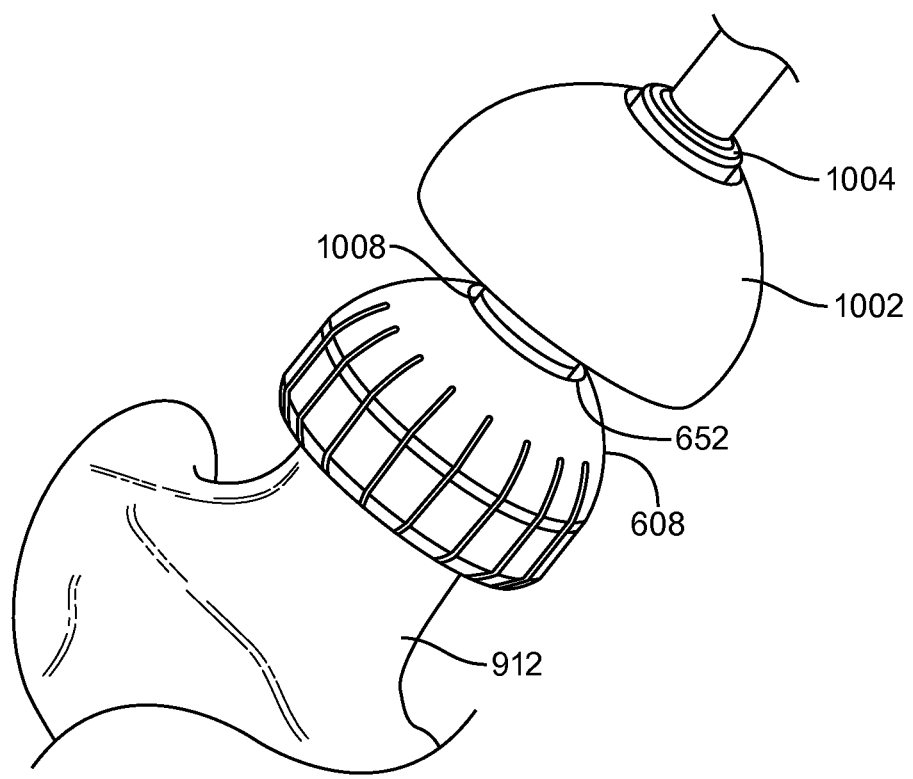
FIG. 33 shows an adhesive spreading device with a plunger according to described embodiments.
Figure 34:
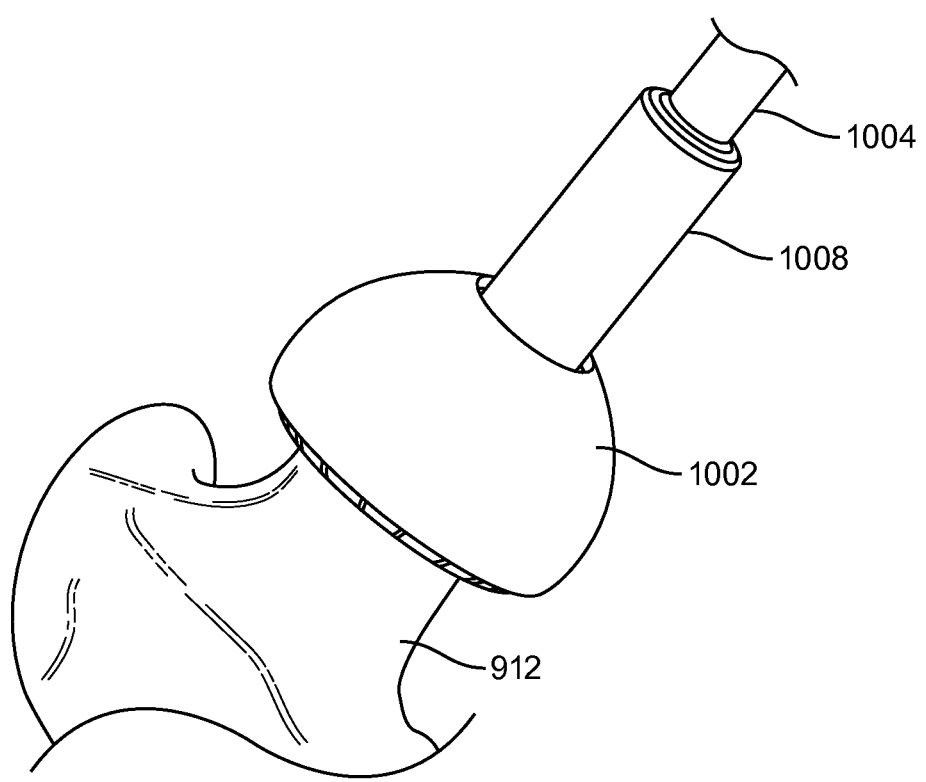
FIG. 34 shows the adhesive spreading device of FIG. 33 covering a shaper and/or container component attached to an implant.
Figure 35:
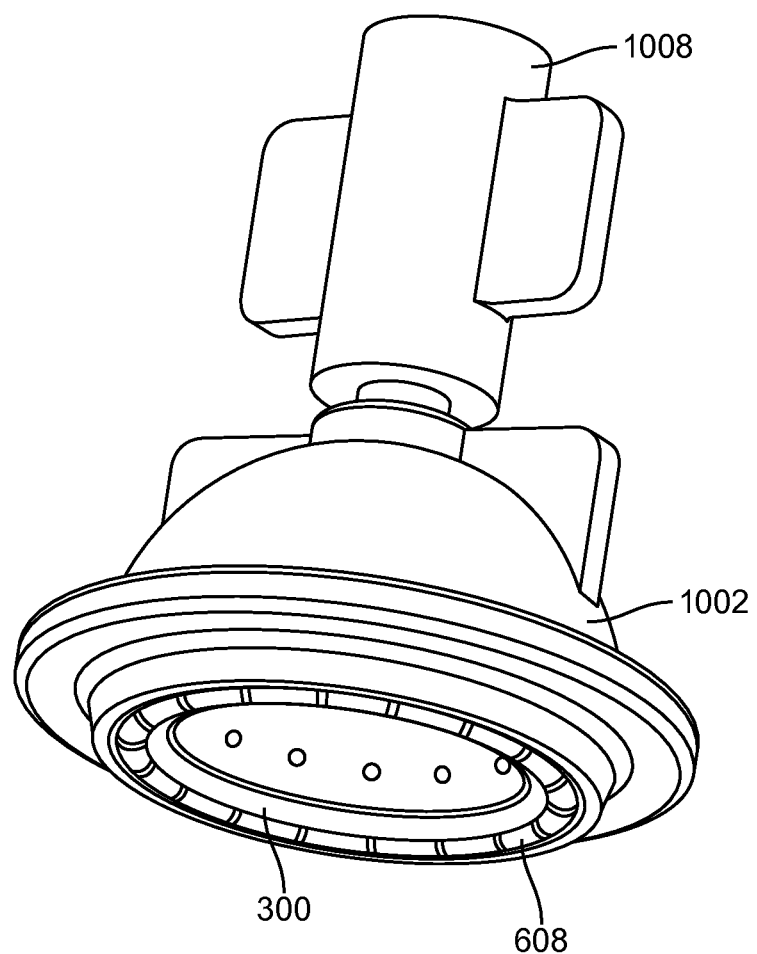
FIG. 35 shows an adhesive spreading device according to other embodiments described.

FIGS. 32-34 show one embodiment of an adhesive spreading device 1000. FIG. 32 shows an adhesive spreading device 1000 having a handle 1004 and a head 1008. The handle 1004 may comprise an elongate shaft or arm that is connected to the head 1008. The head 1008 may have a greater width compared to the handle 1004. A surface of the head 1008 distal to the handle 1004 may be adapted to contact the implant 300 directly or indirectly through the third component or shaper 608. In some embodiments, the implant is partially or completely enclosed in a shaping member such as the third component or shaper 608 described while the adhesive spreading device 1000 is used. In other embodiments, the third component or shaper 608 has a north pole 654 (as described above) about which a proximal opening 652 is centered. The head 1008 of the spreading device 1000 may have a size configured to allow a portion of the head to contact the implant by passing through the proximal opening 652. FIG. 33 shows the head 1008 inserted through the proximal opening 652 to contact the implant 300.

Referring again to FIG. 32, a user can apply force to the implant surface by pushing down on the adhesive spreading device 1000. While the spreading device 1000 is contacting the implant 300 through proximal opening 652, the user can apply a distally directed force toward the femoral head. This distally directed force pushes the implant against the femoral head such that adhesive that is deposited in the contact space between the femoral head and the implant will generally be squeezed outward from the center. As such, the adhesive will be spread across a greater surface area.

In some embodiments, the distally directed pressure alone is not sufficient to adequately spread the adhesive. In such circumstances, a plunger may be used to further distribute the adhesive. FIG. 33 shows plunger 1002 attached to the head 1008 of the spreading device 1000. The plunger 1002 is attached such that it can move longitudinally along the head 1008 to cover the third component or shaper 608 with the implant 300 (or the implant alone). FIG. 34 shows the plunger 1002 at distal position covering the third component/shaper 608 on the femoral head 912. In some embodiments, the plunger 1002 applies a pressing or compressing force along a contact surface between the plunger 1002 and the implant 300 or the third component or shaper 608. The plunger 1002 may include an opening to allow movement of the plunger 1002 along the head 1008.

Figure 36:
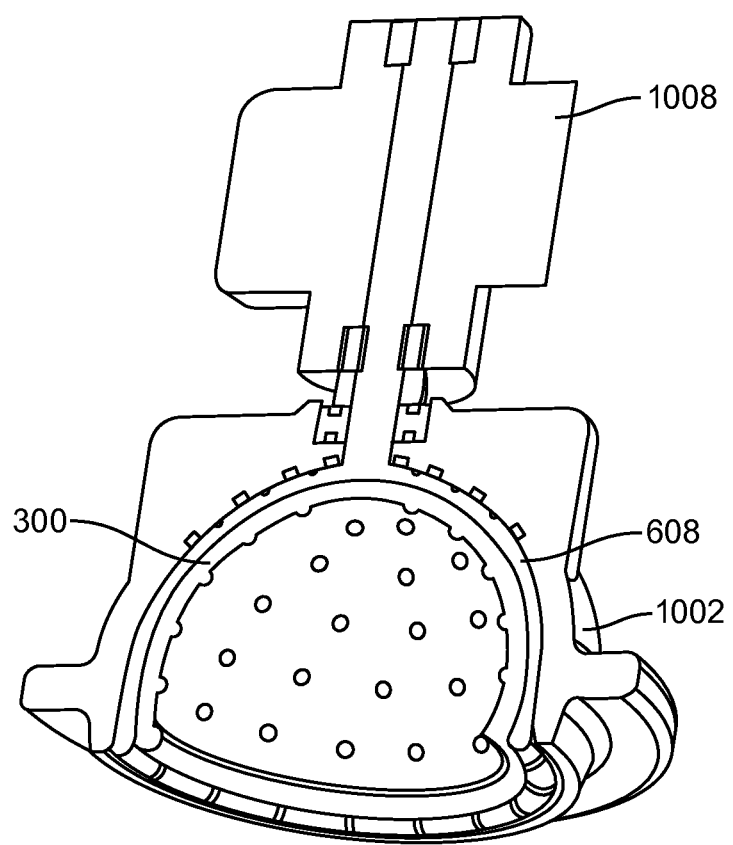
FIGS. 36-37 are cross-sectional views of the device in FIG. 35.
Figure 37:
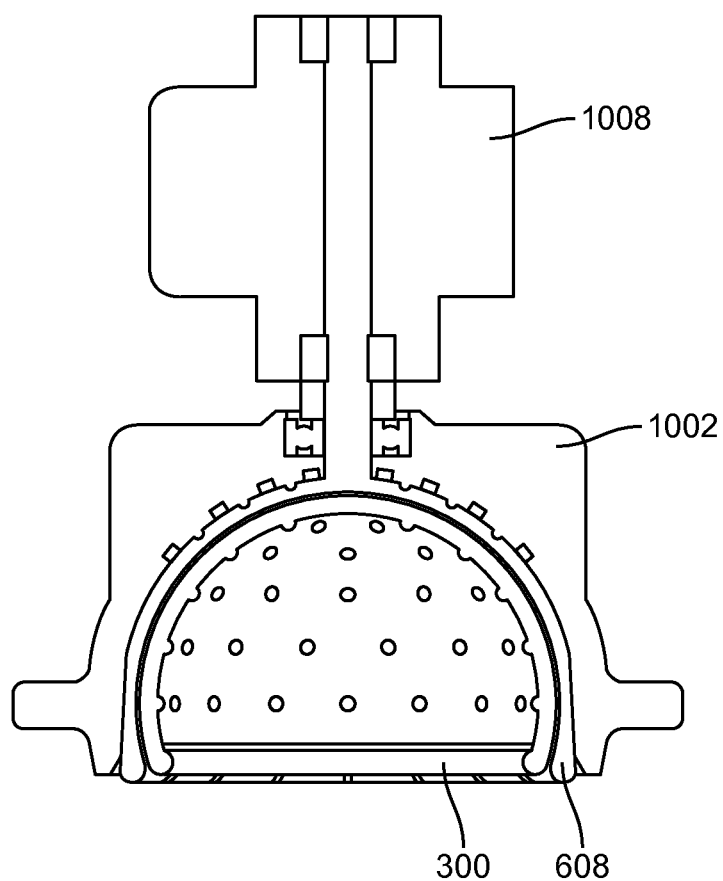
Figure 38:
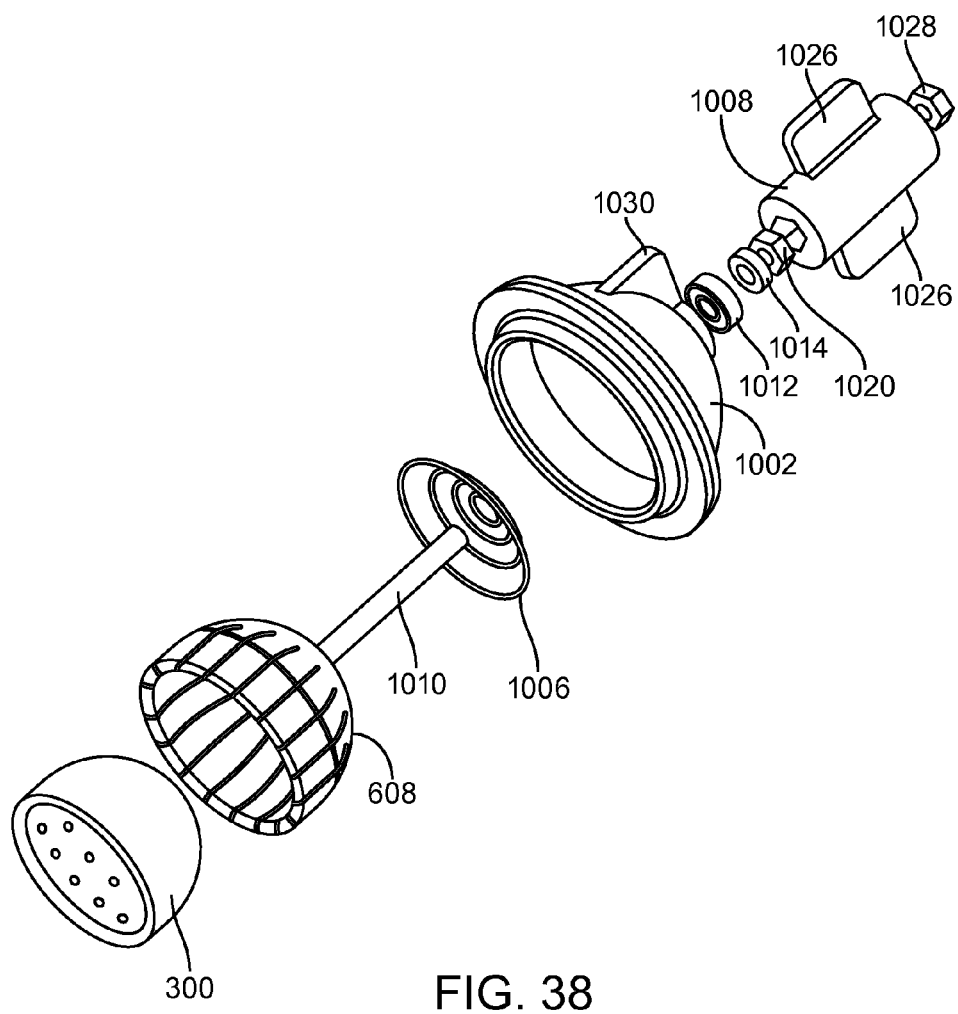
FIG. 38 is an exploded view of the components in the device shown in FIG. 35.
Figure 39:
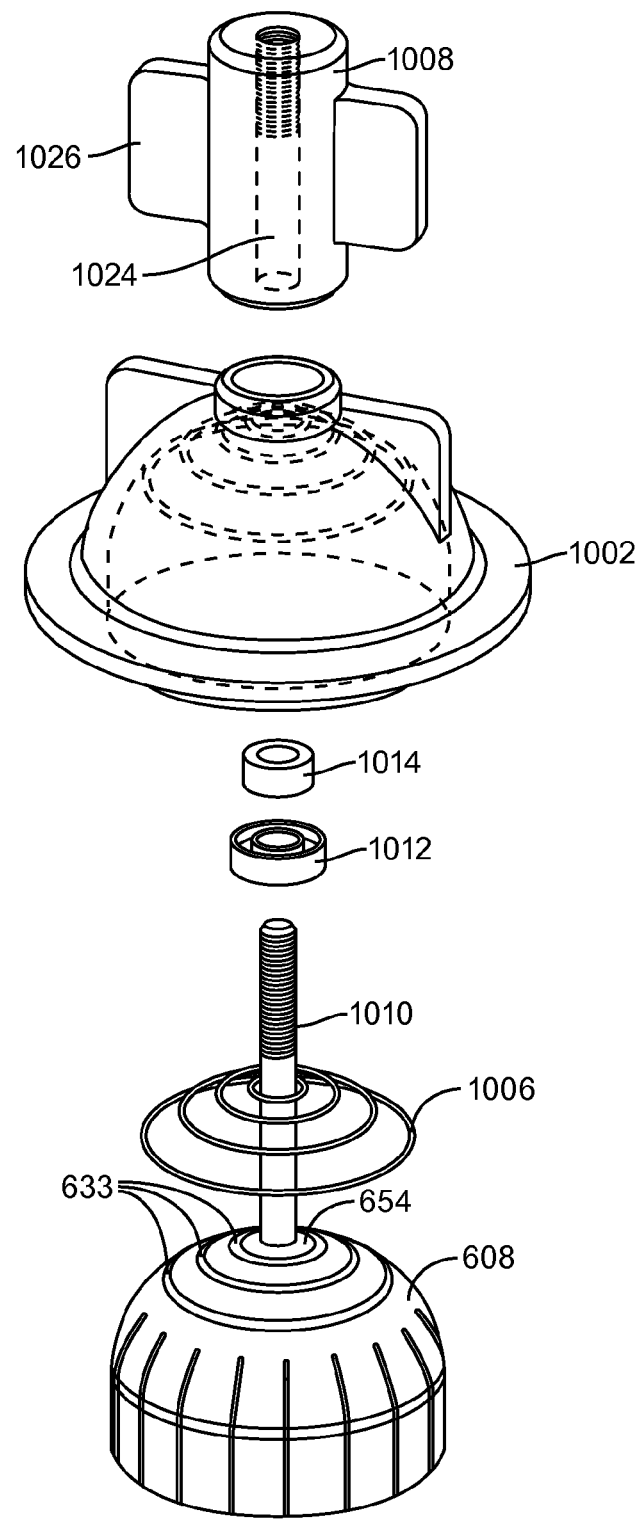
FIG. 39 shows unassembled components of the device shown in FIG. 35.
Figure 40:
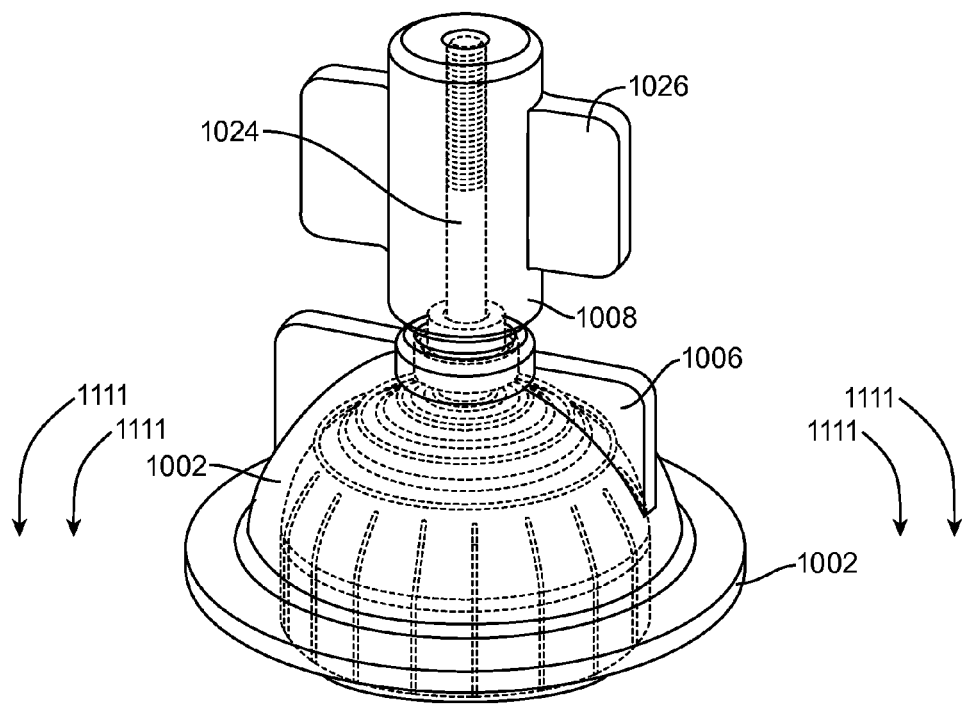
FIG. 40 shows assembled components of the device shown in FIG. 35.

FIGS. 35-40 show another embodiment of the spreading device 1000 with a plunger 1002. In this embodiment, the plunger 1002 is attached to a distal portion of the head 1008. The plunger 1002 can be sized and shaped to cover a shaper or container component 608 in which an implant 300 is attached. FIGS. 36-37 provide cross-sectional views of the plunger 1002, shaper or container component 608, and implant 300 assembly. FIGS. 38-40 show additional components connecting the plunger 1002 to the head 1008. The head 1008 may comprise a hollow shaft 1024 with mating threads. The plunger 1002 may be fastened to the head 1008 with a bolt or screw 1010 having corresponding mating threads. Any variety of washers 1014, nuts 1020 and 1028, and spacers 1012 may be used, as is understood in the art, to mechanically connect the head 1008 to the plunger 1002.

In some embodiments, a spring 1006 is positioned against an inner surface of the plunger 1002. The spring 1006 is configured to abut the inner surface of the plunger 1002 as well as any surface upon which the plunger 1002 is applied. The spring 1006 may be attached to the spreading device 1000 by way of the bolt 1010 and/or any additional nuts, washers, etc. In some embodiments, the shaper or container component 608 has surface grooves 633 or lines corresponding to the contour of the spring 1006. When pressed against the shaper or container component 608, the spring 1006 fits into the grooves 633. The spring 1006 assists in distributing applied forces along the surface surrounding the north pole 654. As shown in the embodiment of FIGS. 35-40, the shaper or container component 608 does not have an opening around the north pole 654. Rather, the spreading device 1000 contacts the shaper or container component 608 without contacting the implant 300.

Additionally, the head 1008 and plunger 1002 may include flanges 1026 and 1030 respectively. A user may hold onto flanges 1026 or 1030 to help manipulate the spreading device 1000.

When used, a surgeon may maneuver the spreading device 1000 of FIGS. 35-40 to a joint space having a shaper or container component 608 with attached implant 300 on a femoral head 912. The surgeon then places the plunger 1002 over the shaper or container component 608 and exerts a distal force against the shaper or container component 608. The plunger 1002 is adapted to slide over the shaper or container component 608 and apply a pressing or pushing force against the shaper or container component 608 and implant 300. Lines 1111 show the direction of the force in some embodiments. The pressing or pushing force applied helps to spreads the adhesive more evenly on the implant surface and femoral head.

Figure 41:
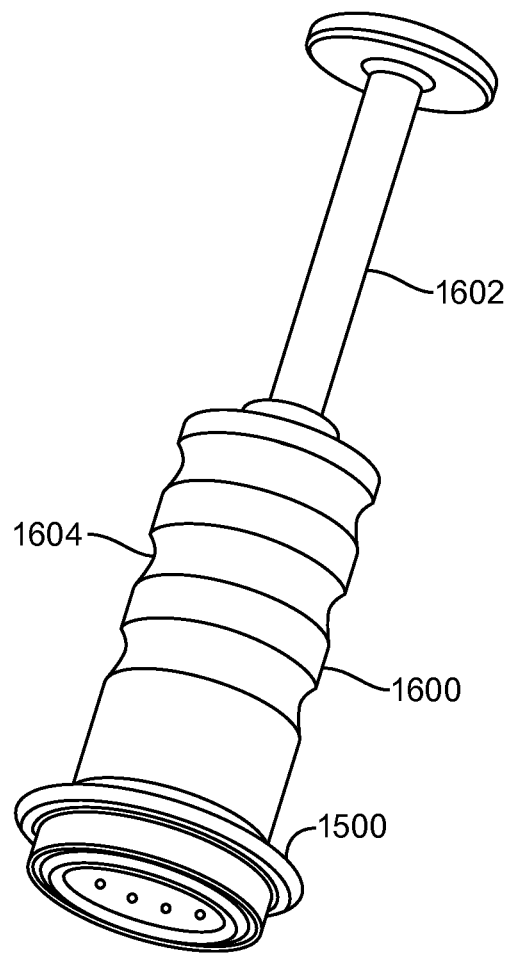
FIG. 41 shows an adhesive spreading tool according to some embodiments.
Figure 42:
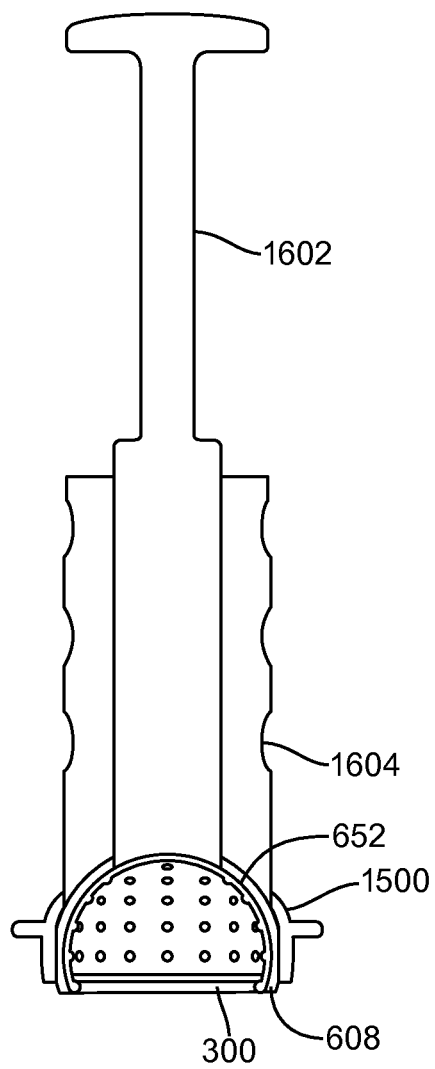
FIG. 42 is a cross-sectional view of the adhesive spreading tool shown in FIG. 41.

FIGS. 41-42 show an alternative delivery tool that can be used as an adhesive spreader. The spreading device 1600 has a handle 1602 with an outer collar or sleeve 1604. The outer sleeve 1604 may include gripping indentations or members to facilitate manipulation of the tool. The spreading device 1600 may fit onto a shaper or container component 608 with an attached implant 300. The shaper or container component 608 may have a proximal opening 652 (or may not). Applying force distally against the shaper or container component 608 assists in distributing the adhesive more evenly on the implant and joint surfaces.

In embodiments, the handle 1602 is used first to apply force to the implant 300 through opening 652 to move the curable compound or adhesive outwardly from the north pole toward the periphery of the implant. Then, the outer sleeve 1604 may be used to move the compound towards the equator of the implant. Additionally, an outer ring 1500 may be applied to move the curable compound from the equator to the distal opening of the implant.

In any of the described adhesive spreading devices, the devices may include a plunger element having a diameter between about 30 mm and about 60 mm. In some cases, the plunger element has a diameter between about 38 mm and about 60 mm.

Figure 43:
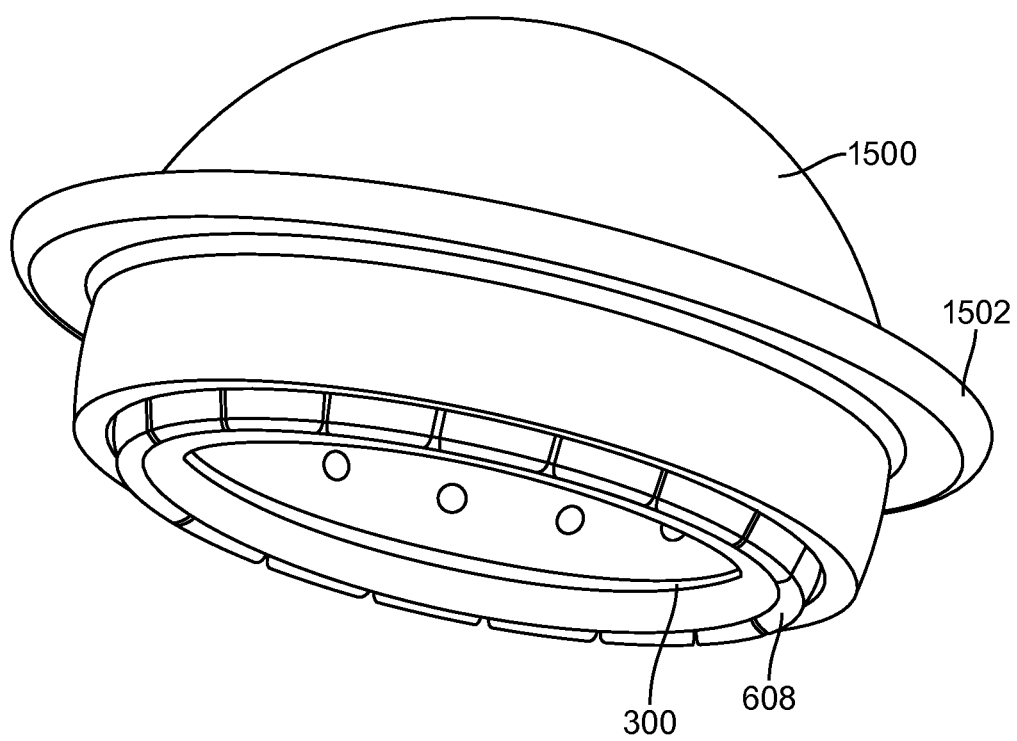
FIG. 43 shows a form mold according to some embodiments.
Figure 44:
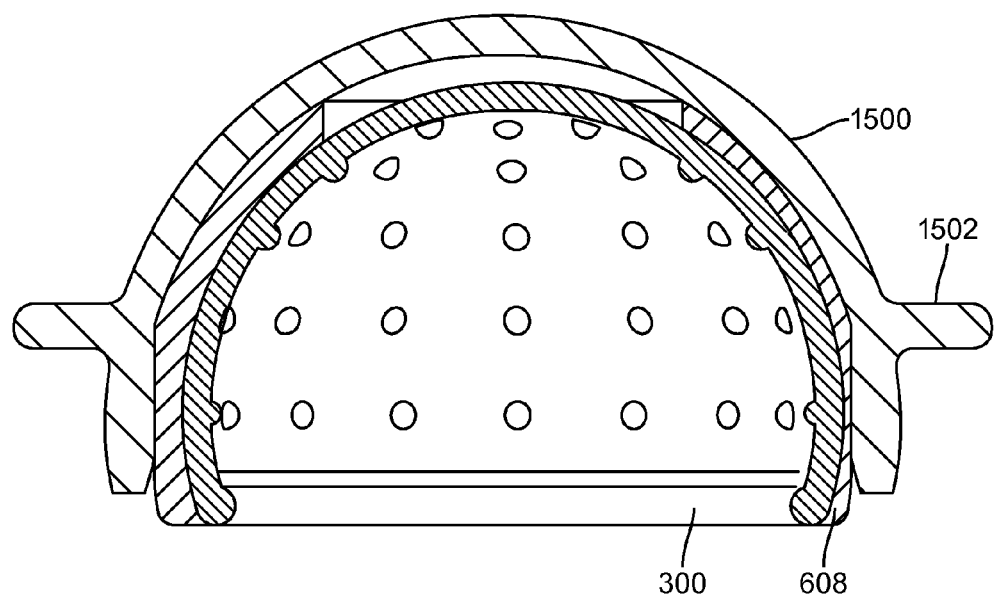
FIG. 44 is a cross-sectional view of the form mold shown in FIG. 43.
Figure 45:
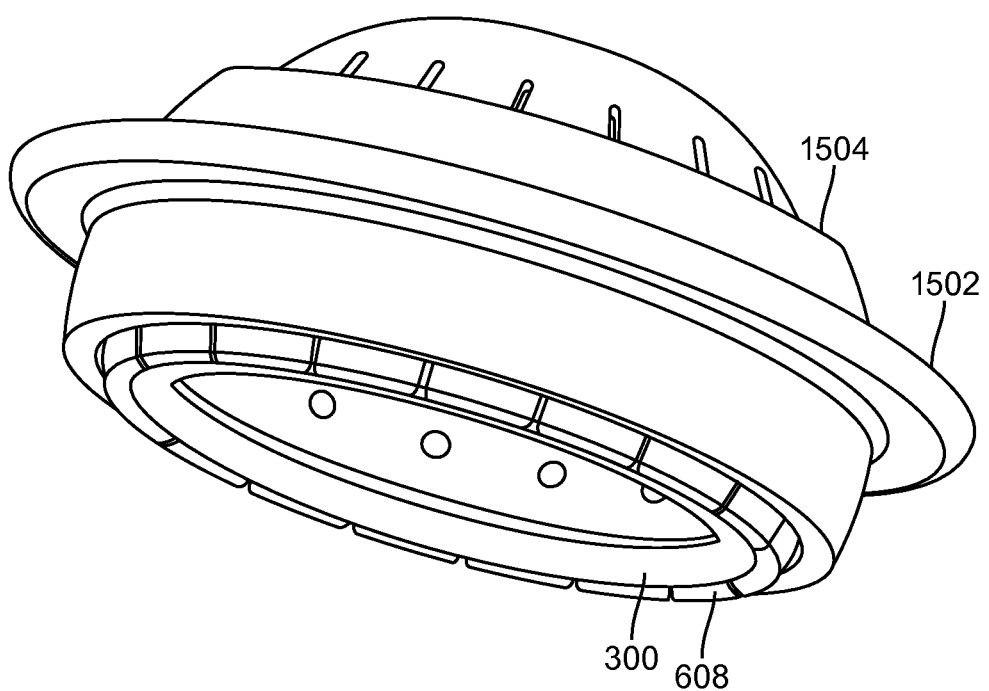
FIG. 45 shows a form mold according to other embodiments described.
Figure 46:
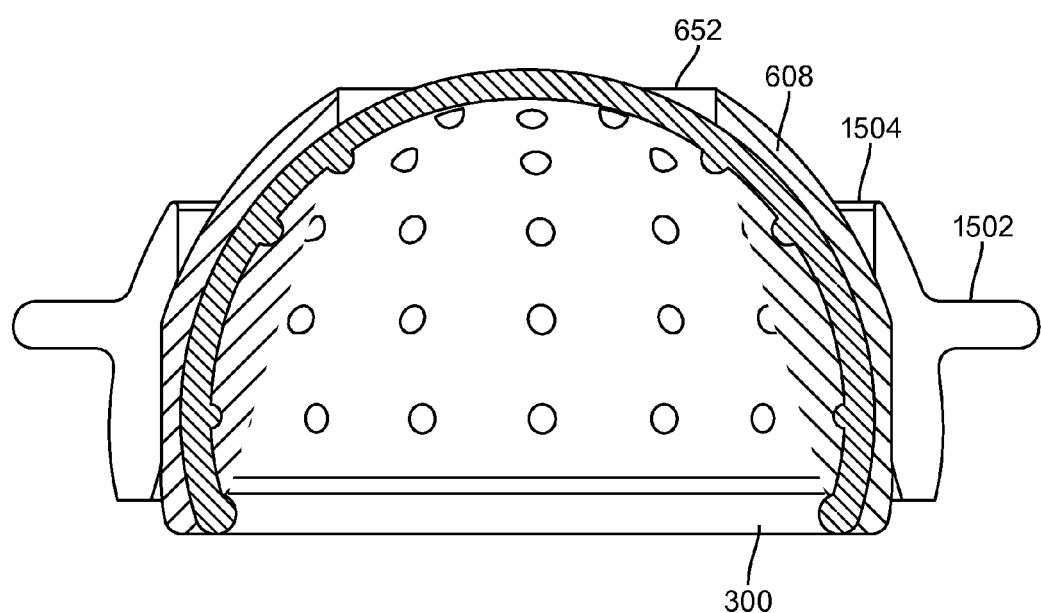
FIG. 46 is a cross-sectional view of the form mold shown in FIG. 45.

In some embodiments, as mentioned above, an additional form mold 1500 may be used to support, maintain, or conform the shape of the implant at the implantation site. FIGS. 43-44 show a hemispherical convex form mold 1500 that is configured to cover and surround the shaper or container component 608. The form mold 1500 may include a lip or flange 1502. In alternative embodiment, shown in FIGS. 45-46, the form mold 1500 comprises a ring 1504 surrounding a portion of the shaper or container component 608. The form mold 1500 and ring 1504 are removably attachable to an adhesive spreading device 1600.

Figure 47:
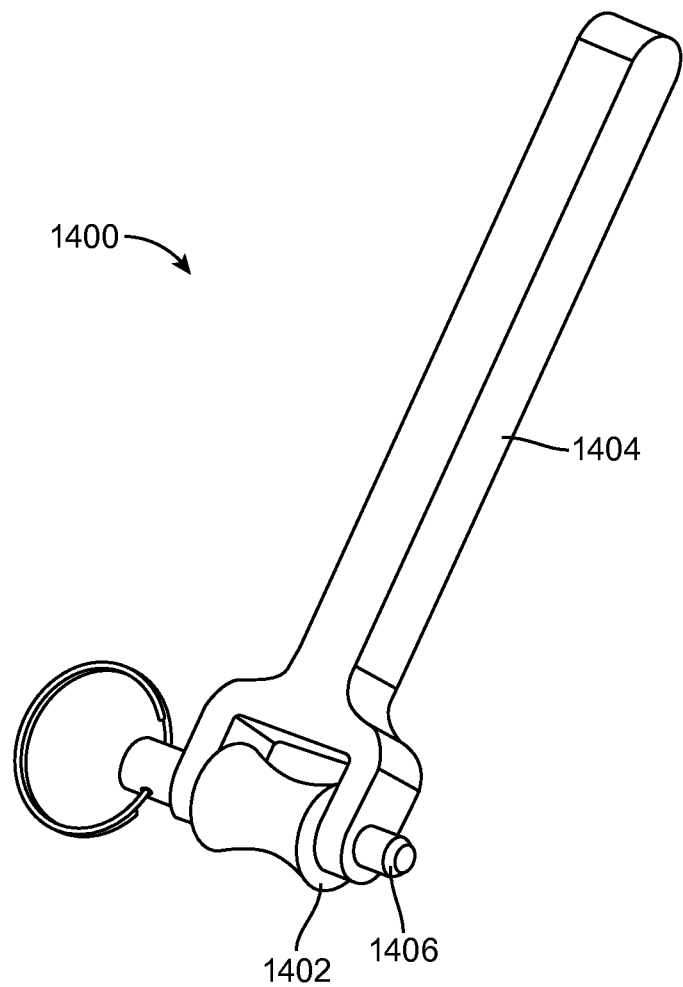
FIG. 47 shows a rolling device.
Figure 48:
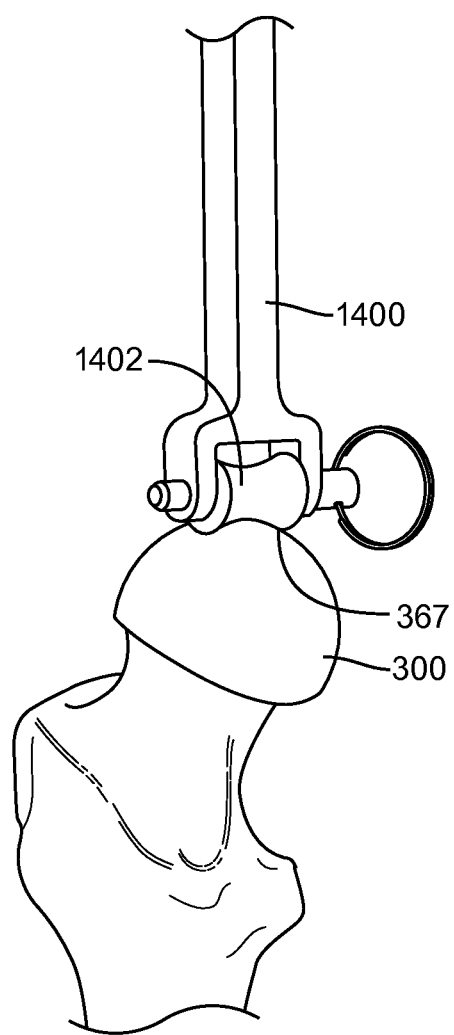
FIG. 48 shows the rolling device of FIG. 47 applied to an implant.
Figure 49:
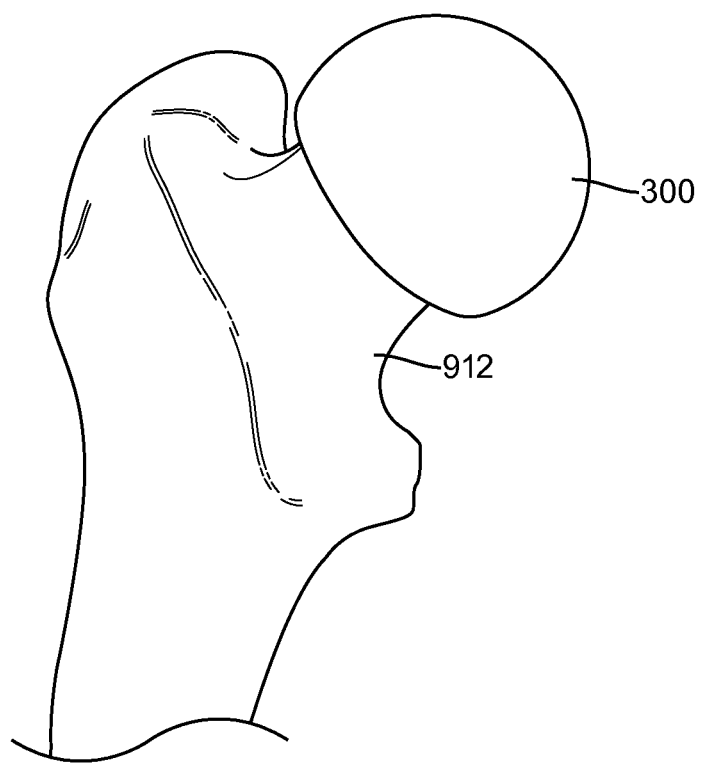
FIG. 49 shows an attached implant.

FIGS. 47-50 show alternative embodiments for spreading a compound along a surface of an implant. For example, FIGS. 47-48 show a spreading device 1400 with a roller 1402 attached to a handle 1404 by a pin 1406. The roller 1402 has a curved surface configured to accommodate a convex surface of a femoral head implant. The roller 1402 can apply a force in a top-down direction starting from the north pole 367 of the implant. The rolling force distributes adhesive pooled near the north pole 367 down the sides of the implant 300. Although shown as a roller 1402 contacting the implant 300 directly, the contact can be indirect through a container or shaper holding the implant. Additionally, the rolling may take place in any direction to spread the adhesive.

Alternatively, the roller 1402 may have a surface for accommodating any anatomical region or location. For example, the roller may have a surface for accommodating the concave surface of the acetabular cavity. The roller may have a rounded convex shape.

In some embodiments, the rolling device spreads the adhesive by first applying a force against a first implant surface about a north pole of an implant in contact with a curable compound, wherein the force is distally directed relative to the north pole. This force is directed onto the north pole area toward the underlying bone surface. Then another force is applied to spread the adhesive down the sides of the implant. This force may be a top down force starting from a position proximal to the north pole to a position distal of the north pole. The top-down motion may be repeated as needed to roll over substantially the entire implant. In other words, for a spherical implant, the roller can roll from the north pole down to the opening, move over in a step-wise fashion to allow a top-down motion on a section next to the previously rolled section. This can be repeated until the surface area of the implant has been rolled over at least once. In some embodiments, the rolling force is applied indirectly to the implant because the roller is in contact with a shaping element such as the shaper or third component 608. The roller may roll over the third component's outer surface to indirectly apply a spreading force to the implant. In some case, the top-down motion goes from the north pole area to the equator of the implant or shaper. In other cases, the top-down motion travels from the north pole area to a perimeter of the distal opening 630. In some embodiments, the rolling is repeated to spread the curable compound across substantially a majority of the implant's surface in contact with the joint space.

Figure 50:
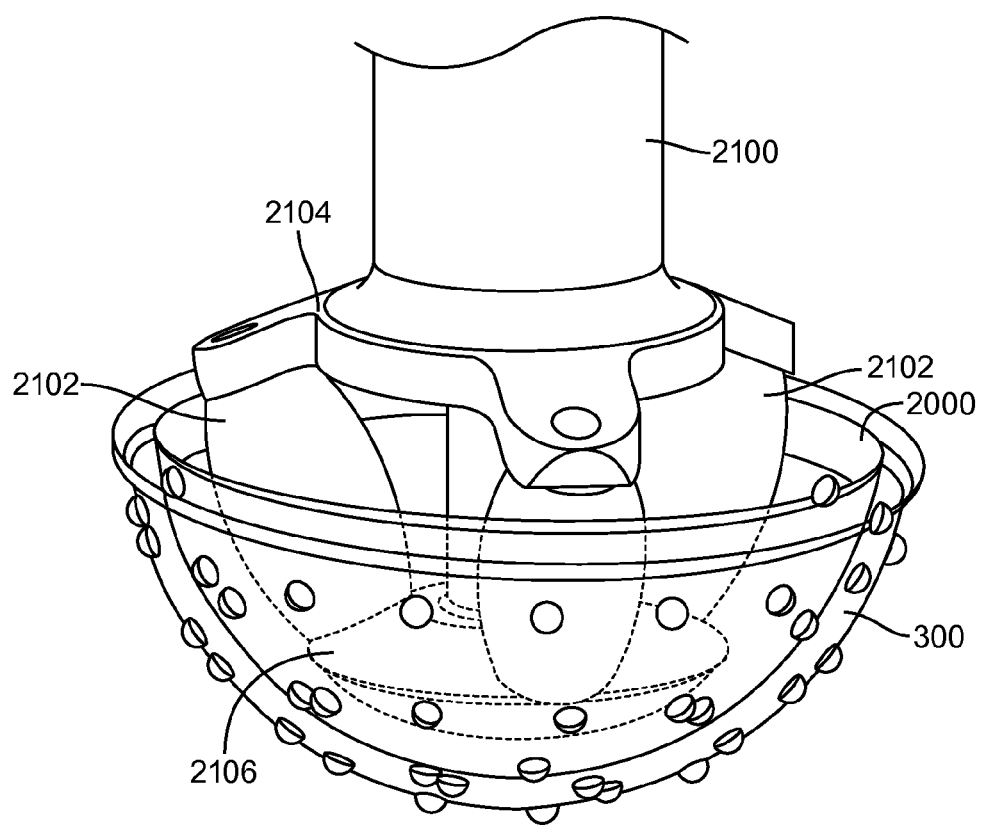
FIG. 50 shows an alternative rolling device.

FIG. 50 shows another embodiment of a rolling device 2100 for use with an implant having a concave inner surface and a convex bone contact surface. The rolling device 2100 includes a set of rollers 2102 attached to a base 2104 and a tip 2106. The rollers 2102 are attached at an angle such that a cross-section at the base 2104 is wider than a cross-section at the tip 2106. In some embodiments, a container component is in direct contact with the rollers 2102. In other embodiments, the rollers 2102 direct apply force against the inside 2000 of the implant 300. In other embodiments, the rolling device for use with a femoral head implant where the rollers contact the outer convex articular surface.

Although the spreading devices are described as being used on an implant that is already positioned at a target site, this is not required. In some embodiments, a container component with attached implant may first be connected to a delivery tool such as an adhesive spreading device prior to placement at an implantation site. For example, adhesive spreading device shown in FIGS. 35-40 with the container component 608, implant 300, and adhesive may be brought together for placement in a hip joint space. The spreading device can be used to maneuver the shaper or container component 608 and implant 300 onto the femoral head 912. This is advantageous where a thermally curable adhesive is used and body temperature at the joint site may start the curing process. Because the thermal curing process can begin immediately upon implant placement, some of the adhesive may already have cured before a spreading device has been connected to spread the adhesive along the surface of the implant. As such, embodiments contemplated include those which include an implant, container, and delivery tool (e.g. adhesive spreading tool) assembly for placement together into a joint.

In some embodiments, the curing may be initiated by temperature or heat. In other embodiments, curing may be initiated by particular temperatures such as about 37° C. or 50° C. For example, some standard PMMA bone cement are chemically initiated at room temperature. As discussed, the adhesive can be thermally, light, or chemically cured. FIGS. 51A-52B show embodiments of light delivery instrument that can be used with an implant having a convex outer surface. FIGS. 51A-B show an energy transmitting device 400 for transmitting light to a femoral implant 300 in a joint region. The device 400 has a handle 404 that can house a lightguide cable or a power cable 409. The device 400 has two opposing arms 402 attached at a distal end of the device 400. The two arms 402 have an open configuration shown in FIG. 51A and a closed configuration shown in the FIG. 51B. The two arms 402 can move from the open to closed configuration by pivoting along or about a hinge 408. In some embodiments, the opposing arms in the closed configuration form a substantially circular arc having an angle between about 180 degrees and about 270 degrees. In other embodiments, the substantially circular arc has an angle greater than about 180 degrees.

Energy (light) may be transmitted or emitted from anywhere (or through anywhere) along the apparatus 400. Energy (light) may be emitted from a distal portion or a distal end. Light may be emitted from one or more (e.g. from one to up to one, two, three, four, five hundred or more) bulbs and/or light emitting diodes (LEDs) 406. The LEDs 406 may be placed along a surface of the opposing arms 402. Any number of bulbs or LEDs can be arranged in any configuration or pattern. Energy (light) may be delivered in any configuration or pattern that provides energy (light). Light sources may be spaced apart from one another or may be spirally or radially arranged, including in concentric circles.

In some embodiments, the light source is remote from the light delivery instrument 400 and a lightguide cable transmits light from the source to the instrument. In other embodiments, the light source is on the light delivery instrument 400 and a power source is connected to the light delivery instrument through a cable 409. In further embodiments, the power source is self-contained on or in the light delivery instrument such as a battery pack.

FIG. 51B shows the application of light to a curable adhesive on the femoral head 912. In this example, the opposing arms 402 have a concave surface for fitting around the femoral head 912. The light delivery device 400 may deliver light directly to the adhesive through a thickness of the implant 300 or through a thickness of the implant 300 and an implant shaper. For example, a shaper or component 608 may be attached to support and maintain the shape of the implant while it is unanchored but in contact with the femoral head. The opposing arms 402 of the light device 402 may close around the shaper or container component 608. Once activated, the light device delivers light through a thickness of the shaper or container component 608 and a thickness of the implant 300 to reach the contact area between the implant 300 and the femoral head 912. Presumably, a curable adhesive is placed in that contact area and will begin curing once light is delivered.

In some embodiments, an energy source (e.g. light source) such as a light diffuser connects with or contacts the shaper or container component or implant to provide adhesive curing energy. The energy source may connect with some, most, or all of the implant, shaper or container component, or portions of both. The light diffuser may connect with less area than an entire surface of the implant and/or container component (or shaper) and may be configured to move and thereby cure different portions of the adhesive at different times. Preferably, however, the light diffuser connects with essentially the entire surface of a shaper or container component that also connects on its other side with the implant. The light diffuser may be a spring-loaded series of petals that contacts or surrounds the shaper or container component and/or implant.

In other embodiments, the light delivery instrument is configured to apply light evenly through the shaper or container component, through the implant, and onto the light-curable adhesive situated between the implant and the bone. In yet another embodiment, the shaper or container component itself may be made of an elastomeric material that is at least semi-transparent, such that the shaper or container component can expand or stretch along with the implant as the two are lowered over the femoral head. The shaper or container component and the implant may be made of semi-transparent, transparent, or translucent materials that allow the passage of light-curing energy through to the light-curable adhesive between the implant and bone.

Figure 52A:
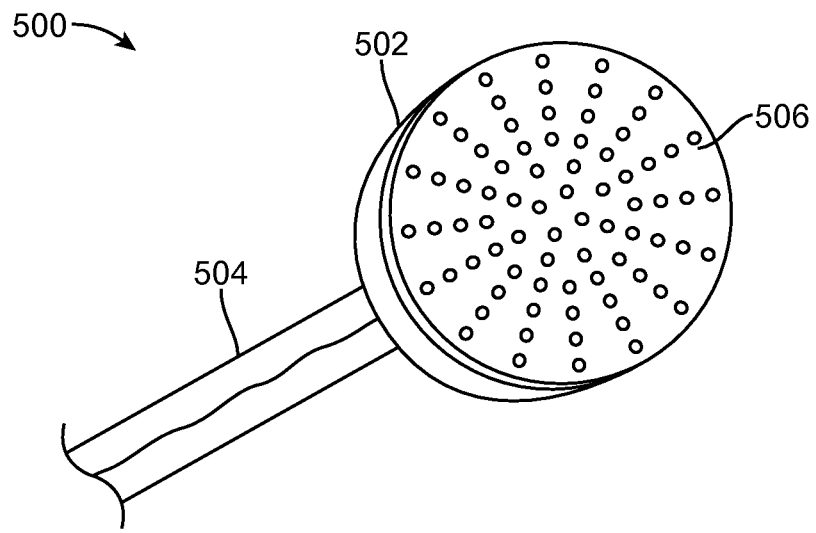
FIGS. 52A-B show a head of a device with a patterned arrangement of bulbs or LEDs for providing light to an acetabular joint region.
Figure 52B:
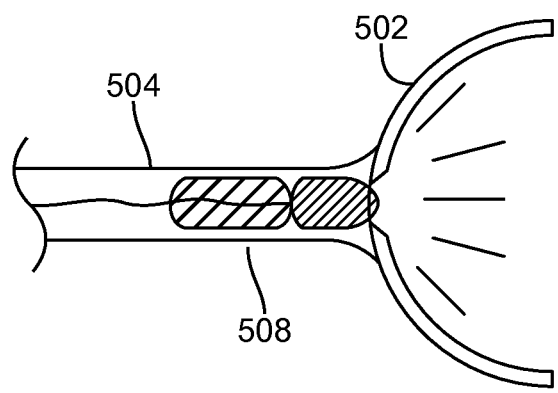

In further embodiments, the light delivery device may have a convex, concave, flat, and/or wedge shape at a light emitting end. A device may have light sources lined up in a radial configuration, a spiral configuration, along concentric circles, or in a grid pattern. For example, FIG. 52A shows an energy transmitting device 500 with a handle 504 and a distal head 502 having a regular pattern of bulbs or LEDS 506. Energy or light may be delivered or generated locally, and transmitted to a different region. FIG. 52B shows the device 500 with a light diffuser 508 for diffusing light into joint region such as an acetabular joint area.

Additionally, a bulb or LED can be configured to produce any amount of light useful for curing or treatment. A bulb or LED can have any shape and any dimension useful for treatment, including but not limited to circular, oblong, rectangular, curved, flat tipped, smooth tipped, pointy tipped. Light may come from LEDs, bulbs and/or light from a cable (e.g. a fiber optic cable). Light generated locally (e.g. from an LED and/or bulb) or traveled light (e.g. light from a fiber optic cable) may be used separately or together.

Furthermore, an energy (light) delivery instrument may be any size or any shape. It may be any size to connect with a joint region. It may be sized to fit within a joint region or to fit within (or near) a portion or a joint region, or it may be sized larger than a joint region as long as energy (light) may be delivered as desired.

A light source or light delivery device may be powered in any way. For example, power may be generated away from the system or may be generated or stored within the system. A light delivery device may be wireless and may have a stored (e.g. battery) energy (power) source. In one example, the device has a battery and may have a cylindrical, flashlight, or gun shaped light. Power may be delivered using one or more electrical cable(s). A cable may traverse a shaft of the light delivery instrument or may be outside a shaft.

Although the implant containers described have included two or three components, it can be appreciated that the containers may contain any number of subcomponents suitable. Additionally, in any of the embodiments contemplated, components of the container may have a cross-sectional diameter between about 38 mm to about 60 mm. Additionally, the cross-sectional diameter of a container component may be between about 30 mm and about 60 mm. Likewise, for a stand-alone shaper, the cross-sectional diameter may also be between about 38 mm to 60 mm and/or about 30 mm to 60 mm.

Figure 53A:
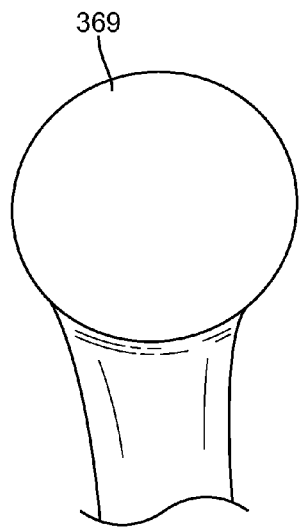
FIGS. 53A-C show implants for a shoulder joint.
Figure 53B:
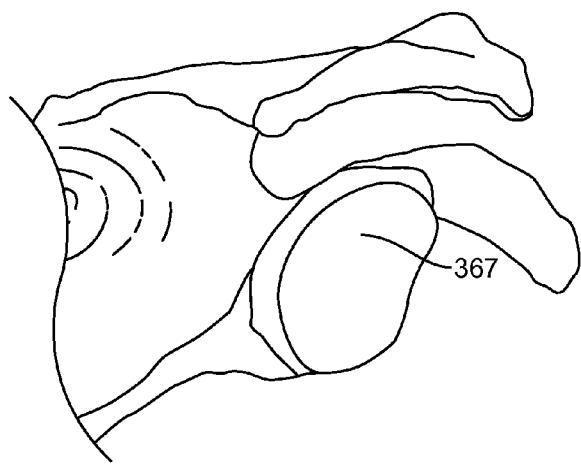
Figure 53C:
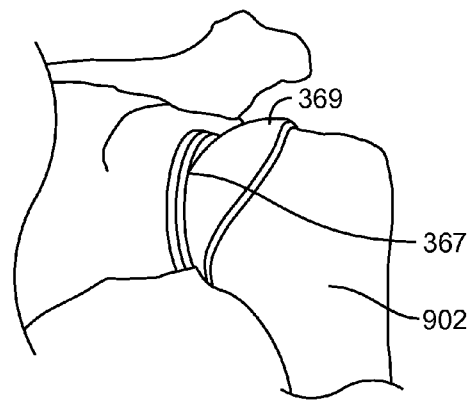
Figure 54A:
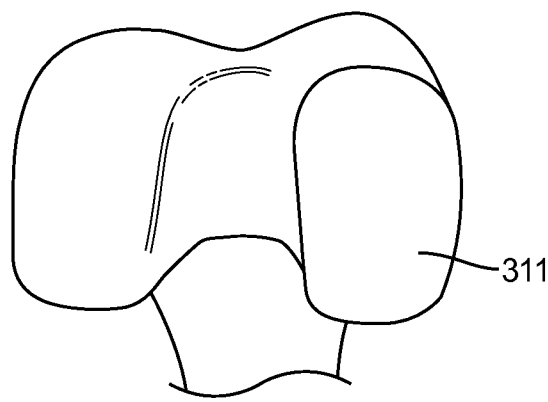
FIGS. 54A-B show implants for a knee joint.
Figure 54B:
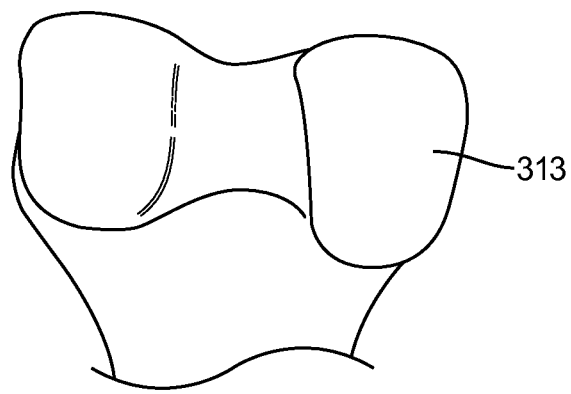

Additionally, acetabular and femoral head implants have been discussed as non-limiting examples above. However, any implant may be contained and anchored according to the methods, systems, and devices described. For example, FIGS. 53A-C show implants for a shoulder joint. Implant 369 is a humeral head implant that can be made from a flexible or compliant material. The humeral head implant 369 has a convex outer surface. Implant 367 is a shoulder socket or glenoid implant with a concave outer surface. FIG. 53C shows the humeral head implant 369 articulating with the glenoid implant 367 at the shoulder joint 902. As an additional example, FIGS. 54A-B show flexible implants for articular surfaces of the knee joint. FIG. 54A shows artificial cartilage implant 311 covering a condyle of the femur. FIG. 54B shows artificial cartilage implant 313 similarly covering a condyle of the tibia.

Figure 55:
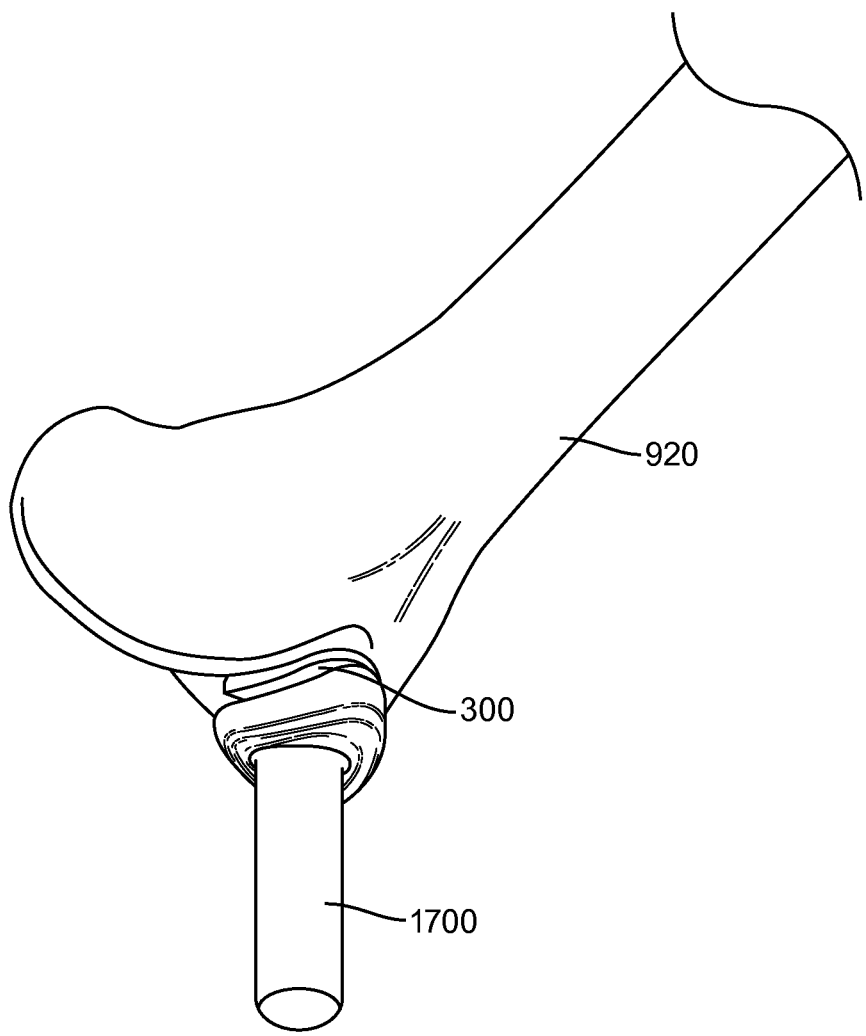
FIG. 55 shows application of an implant to a bone surface.

Regardless of the implantation location or the target site, the described implants and containers can be used in combination or alone with delivery tools described herein. FIG. 55 shows a delivery tool 1700 in contact with an implant 300 on an articulating surface of bone 920. The delivery tool 1700 is in direct contact with the implant 300 without a container component attached to the implant 300. In some embodiments, the delivery tool 1700 is also a shaping tool to allow the implant to conform or take on the shape of the underlying bone. In other embodiments, the delivery tool is a shaper that prescribes, forms, supports, or maintains the shape of the implant. For example, the delivery tool 1700 may be a shaper with a predetermined shape. When the delivery tool 1700 is placed against the implant 300 and forms the implant shape to the predetermined shape. In other embodiments, the delivery tool 1700 may shape the implant to shape of the underlying anatomical region.

Figure 56A:
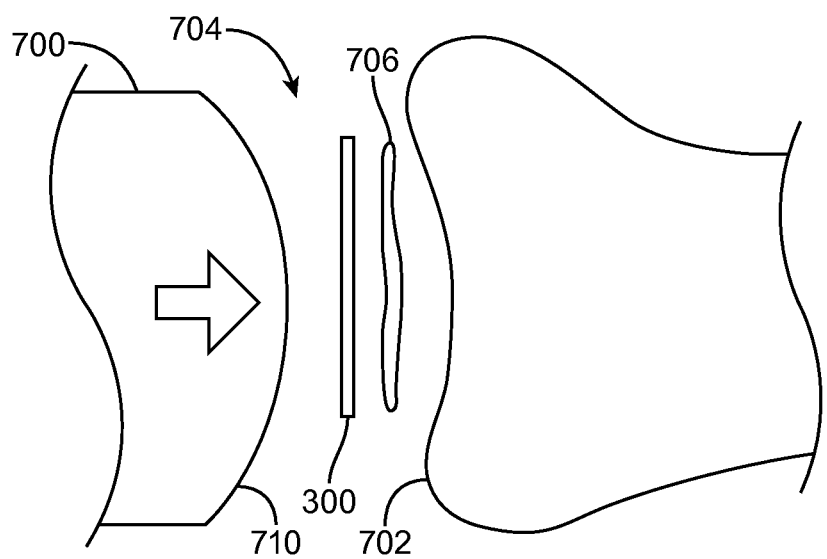
FIGS. 56A-B show a device and method for fixing a flexible, contour preserving cartilage replacement implant onto a bone.
Figure 56B:
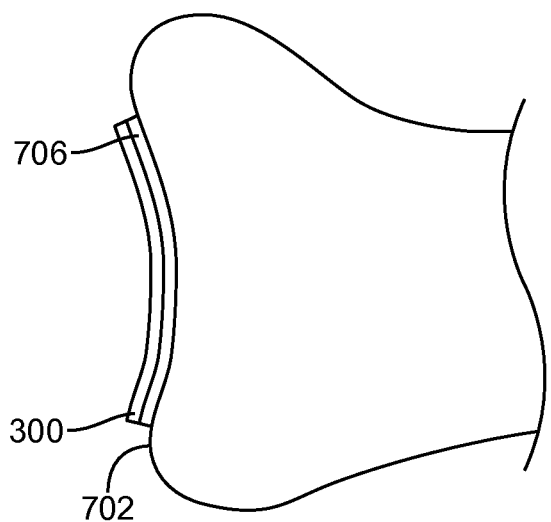

FIG. 56 shows another example of anchoring the implant 300 to a bone surface without an attached shaper. An implant 300 with adhesive 706 is applied to a joint surface of bone 702 of joint 704. The light delivery device 700 is brought into contact with the implant 300 as shown in FIG. 56B. The implant 300 is attached to the surface 702 by light-curing the adhesive 706. In this embodiment, the shape of the attached implant 300 is conformed to the bone surface 702 through the curing process. The light device has a convex surface 710 that assists in conforming the flexible implant 300 to the joint.

Additionally, an implant or coating may be cured onto a bone or joint surface with any of the described delivery instruments. For example, the implant or coating may have a pre-polymerization or curing structure like liquid or putty. Once cured, the implant solidifies or stiffens on the joint surface.

Generally, the distal end of a light delivery system can be or can take any shape(s) that allows it to deliver light to an adhesive. In one embodiment, the light delivery instrument 700 may end in a "plunger" with a convex surface 710 (FIGS. 56A-B). The light delivery instrument 700 may comprise a light emitting end with a fully or semi-transparent material that is also compliant (such as silicone) that can be compressed against a flexible cartilage replacement implant 300, a layer of light-curable adhesive 706, and an apposing bone surface 702. The plunger may deform the flexible implant along the contours of the bone surface 702, so that the implant 300 follows (e.g. runs parallel to) the contour of the bone. The light may be applied through the plunger, through the implant 300, and onto the adhesive 706, thereby curing the adhesive 706 and fixing the implant 300 to the joint surface 702 (e.g. bone or cartilage). What results is a cartilage replacement implant that "lines" the surface of a bone just as natural cartilage does. This process enables the resurfacing of—without significant bone removal—a damaged joint surface that is not axisymmetric, such as in the knee, where the femoral condyles and tibial plateaus have complex geometries. In traditional total joint replacement surgery, a significant amount of bone is resected to make room for a pre-molded, rigid metallic implant with precisely engineered, but simplified, mating surfaces of metal and UHMWPE. In some embodiments, a sheet of flexible cartilage replacement material is applied to a contoured bone surface. The sheet contours to the bone surface during curing. In other embodiments, the sheet conforms to the shape of the bone surface covered by the sheet.

In the present invention, the natural contours of the bone can be kept intact by contour-preserving reaming of the bone surface, followed by the adaptation of a flexible implant over and along the preserved contour, and subsequent light-mediated curing and adhesion as described. A simple removal of damaged cartilage may suffice for the application of the device. Alternatively, a plunger can be concave so that the implant is pressed against a convex surface. Alternatively, a plunger can be configured to "roll" or "slide" over an implant, optionally while light is applied so that an implant may be "ironed" onto a joint surface manually. A shape of a plunger in this case can be any (e.g. rectangular, spherical, or cylindrical). A distal end of a light delivery system may have a plurality of ends ("plungers") configured to adapt to the surface of an implant connected with a contour of a joint during implantation.

Figure 57:
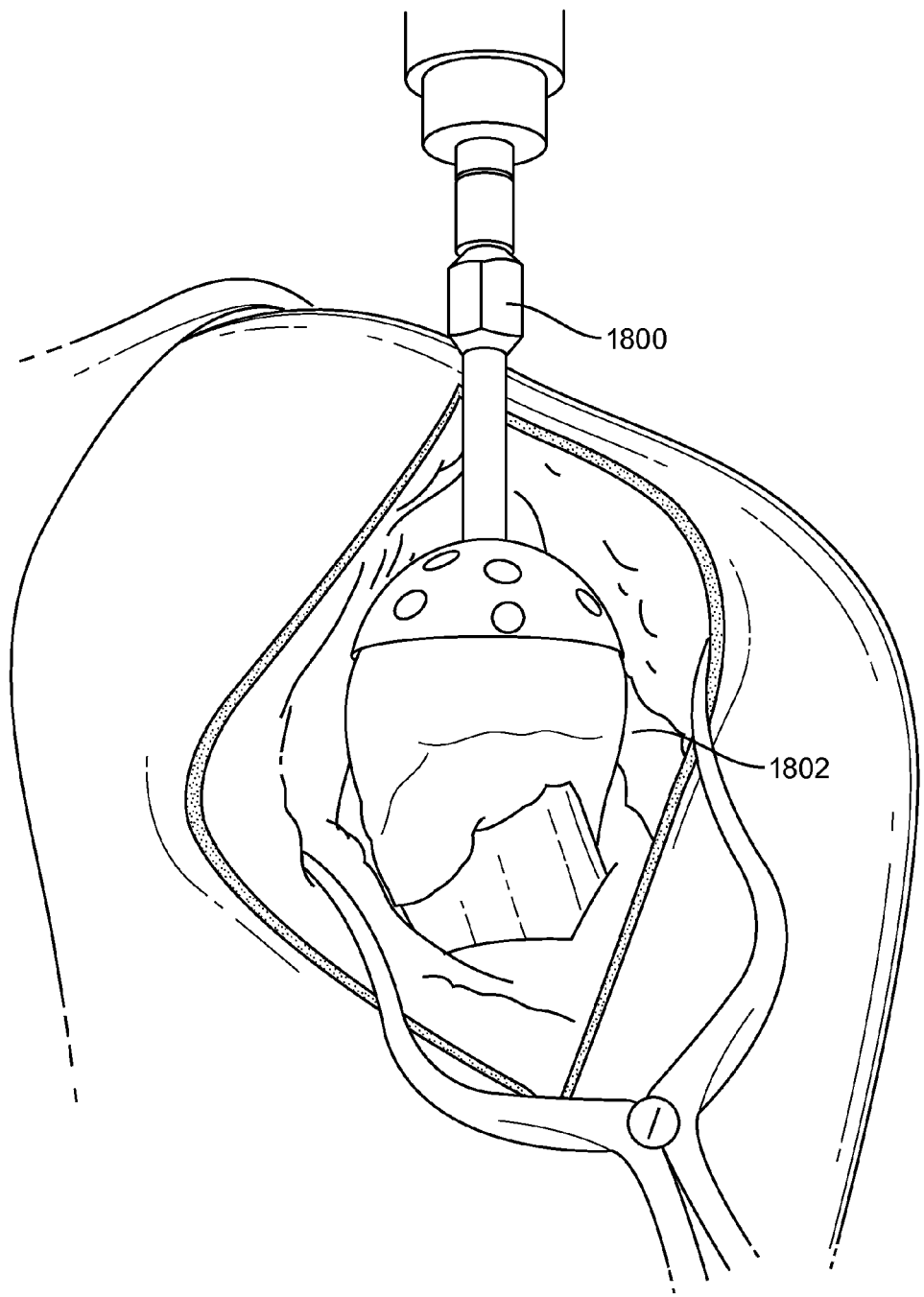
FIG. 57 shows shaping of a femoral head with a bone reamer.

Methods of using the described systems and devices will now be described in greater detail. Some embodiments provide for methods of replacing cartilage in a joint where the joint area is first prepared by shaping the surface in the joint space. For example, with hip joint replacement, the surface 1802 of the femoral head may be reamed or shaped to more easily accommodate implant attachment (FIG. 57). The femoral head may be reamed by any suitable device 1800 including those described in U.S. patent application Ser. No. 12/973,829 filed Dec. 20, 2010 which is incorporated by reference in its entirety. In other embodiments, the implantation site preparation may include removing tissue from the location. This may entail negatively pressurizing the joint space (e.g. vacuuming) to remove tissue such as blood, fat, bone, moisture etc. from the site.

Figure 58:
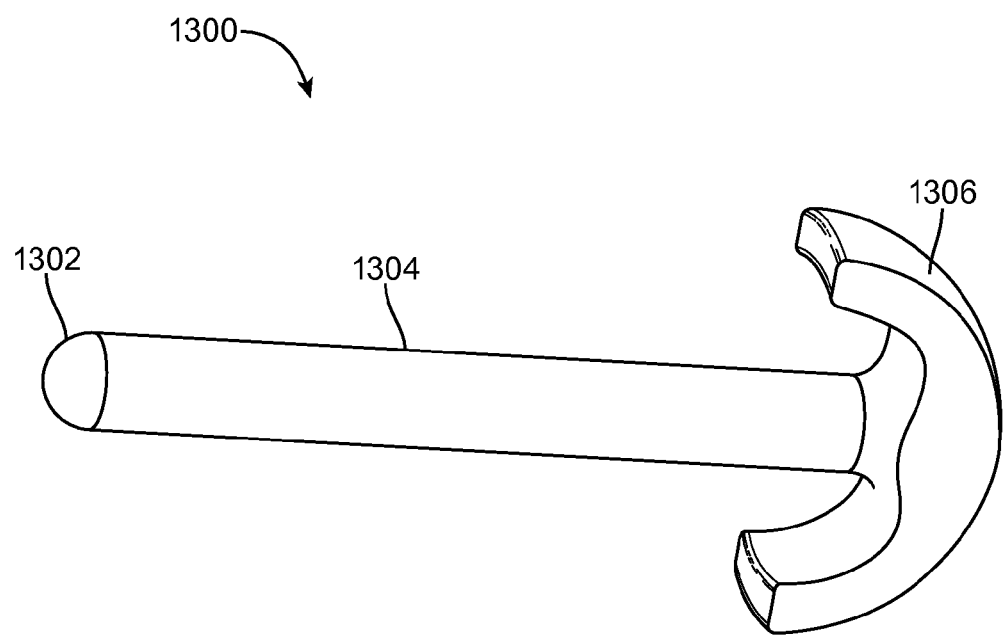
FIG. 58 shows a joint sizer.
Figure 59A:
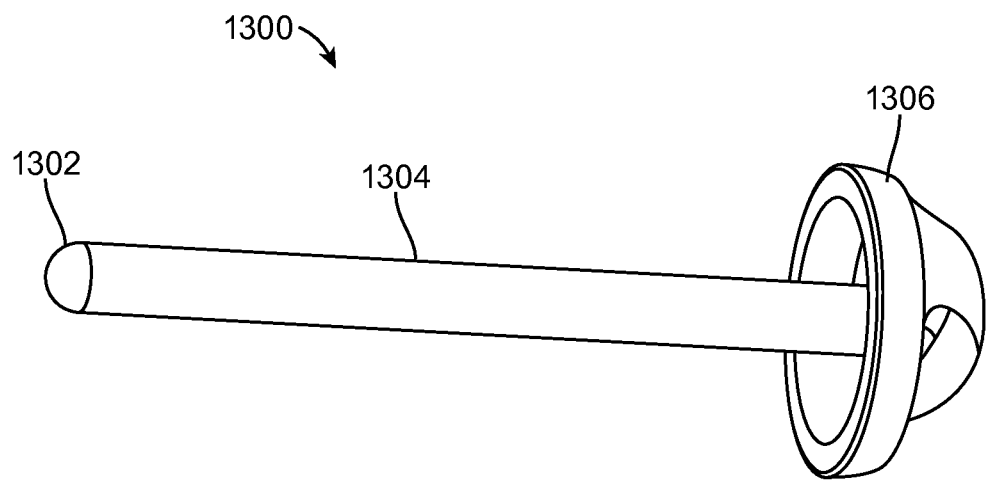
FIGS. 59A-B show an alternative joint sizer.
Figure 59B:
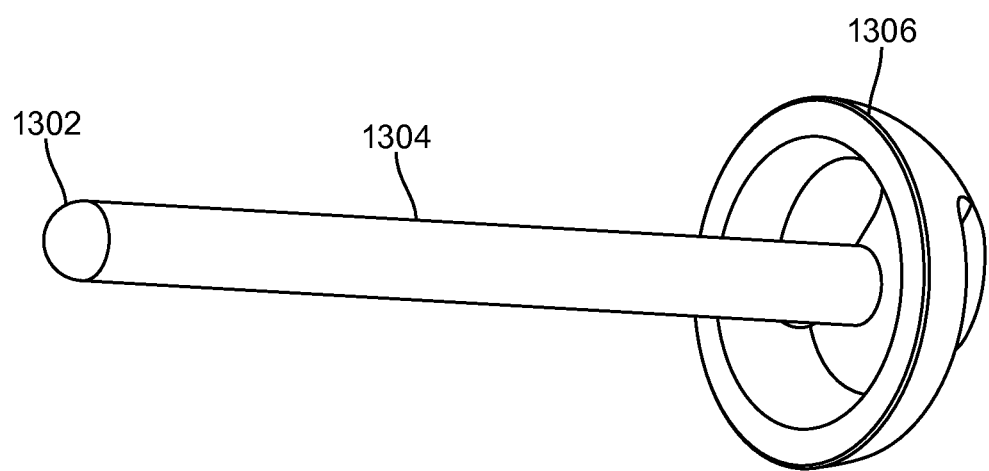

Once the bone surface has been adequately shaped, the size of the bone surface may be measured. With a femoral head or convex surface, a ruler, caliper or template gage may be used to measure the size of the head to determine the corresponding size of the implant needed. For an acetabular or concave surface, a joint sizer such as the ones shown in FIGS. 58-59B may be used. A joint sizer may include a head 1306 at a distal end of an elongate body 1304 with a gripping member 1302 at a proximal end. In some embodiments, the gripping member includes a curved handle 1302. The head may have a convex surface configured for insertion into a joint space. The convex end may be designed to fit into a concave joint space to measure the size of the joint space. The head 1306 may have a spherical shape with a diameter between about 30 mm to about 60 mm. In some embodiments, the head may have a diameter between about 38 mm and about 60 mm. The joint sizer may also provide measurements on the depth of the concave joint space. In some embodiments, the head 1306 measures the joint space. Additionally, the joint sizer can also provide measurements on the orientation of the prepared surface. In some embodiments, the head 1306 is placed in the prepared space. The head 1306 may represent the shape and size of the final implant. For example, if the sizer 1300 shows overhang then the implant would overhang. If the sizer 1300 sits in the space too deeply then the implant will sit too deeply. The sizer 1300 can be manipulated within the space to determine the correct placement of the final implant. The surgeon may use the sizer 1300 to determine how much version or retroversion and/or antegrade or retrograde is desired in the cup position.

Figure 60:
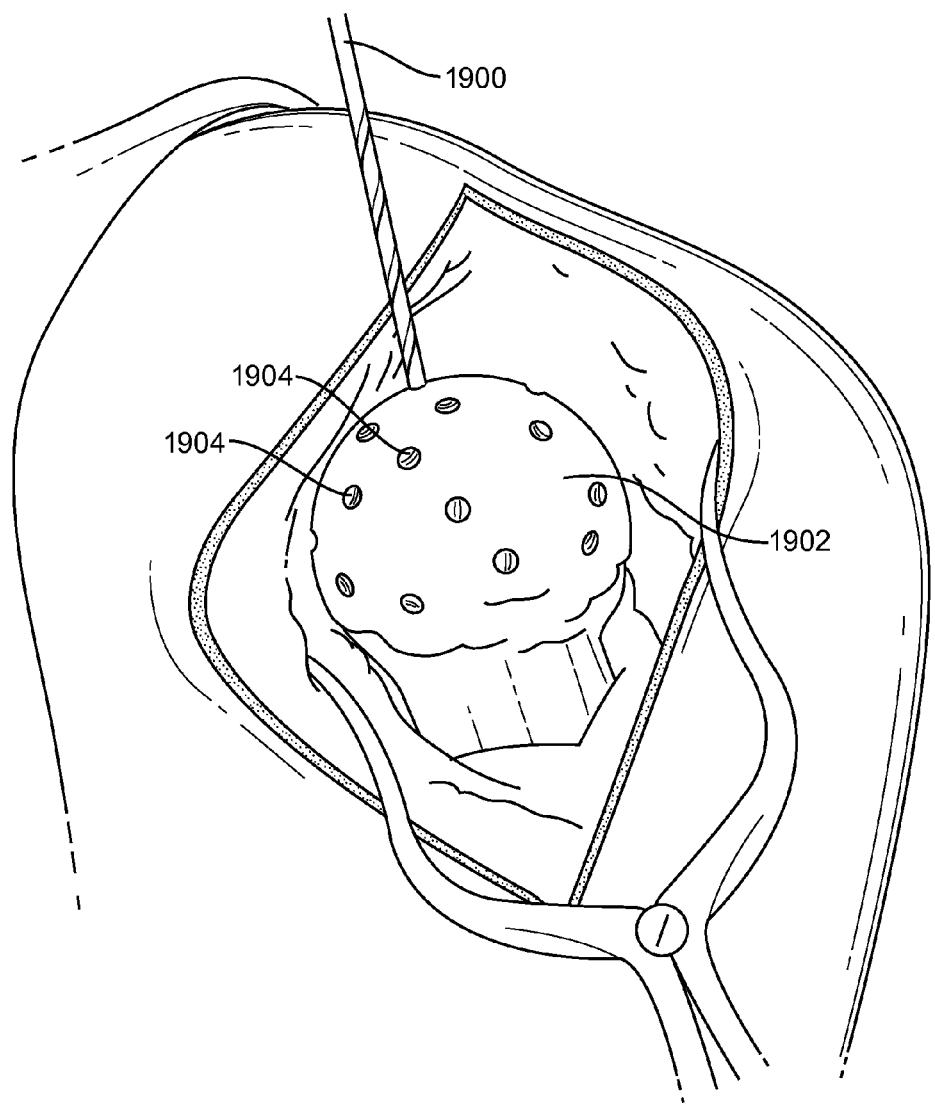
FIG. 60 shows a femoral head with drilled holes.
Figure 61:
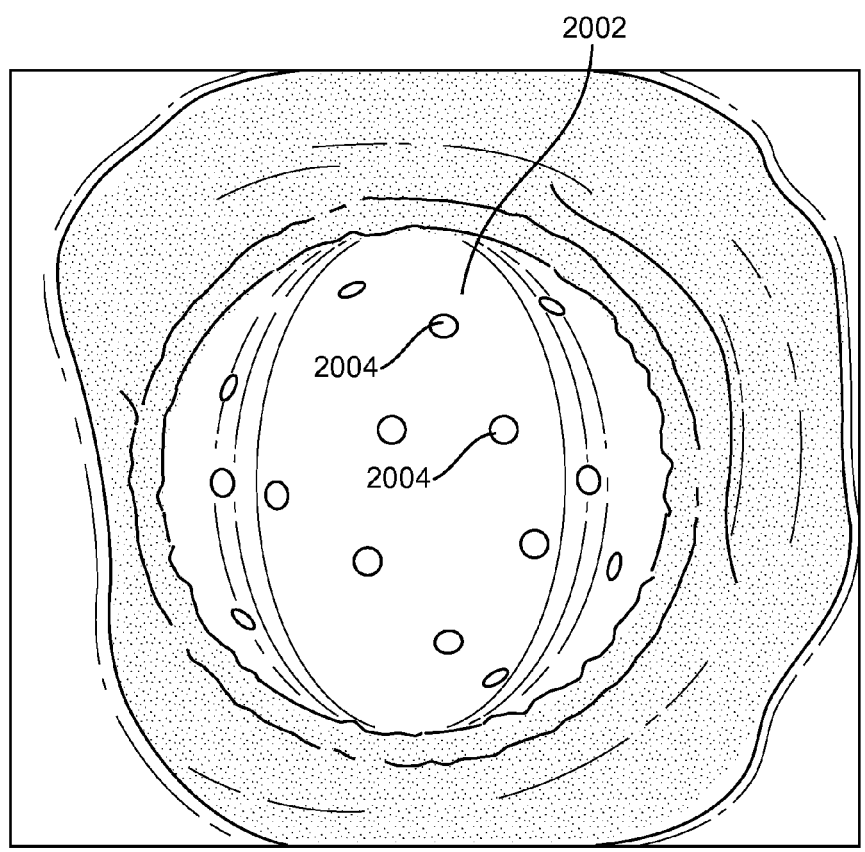
FIG. 61 shows an acetabulum with drilled holes.

Some embodiments provide for creating surface features such as holes in the bone surface. A drill 1900 may be used to create holes 1904 in the bone surface 1902 (FIG. 60). In some embodiments, the drill creates holes with a diameter of about 3 mm and depth of about 5 mm. The number of holes and depth are variable. In some cases, the holes are created to make pockets for receiving the adhesive compound. These pockets can help promote the attachment and adhesion of the implant to the bone surface. FIG. 61 shows holes 2004 created on an acetabular surface 2002.

Once the implantation site is prepared, an implant can be placed into the site. The implant alone may be brought into direct contact with the joint surface. Alternatively, the implant may be provided in a container, a component of a container, or a shaper. For example, the implant may be provided in a shaping element or holder that supports, maintains, and/or conforms the implant shape to the shaper's shape. FIGS. 4 and 24-25 provide examples of containers and container components that surround and enclose the implant while also helping to maintain, conform, or support the implant shape. Those figures as well as FIGS. 28A-B also show shapers, e.g. 608, that can be used with or independent of a container. For example, the shaper 608 in FIGS. 28A-B may not be part of another device or container and can be used directly with the implant to support the shape of the implant for attachment to the target site. In other embodiments, the shaper is a component of the container.

Continuing with the femoral head example and referring to FIGS. 29A-B, the flexible implant 300 may be directly brought into contact with a joint surface of the femoral head 912. Alternatively, the flexible implant 300 may be contained in a shaper 608 when brought into contact with the bone surface. For placement into the joint, the inner concave surface of the implant 300 is contacted to the outer convex surface of the femoral head 912.

The shaper 608 may be made from an elastomeric or expandable material that can stretch or radially expand. This can be accomplished by a variety of means, including the shown longitudinal slots 620 and segmented members 612. During placement, the femoral head implant 300 may flex and stretch to slide over 180 degrees of the femoral head. In doing so, an attached shaper 608 has a portion that radially expands to accommodate the widest area (e.g. area near the equator) of the femoral head 912. In some embodiments, the shaper 608 radially contracts once the distal opening 630 is past the equator of the femoral head 912. In other embodiments, the shaper has resilient expandable members that are biased toward the center of the shaper such that the shaper can move between an expanded state and an unexpanded state where the shaper is biased toward the unexpanded state. Additionally, a shaper along with the implant may have a smaller size during insertion and a larger size during deployment in the joint, and may be configured to be inserted through a small (e.g. arthroscopic) insert.

In some embodiments, a curable compound is placed on the inner surface of the implant prior to implant placement on the joint space. In other embodiments, adhesive is applied after the implant is placed over the bone surface (e.g. femoral head). In such cases, the adhesive can be injected into the interspace between the implant and the bone at the opening of the implant. In one embodiment, positive or negative pressure may be used to change a shape of a device and/or adhesive. A positive pressure may expand or inflate the implant and pressurize the adhesive. The positive pressure may also close or seal a rim of the implant so that the adhesive cannot migrate or escape. This is a way to prescribe the bearing surface with the mold instead of having the bone surface prescribe the backing surface, which in turn, prescribes the bearing surface.

In other embodiments, the adhesive may be applied to the surface of the implantation site rather than the implant. For example, the adhesive may be applied to the joint or bone surface before the implant is placed on the surface. Alternatively, the adhesive may be placed in the interspace between the implant and bone after the implant is positioned on the target site.

Where an adhesive is not evenly spread over the area between the implant and joint surface, further distribution may be accomplished by applying spreading force to the implant or the container component/shaper 608. One way to do so is to apply a force to the north pole 654 of the implant 300 or container component/shaper 608. Where the container component/shaper 608 has a proximal opening 652 over the north pole of the implant, an adhesive spreading device, such as those shown in FIGS. 32-50, can apply a distally directed force toward the femoral head. Side forces may be applied to further distribute the adhesive evenly. A distally directed squeezing, pressing, or pushing force may be applied by using a plunger 1002 over the container component/shaper 608 and/or implant. Alternatively, a rolling device, as described above may be used to provide a rolling force from the north pole to the distal end of the implant to spread the adhesive in the area between the implant and bone.

Anchoring the implant to the bone or joint can be accomplished by curing the adhesive between the implant and the bone surface. In some embodiments, the adhesive is a pre-polymer capable or polymerizing to attach the implant to the bone surface. Suitable anchoring compounds include bone cements containing PMMA as well as compounds containing urethane, polyurethane, isocyanate, methyl methacrylate MMA, urethane dimethacrylate UDMA, or any other compounds such as those described in: U.S. application Ser. No. 12/409,359 filed Mar. 23, 2009; U.S. application Ser. No. 13/542,464 filed Jul. 5, 2012; and U.S. application Ser. No. 13/573,788 filed Oct. 3, 2012, which are all incorporated by reference in their entirety.

Again, curing can be carried out by thermal, chemical, or light-curing. In some embodiments, a combination of curing techniques may be used. For example, the adhesive may be light and chemically curable. Light may be applied to partially cure the adhesive while the implant is positioned on the bone surface. The surgeon may stop light application prior to complete curing of the adhesive in order to, for example, adjust the position of the implant. Once the adjustment is made, the surgeon may complete curing by applying light or by chemical or thermal curing. In some embodiments, the curing process may be started prior to placing the implant into the joint space but completed once the implant is positioned at the target site.

Where light-curing is used, a light delivery instrument may be used for providing light to the adhesive. In embodiments where the implant alone is on the joint, the light is delivered through a thickness of the implant to reach the adhesive in the space between the implant and joint. In other embodiments, the light penetrates through a transparent, semi-transparent, or translucent section of the implant to reach and cure the adhesive. In further embodiments, the implant may be enclosed partly or completely in a container such as a shaper. The shaper may also comprise portions that allow the penetration or transmission of light through to the implant and to the adhesive. The shaper may also be made out of a semi-transparent, transparent, or translucent to allow transmission of light.

In some cases, the material of the implant or the container may absorb some amount of the light. In such cases, the application of the light may be adjusted to accommodate absorption or other loss that occurs.

In further embodiments, the container component may have a delivery attachment portion for coupling or connecting with a delivery tool. For example, the delivery tool may be an elongate device such as the one shown in FIG. 8 where the surgeon attaches the connector 104 at a distal end of the delivery tool to the attachment member 206 of the container 200. The surgeon then uses the delivery tool with attached container 200 and implant 300 to maneuver the implant into the joint. With thermal curing, the placement of the implant with adhesive into the joint may be sufficient to cure the adhesive. With light-curing, the delivery tool may be a light delivery instrument 102 that is attachable to the container or implant. The surgeon can use the light delivery instrument 102 to maneuver the connected container component and implant 300 with adhesive into a joint space.

Additionally, the rate of the curing process may be controlled. For example, where light is applied for curing, the light may be discontinuously applied—suspended and restarted during polymerization of the adhesive compound. The periodic discontinuous application of light can be used by the surgeon to control the rate of polymerization. Furthermore, the intensity of the light can also be varied to control polymerization rate. In some embodiments, the greater the intensity the faster the cure rate. The cure rate can be controlled or regulated by reducing or increasing or maintaining light intensity (or energy intensity). Ranges of light intensity that can be used to cure include about 0.1 W/cm$^2$ to about 10 W/cm$^2$. In some embodiments, the light comprises ultraviolet light. In other embodiments, the light is a blue light. In some embodiments, the light is visible light.

In further embodiments, it may be advantageous to monitor the temperature of the joint or implant during attachment. The polymerization process may be exothermic and cause heating of the tissues near the implantation site. In the case of light-curing, the intensity of the light may be regulated to avoid dangerous temperature increases or to maintain temperature below a physiological limit.

In some embodiments, the curable compound may be able to form covalent bonds with the implant. For example, the implant and the curable compound may have end groups capable of reacting to create chemical bonds between the implant and the cured adhesive. In further embodiments, the curable compound may partially penetrate through a portion of the implant such that when polymerized, the adhesive polymer may be physically entangled within a portion of the implant. Additionally, the adhesive polymer may form an IPN or semi-IPN within the implant. Moreover, non-covalent bonds such as hydrogen bonds or van der Waals may also be formed between the adhesive and implant. In further embodiments, a portion of the implant may be softened by dissolving, penetrating, or diffusing the adhesive pre-polymer into the implant. For example, portions of a monomer or pre-polymer compound may penetrate and/or diffuse into or through the anchoring surface of the implant and become polymerized in situ forming a continuous phase through and outside the anchoring surface. Any suitable solvent may be used in any of the described embodiments.

An adhesive usable with the described embodiments may be any energy curable material able to connect an implant with a joint surface. In one example, a light-curable adhesive that may be used is a substance whose curing (polymerization and hardening) may be initiated by exposure to light (either visible or ultraviolet) within a relatively short time interval (within about a second to up to several minutes, up to about 10 minutes, up to about 20 minutes, or up to about 30 minutes). Preferably, it is a polymer composite containing acrylic-monomers or derivatives thereof), or a combination of acrylic monomers and acrylate-terminated polymers, such as methyl methacrylate and most preferably a composite of methyl methacrylate (MMA) and acrylate-functionalized polyurethane (PU) oligomers, such as described in: U.S. application Ser. No. 12/409,359 filed Mar. 23, 2009; U.S. application Ser. No. 13/542,464 filed Jul. 5, 2012; and U.S. application Ser. No. 13/573,788 filed Oct. 3, 2012, which are all incorporated by reference in their entirety. The end-group of a polyurethane can be any ethylenically unsaturated functional group, including, but not limited to an acrylamide, acrylate, allyl ether, methacrylate, and vinyl. Another material with which this system can be used to anchor an orthopaedic device is PMMA bone cement, which typically comprises MMA monomer and polymeric filler particles, such as polystyrene.

Once the implant is anchored or attached to the target site such as a joint surface, the shaper or container component (if a container was used) can be removed or detached from the implant. This may be accomplished, for example, by releasing a vacuum that holds the implant onto the shaper.

In additional embodiments, the implant may be stiff or rigid or contain stiff or rigid materials. In such cases, the systems, devices, and methods described can be used with a rigid or stiff implant. For example, the implant containers can be used to enclose and protect the implant for storage and attachment. Additionally, a container component or a shaper may support the structure or shape of a rigid implant. The container component or shaper may also protect one or more surfaces of the rigid implant while the implant is attached to the component or shaper. The rigid material may be, for example, a metal, ceramic and/or ultra-high molecular weight polyethylene (UHMWPE).

In an alternative embodiment, the curable compound may form a coating on a bone surface. The curable compound may be a pre-polymer or a polymer precursor that is applied to a joint surface. Once applied, the compound may be molded or shaped to an appropriate form on the surface. The compound is then polymerized on the surface to form a coating on the joint.

Additionally, a system according to the disclosure may comprise any combinations of (1) an energy-curable (e.g. a light-curable) adhesive, (2) one or more parts of a device enclosure (optionally including a joint implant), (3) an energy (e.g. light) source, (4) an energy delivery instrument, (5) a connector (e.g. a cable) between an energy delivery instrument and a power source, and (6) a power source. Alternatively, an energy (light) source may be at the device enclosure or delivery instrument (e.g. may be battery operated or may have power cord to a wall outlet). Any of these items or combinations of these items may be packaged into a surgical kit. An enclosure of the system may enclose an implant or may not enclose an implant. An implant of the system may be in a substantially open or expanded position, or may be in a compact or furled position (or may be in between). One or more containers (e.g. bag, tube, vial) in a kit may contain adhesive; a container may be energy (e.g. light) blocking. Alternatively, an assembled or partially assembled device enclosure may comprise adhesive and implant. A surgical kit may include an instruction for use. A surgical kit may include packaging that may be clear or colored, and may be energy (e.g. light) blocking. In one example, an adhesive and a device enclosure with an implant may be packaged separately. Additionally, in any of the described embodiments, the container, canisters, or packaging for the implants may maintain moisture and prevent dehydration of the implant. In further embodiments, any of the components, devices, containers, shapers, etc. described can be reusable.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An orthopedic implant delivery system comprising:
a shaper adapted to hold an orthopedic implant and support an implant shape; and
a delivery instrument that is a light delivery instrument comprising a light source and a light applicator adapted to transmit light from the light source to an orthopedic implant held by the shaper, the delivery instrument configured for inserting the orthopedic implant held in the shaper into a joint of a patient, the delivery instrument comprising a gripping member sized and configured to allow manipulation of the delivery instrument.

2. The system of claim 1, wherein the shaper comprises a concave inner surface that is adapted to contact an outer convex surface of an implant held by the shaper.

3. The system of claim 1, wherein the shaper is sufficiently transparent to allow transmission of light through a thickness of an orthopedic implant held by the shaper.

4. The system of claim 1, wherein the shaper comprises a generally spherical shell having a radially expandable diameter.

5. The system of claim 1, wherein the shaper comprises resilient expandable members.

6. The system of claim 1 further comprising a light-curable adhesive on a surface of the implant held in the shaper.

7. The system of claim 1, wherein the light applicator comprises two opposing arms, the opposing arms configured to rotate about a pivot point positioned on a longitudinal axis of the device.

8. The system of claim 7, wherein the light applicator further comprises a plurality of light emitting elements along a surface of each opposing arm.

9. The system of claim 7, wherein the opposing arms have an open configuration and a closed configuration.

10. The system of claim 9, wherein the opposing arms in the closed configuration form a substantially circular arc having angle larger than about 180 degrees.

11. The system of claim 1, wherein the light emitting end of the light applicator has a shape selected from the group consisting of a convex shape, a concave shape, a flat shape, and a wedge shape.

12. The system of claim 1, wherein the light emitting end has a plurality of light emitting elements.

13. The system of claim 1, wherein the delivery instrument is a joint space sizer adapted to be inserted into the joint.

14. An orthopedic implant delivery system comprising:
a shaper adapted to hold an orthopedic implant and support an implant shape;
a delivery instrument configured for inserting the orthopedic implant held in the shaper into a joint of a patient, the delivery instrument comprising a gripping member sized and configured to allow manipulation of the delivery instrument; and
a container having a first component adapted to contain the orthopedic implant, a second component adapted to mate with the first component to surround and contain the implant, and a third component, wherein the third component is the shaper.

15. The system of claim 14, wherein the third component is adapted to mate with the first and second components to surround and contain the implant.

16. The system of claim 14, wherein the shaper is removable from the container when holding an implant.

17. The system of claim 14 further comprising a form mold adapted to surround a portion of the shaper, wherein the form mold maintains the shape of the shaper and the implant when the shaper is separated from the container.

18. The system of claim 14, wherein the implant container is adapted to enclose a portion of the femoral head.

19. An orthopedic implant delivery system comprising:
  a shaper adapted to hold an orthopedic implant and support an implant shape; and
  a delivery instrument that is a curable compound spreading device configured for inserting the orthopedic implant held in the shaper into a joint of a patient, the delivery instrument comprising a gripping member sized and configured to allow manipulation of the delivery instrument.

20. The system of claim 1 further comprising an orthopedic implant inside the container.

21. An orthopedic implant delivery system comprising:
  a shaper adapted to hold an orthopedic implant and support an implant shape;
  a delivery instrument configured for inserting the orthopedic implant held in the shaper into a joint of a patient, the delivery instrument comprising a connector for releasably attaching to the shaper; and
  a container having a first component adapted to surround and contain an implant when mated to a second component, the second component adapted to hold the orthopedic implant.

22. The system of claim 21, wherein the shaper is the second component of the container.

23. The system of claim 22, wherein the delivery instrument is a light delivery instrument comprising a light source and a light applicator adapted to transmit light from the light source to an orthopedic implant held by the second component of the container attached to the connector.

24. The system of claim 22, wherein the delivery device comprises a gripping member having a handle positioned along a lateral axis of the delivery instrument.

25. The system of claim 23, wherein the light applicator is further adapted to transmit light to the implant through the second component of the container attached to the connector.

26. The system of claim 23 wherein the light source is configured to emit light suitable for curing a light-curable compound.

27. The system of claim 23, wherein the light delivery instrument comprises a lightguide cable connecting the light applicator to the light source.

28. The system of claim 23, wherein the light delivery instrument comprises a self-contained power source.

29. The system of claim 23, wherein the light source comprises at least one LED or LED array.

30. The system of claim 23, wherein the second component comprises an opening adapted to engage the light applicator of the light delivery instrument.

31. The system of claim 21, wherein the second component further comprises a light diffuser.

32. The system of claim 21, wherein the first and second components are configured to mate through a threaded interface.

33. The system of claim 21, wherein the first and second components are configured to mate through a vacuum suction interface.

34. The system of claim 21, wherein the second component of the container comprises a lid.

35. The system of claim 21, wherein the second component of the container comprises a lid and an implant shaper.

36. The system of claim 21, wherein the second component of the container comprises a convex spherical surface, the convex spherical surface adapted to engage a concave inner surface of an implant to hold the implant.

37. The system of claim 21, wherein the second component of the container has a cross-sectional diameter between about 38 mm and about 60 mm.

38. The system of claim 21, wherein the first and second components comprise indentations along a perimeter of an outer surface.

39. The system of claim 21, wherein the container is transparent.

40. The system of claim 21, wherein the second component is sufficiently transparent to allow transmission of light through a thickness of an orthopedic implant held by the first component.

41. The system of claim 21, wherein the second component permits transmission of light through a thickness of the second component to an orthopedic implant held by the second component.

42. The system of claim 21, wherein the shaper is adapted protect an implant surface.

\* \* \* \* \*